United States Patent [19]

Piwinski et al.

[11] Patent Number: 5,422,351
[45] Date of Patent: Jun. 6, 1995

[54] BIS-BENZO OR BENZOPYRIDO CYCLOHEPTA PIPERIDENE, PIPERIDYLIDENE AND PIPERAZINE COMPOUNDS, COMPOSITIONS AND METHODS OF USE

[75] Inventors: John J. Piwinski, Parsippany; Michael J. Green, Skillman; Jesse Wong, Union, all of N.J.

[73] Assignee: Schering Corporation, Kenilworth, N.J.

[21] Appl. No.: 949,810

[22] PCT Filed: Jun. 21, 1991

[86] PCT No.: PCT/US91/04162

§ 371 Date: Dec. 14, 1992

§ 102(e) Date: Dec. 14, 1992

[87] PCT Pub. No.: WO92/00293

PCT Pub. Date: Jan. 9, 1992

[51] Int. Cl.⁶ .................. A61K 31/495; A61K 31/44; C07D 401/00; C07D 491/00
[52] U.S. Cl. .................. 514/254; 514/252; 514/290; 514/291; 514/318; 544/360; 544/361; 546/80; 546/89; 546/93; 546/194
[58] Field of Search .................. 544/360, 361; 546/89, 546/80, 93, 194; 514/252, 254, 318, 290, 291

[56] References Cited

U.S. PATENT DOCUMENTS

| | | | |
|---|---|---|---|
| 3,325,501 | 6/1967 | Ettingen et al. | 260/293.59 |
| 3,326,924 | 6/1967 | Villani | 544/361 |
| 3,336,303 | 8/1967 | Coyne et al. | 544/361 |
| 3,357,986 | 12/1967 | Villani | 544/361 |
| 3,381,000 | 4/1968 | Drukker et al. | 514/213 |
| 3,391,143 | 7/1968 | Kaiser et al. | 514/290 |
| 3,409,621 | 11/1968 | Villani | 544/361 |

(List continued on next page.)

FOREIGN PATENT DOCUMENTS 638971 4/1964 Belgium.
644121 8/1964 Belgium.

(List continued on next page.)

OTHER PUBLICATIONS

Villani et al., Journal of Medicinal Chemistry, vol. 15, No. 7, pp. 750-754 (1972).
Arzn. Forsh 36 1311-1314 (1986).

*Primary Examiner*—Cecilia Tsang
*Attorney, Agent, or Firm*—Henry C. Jeanette; James R. Nelson

[57] ABSTRACT

Bis-benzo or benzopyrido piperidene, piperidylidene and piperazine compounds of the formula:

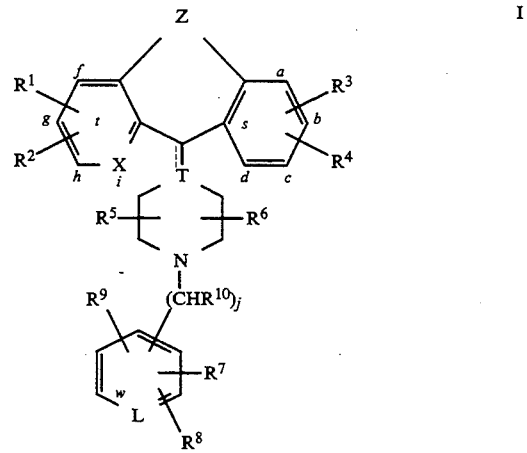

and pharmaceutically acceptable salts thereof are disclosed, wherein Z represents —(C(R$^a$)$_2$)$_m$—Y—(C(R$^a$)$_2$)$_n$— or

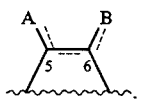

The compounds of Formula I possess anti-allergic and anti-inflammatory activity. Methods for preparing and using the compounds are also described.

40 Claims, No Drawings

U.S. PATENT DOCUMENTS

| | | | |
|---|---|---|---|
| 3,419,565 | 12/1968 | Villani | 544/361 |
| 3,504,088 | 3/1970 | Walker | 514/213 |
| 3,632,572 | 1/1972 | Walker | 514/213 |
| 3,717,647 | 2/1973 | Villani | 424/263 |
| 3,803,153 | 4/1974 | Villani | 260/293.59 |
| 3,803,154 | 4/1974 | Drukker | 260/293.59 |
| 3,966,944 | 6/1976 | Carter | 424/263 |
| 4,021,561 | 5/1977 | Remy et al. | 514/213 |
| 4,072,756 | 2/1978 | Ebnother et al. | 514/213 |
| 4,086,350 | 4/1978 | Zirkie | 514/213 |
| 4,144,337 | 3/1979 | Bastian | 514/213 |
| 4,282,233 | 8/1981 | Vilani | 544/361 |
| 4,355,036 | 10/1982 | Villani | 546/101 |
| 4,356,184 | 10/1982 | Deason et al. | 546/202 |
| 4,609,664 | 9/1986 | Hasspacher | 514/324 |
| 4,616,023 | 10/1986 | Remy et al. | 514/213 |
| 4,659,716 | 4/1987 | Villani et al. | 514/290 |
| 4,826,853 | 5/1989 | Piwinski et al. | 514/290 |
| 4,889,858 | 12/1989 | Uno et al. | 514/213 |
| 4,948,796 | 8/1990 | Hiraiwa et al. | 514/213 |
| 5,089,496 | 2/1992 | Piwinski et al. | 514/253 |
| 5,151,423 | 9/1992 | Piwinski et al. | 514/254 |

FOREIGN PATENT DOCUMENTS

| | | |
|---|---|---|
| 780443 | 3/1968 | Canada . |
| 0047226 | 3/1982 | European Pat. Off. . |
| 0042544 | 10/1984 | European Pat. Off. . |
| 371805 | 6/1990 | European Pat. Off. . |
| 396083 | 11/1990 | European Pat. Off. . |
| 17764 | 4/1964 | Ireland . |
| 1025698 | 4/1966 | United Kingdom . |
| 8803138 | 5/1988 | WIPO . |
| 8910369 | 11/1989 | WIPO . |
| 90/13548 | 11/1990 | WIPO . |

BIS-BENZO OR BENZOPYRIDO CYCLOHEPTA PIPERIDENE, PIPERIDYLIDENE AND PIPERAZINE COMPOUNDS, COMPOSITIONS AND METHODS OF USE

BACKGROUND OF THE INVENTION

The present invention relates to bis-benzo or benzopyrido piperidene, piperidylidene and piperazine compounds and to pharmaceutical compositions and methods of using such compounds.

U.S. Pat. Nos. 3,326,924, 3,717,647 and 4,282,233, European published Application No. 0042544 and Villani et al., *Journal of Medicinal Chemistry*, Vol. 15, No. 7, pp 750–754 (1972) and *Arzn. Forsh* 36 1311–1314 (1986) describe certain 11-(4-piperidylidene)-5H-benzo[5,6]cyclohepta[1,2-b]pyridines as antihistamines. U.S. Pat. No. 4,355,036 describes certain N-substituted piperidylidene compounds.

International Publication Number WO 89/10369 discloses compounds of the formula:

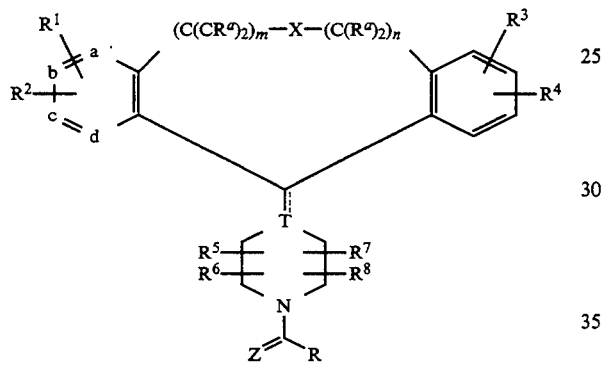

wherein:
one of a, b, c and d represents nitrogen or $-NR^{11}-$, wherein $R^{11}$ is $O^-$, $-CH_3$ or $-(CH^2)_pCO_2H$ wherein p is 1 to 3, and the remaining a, b, c and d groups are CH which may be substituted with $R^1$ or $R^2$;

$R^1$ or $R^2$ may be the same or different and each independently represents halo, $-CF_3$, $-OR^{10}$, $-C(O)R^{10}$, $-S(O)_eR^{12}$ wherein e is 0, 1, or 2, $-N(R^{10})_2$, $-NO_2$, $-SH$, $-CN$, $-OC(O)R^{10}$, $-CO_2R^{10}$, $-OCO_2R^{12}$, $-NR^{10}C(O)R^{10}$, alkyl, alkenyl or alkynyl, which alkyl or alkenyl groups may be substituted with halo, $-OR^{10}$ or $-CO_2R^{10}$, or $R^1$ and $R^2$ may together form a benzene ring fused to the pyridine ring;

$R^{10}$ represents H, alkyl or aryl;

$R^{12}$ represents alkyl or aryl;

$R^3$ and $R^4$ may be the same or different and each independently represents H or any of the substituents of $R^1$ and $R^2$, or $R^3$ and $R^4$ may be taken together to represent a saturated or unsaturated $C_5$ to $C_7$ ring fused to the benzene ring;

$R^5$, $R^6$, $R^7$, and $R^8$ each independently represents H, $-CF_3$, $-CO_2R^{10}$, $-C(O)R^{10}$, alkyl or aryl, which alkyl or aryl may be substituted with $-OR^{10}$, $-SR^{10}$, $-N(R^{10})_2$, $-NO_2$, $-C(O)R^{10}$, $-OC(O)R^{12}$, $-CO_2R^{10}$ and $-OPO_3(R^{10})_2$, or one of $R^5$, $R^6$, $R^7$, and $R^8$ may be taken in combination with R as defined below to represent $-(CH_2)_r$ wherein r is 1 to 4, said combination being optionally substituted with lower alkyl, lower alkoxy, $-CF_3$ or aryl, or $R^5$ may be combined with $R^6$ to represent $=O$ or $=S$, and/or $R^7$ may be combined with $R^8$ to represent $=O$ or $=S$;

T represents carbon or nitrogen, with the dotted line attached to T representing an optional double bond when T is carbon;

m and n are integers 0, 1, 2, or 3, such that the sum of m plus n equals 0 to 3;

when m plus n equals 1, X represents $-O-$, $-S(O)_e-$ wherein e is 0, 1 or 2, $-NR^{10}-$, $-C(O)NR_{10}-$, $-NR^{10}C(O)-$, $-C(S)NR^{10}-$, $-NR^{10}C(S)-$, $-C(O)_2-$ or $-O_2C-$, wherein $R^{10}$ is as defined above;

when m plus n equals 2, X represents $-O-$, $-S(O)_e$ wherein e is 0, 1 or 2, or $-NR^{10}-$;

when m plus n represents 0, X can be any substituent for m plus n equalling 1 and X can also be a direct bond, cyclopropylene or propenylene;

when m plus n equals 3 then X equals a direct bond;

each $R^a$ may be the same or different, and each independently represents H, lower alkyl or phenyl;

Z represents $=O$, $=S$ or $=NR^{13}$ with $R^{13}$ equal to $R^{10}$ or $-CN$, wherein $R^{10}$ is as defined above, such that (a) when Z is O, R may be taken in combination with $R^5$, $R^6$, $R^7$ or $R^8$ as defined above, or R represents H, alkyl, aryl, $-SR^{12}$, $-N(R^{10})_2$, cycloalkyl, alkenyl, alkynyl or $-D$ wherein $-D$ represents heterocycloalkyl,

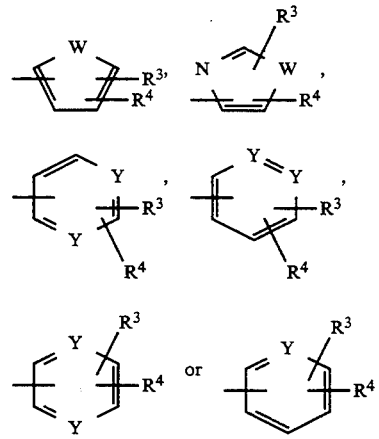

wherein $R^3$ and $R^4$ are as previously defined, and W is O, S or $NR^{10}$, and wherein Y is N or $NR^{11}$, said cycloalkyl, alkyl, alkenyl and alkynyl being optionally substituted with from 1–3 groups selected from halo, $-CON(R^{10})_2$, aryl, $-CO_2R^{10}$, $-OR^{14}$, $-SR^{14}$, $-N(R^{10})_2$, $-N(R^{10})CO_2R^{10}$, $-COR^{14}$, $-NO_2$ or $-D$, wherein $-D$ and $R^{10}$ are as defined above and $R^{14}$ represents $R^{10}$, $-(CH_2)_rOR^{10}$ or $-(CH_2)_qCO_2R^{10}$ wherein r is 1 to 4, q is 0 to 4; said alkenyl and alkynyl R groups not containing $-OH$, $-SH$, or $-N(R^{10})_2$ on a carbon in a double or triple bond respectively; and (b) when Z represents $=S$, R represents in addition to those R groups above, aryloxy or alkoxy; and (c) where Z represents $=NR^{13}$, R represents H, alkyl, aryl, $N(R^{10})_2$, cycloalkyl, alkenyl or alkynyl.

WO 89/10369 generically discloses compounds which can have the structure:

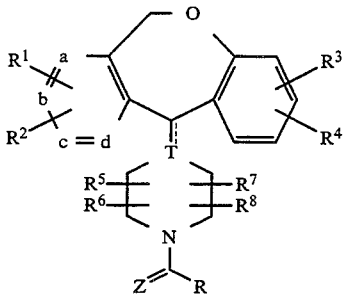

wherein Z can be O and R can be:

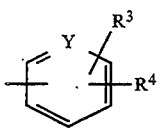

wherein Y can be NR$^{11}$ and R$^{11}$ can be —O$^-$; however, no specific compounds are disclosed with this structure.

U.S. Pat. No. 4,826,853 issued to Piwinski et al. on May 2, 1989 is the priority document for WO 88/03138 which published on May 5, 1988. WO 88/03138 discloses compounds of the formula

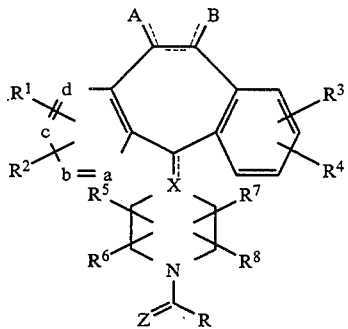

or a pharmaceutically acceptable salt or solvate thereof, wherein:
one of a, b, c and d represents N or NR$^9$ where R$^9$ is O —CH$_3$ or —(CH$_2$)$_n$CO$_2$H where n is 1 to 3, and the remaining a, b, c and d groups are CH, which remaining a, b, c and d groups optionally may be substituted with R$^1$ or R$^2$;
R$^1$ and R$^2$ may be the same or different and each independently represents halo, —CF$_3$, —OR$^{10}$, —COR$^{10}$, —SR$^{10}$, —N(R$^{10}$)$_2$, —NO$_2$, —OC(O)R$^{10}$, —CO$_2$R$^{10}$, —OCO$_2$R$^{11}$, alkynyl, alkenyl or alkyl, which alkyl or alkenyl group may be substituted with halo, —OR$^{10}$ or —CO$_2$R$^{10}$;
R$^3$ and R$^4$ may be the same or different and each independently represents H, any of the substituents of R$^1$ and R$^2$, or R$^3$ and R$^4$ together may represent a saturated or unsaturated C$_5$–C$_7$ ring;
R$^5$, R$^6$, R$^7$ and R$^8$ each independently represent H, —CF$_3$, alkyl or aryl, which alkyl or aryl may be substituted with —OR$^{10}$, —SR$^{10}$, —N(R$^{10}$)$_2$, —NO$_2$, —COR$^{10}$, —OCOR$^{10}$, —OCO$_2$R$^{11}$, —CO$_2$R$^{10}$, —OPO$_3$R$^{10}$ or one of R$^5$, R$^6$, R$^7$ and R$^8$ may be taken in combination with R as defined below to represent —(CH$_2$)$_r$— where r is 1 to 4 which may be substituted with lower alkyl, lower alkoxy, —CF$_3$ or aryl;
R$^{10}$ represents H, alkyl or aryl;
R$^{11}$ represents alkyl or aryl;
X represents N or C, which C may contain an optional double bond to carbon atom 11;
the dotted line between carbon atoms 5 and 6 represents an optional double bond, such that when a double bond is present, A and B independently represent H, —R$^{10}$, —OR$^{11}$ or —OC(O)R$^{10}$, and when no double bond is present between carbon atoms 5 and 6, A and B each independently represent H$_2$, —(OR$^{10}$)$_2$, alkyl and H, (alkyl)$_2$, —H and —OC(O)R$^{10}$, H and —OR$^{10}$, =O, aryl and H, =NOR$^{10}$ or —O—(CH$_2$)$_p$—O— where p is 2, 3 or 4 and R$^{10}$ is as previously defined;
Z represents O, S or H$_2$ such that
(a) when Z is O, R may be taken in combination with R$^5$, R$^6$, R$^7$ or R$^8$ as defined above, or R represents H, aryl, alkyl, —SR$^{11}$, —N(R$^{10}$)$_2$, cycloalkyl, alkenyl, alkynyl or —D wherein —D represents heterocycloalkyl,

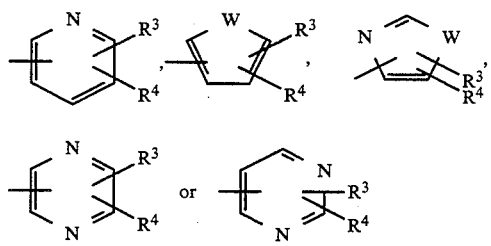

wherein R$^3$ and R$^4$ are as previously defined and W is O, S or NR$^{10}$ wherein R$^{10}$ is as defined above,
said cycloalkyl, alkyl, alkenyl and alkynyl being optionally substituted with from 1–3 groups selected from halo, —CON(R$^{10}$)$_2$, aryl, —CO$_2$R$^{10}$, —OR$^{12}$, —SR$^{12}$, —N(R$^{10}$)$_2$, —N(R$^{10}$)CO$_2$R$^{10}$, —COR$^{12}$, —NO$_2$ or —D, wherein —D and R$^{10}$ are as defined above and R$^{12}$ represents R$^{10}$, —(CH$_2$)$_m$OR$^{10}$ or —(CH$_2$)$_q$CO$_2$R$^{10}$ wherein R$^{10}$ is as previously defined, m is 1 to 4 and q is 0 to 4,
said alkenyl and alkynyl R groups not containing —OH, —SH or —N(R$^{10}$)$_2$ on a carbon containing a double or triple bond respectively;
(b) when Z represents S, R represents in addition to those R groups above, aryloxy or alkoxy; and
(c) when Z represents H$_2$, R represents —COOR$^{10}$, —E—COOR$^{10}$ or —E—OR$^{12}$ where E is alkanediyl which may be substituted with —OR$^{10}$, —SR$^{10}$, —N(R$^{10}$)$_2$ or —D where D, R$^{10}$ and R$^{12}$ are as previously defined. These compounds are disclosed as being useful in the treatment of allergy and inflammation.

During the course of our research on the compounds disclosed in WO 88/03138, we generally found that the compounds having a carbonyl group (Z=O) attached to the piperidyl, piperidylidenyl or piperazinyl nitrogen atom were much stronger antagonists of platelet activating factor (PAF) than the compounds having a CH$_2$ group (Z=H$_2$) attached thereto.

WO 90/13548 published on Nov. 15, 1990 on PCT/US90/02251 which was filed on Apr. 30, 1990 and claims priority to U.S. application Ser. No. 345,604 filed May 1, 1989 discloses compounds similar in structure to the compounds disclosed in WO 88/03138 with the difference being that the R group represents an N-oxide heterocyclic group of the formula (i), (ii), (iii), or (iv):

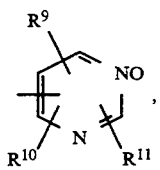

(i)

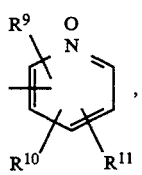

(ii)

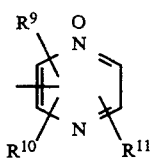

(iii)

or

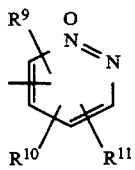

(iv)

wherein $R^9$, $R^{10}$, and $R^{11}$ can be, amongst other groups, H.

Copending U.S. application Ser. No. 625,261 filed on Dec. 10, 1990 is related to WO 90/13548.

The following references have disclosed oxygen or sulfur in the bridgehead of the three ring portion of the molecule:

(1) Canadian Application 780,443, published in the name of Sandoz Patents Ltd.;
(2) Eire 17764, published Apr. 5, 1964 in the name of Sandoz Patents Ltd.;
(3) European Patent Application 81816337.6, Sandoz A. G., published Mar. 10, 1982;
(4) Belgian Application 638,971, Sandoz S. A., published Apr. 21, 1964;
(5) Belgian Application 644,121, Sandoz S. A., published Aug. 20, 1964;
(6) U.S. Pat. No. 4,609,664, issued to Hasspacher on Sep. 2, 1986;
(7) U.S. Pat. No. 3,966,944, issued to Carter on Jun. 29, 1976;
(8) U.S. Pat. No. 3,803,153, issued to Villani on Apr. 9, 1974;
(9) U.S. Pat. No. 3,803,154, issued to Drukker on Apr. 9, 1974; and
(10) U.S. Pat. No. 3,325,501, issued to Ettinsen et al. on Jun. 13, 1967.

None of references (1) to (10) above disclose substitution on the piperidylidene nitrogen similar to that described below for the compounds of this invention.

European Patent Application, Publication No. 0 371 805, published Jun. 6, 1990, priority based on Japanese 303461/88 (30 Nov. 88) and JP64059/89 (16 Mar. 89) discloses compounds useful as hypotensives having the formula:

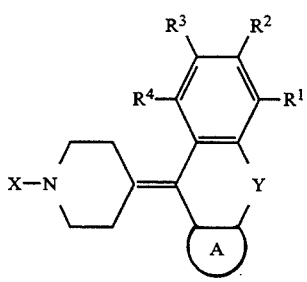

wherein:
any of $R^1$, $R^2$, $R^3$ and $R^4$ may be the same or different from each other and each independently represents a hydrogen atom or other substituent;

X represents an aralkyl- or aryl-containing group having from 6 to 30 carbon atoms or an alkyl group having from 4 to 30 carbon atoms or a cycloalkyl-containing group, which may optionally have substituent(s) and which may be substituted by hetero atom(s) or hetero atom-containing organic group(s) said alkyl group optionally containing unsaturated bond(s);

Y represents a heteroatom or an optionally substituted alkylene chain, the alkylene chain optionally containing hetero atom(s) or unsaturated bond(s); and A represents an optionally substituted condensed aromatic or heterocyclic ring.

European Patent Publication No. 0 371 805 also discloses that if present, the aromatic ring of X or A is benzene, pyridine, pyridazine, or pyrazine, amongst others (see page 3 at about lines 35–40).

Amongst the specific compounds disclosed in European Patent Publication No. 0 371 805, there is included:

(1) 4-(5H-Dibenzo[a,d]cyclohepten-5-ylidene)-1-(2-Picolyl)piperidine;
(2) 4-(5H-Dibenzo[a,d]cyclohepten-5-ylidene)-1-(3-Picolyl)piperidine; and
(3) 4-(5H-Dibenzo[a,d]cyclohepten-5-ylidene)-1-(4-Picolyl)piperidine —(see page 34 at about lines 36–38). It is believed the structures of these compounds are:

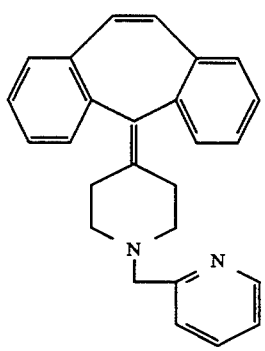

(1)

(2)

(3)

SUMMARY OF THE INVENTION

We have now unexpectedly found that compounds having a group $(CHR^{10})_j$ attached to the piperidyl, piperidylidenyl or piperazinyl nitrogen atom and having a pyridine N-oxide group attached to the $(CHR^{10})_j$ group provide surprisingly good activity as PAF antagonists. These compounds, along with their reduced pyridine counterparts (i.e., L represents N), are also generally better antihistamines than the corresponding compounds having a carbonyl group attached to the piperidyl, piperidylidenyl or piperazinyl nitrogen atom. In particular, we have discovered such characteristics in compounds represented by Formula I

I or a pharmaceutically acceptable salt or solvate thereof, wherein:

Z represents —$(C(R^a)_2)_m$—Y—$(C(R^a)_2)_n$— or

L represents N or N$^+$O$^-$;
X represents CH, N or NR$^{12}$, wherein R$^{12}$ is —O$^-$ or —CH$_3$ (those skilled in the art will appreciate that when R$^{12}$ is —CH$_3$ there is a positive charge on the nitrogen and a pharmaceutically acceptable counterion is present; suitable counterions are well known in the art, and examples include halides (e.g., Br$^-$, I$^-$, Cl$^-$, and F$^-$), NaSO$_4$$_-$, KSO$_4$$_-$, alkyl-SO$_3$$_-$, aryl-SO$_3$$_-$, alkyl-COO$^-$, aryl-COO$^-$, and the like);
R$^1$, R$^2$, R$^3$, and R$^4$ may be the same or different and each independently represents H, halo, —CF$_3$, —OR$^{11}$, —C(=O)R$^{11}$, —SR$^{11}$, —S(O)$_e$R$^{13}$ wherein e is 1 or 2, —N(R$^{11}$)$_2$, —NO$_2$, —OC(=O)R$^{11}$, —CO$_2$R$^{11}$, CN, —OCO$_2$R$^{13}$, —NR$^{11}$C(=O)R$^{11}$, alkyl, aryl, alkenyl or alkynyl, which alkyl group may be substituted with —OR$^{11}$, —SR$^{11}$, —N(R$^{11}$)$_2$ or —CO$_2$R$^{11}$ and which alkenyl group may be substituted with halo, —OR$^{13}$ or —CO$_2$R$^{11}$;
in addition, R$^1$ and R$^2$ may together form a benzene ring fused to the ring t and/or R$^3$ and R$^4$ may together form a benzene ring fused to the rings;
R$^5$ and R$^6$ each independently represents H or alkyl, which alkyl may be substituted with —OR$^{11}$, —SR$^{11}$ or —N(R$^{11}$)$_2$;
in addition, R$^5$ may be combined with R$^6$ to represent =O or =S;
R$^7$, R$^8$ and R$^9$ each independently represents H, halo, —CF$_3$, —OR$^{11}$, —C(O)R$^{11}$, —SR$^{11}$, —S(O)$_e$R$^{13}$ wherein e is 1 or 2, —N(R$^{11}$)$_2$, —NO$_2$, —CO$_2$R$^{11}$, CN, —OCO$_2$R$^{13}$, —OCOR$^{11}$, alkyl, aryl, alkenyl or alkynyl, which alkyl group may be substituted with —OR$^{11}$, —SR$^{11}$, —N(R$^{11}$)$_2$, or —CO$_2$R$^{11}$ and which alkenyl group may be substituted with halo, —OR$^{13}$ or —CO$_2$R$^{11}$;
m and n are integers 0, 1 or 3, such that the sum of m plus n equals 0, 1 or 3;
when m plus n equals 0, Y represents —O—, —S(O)$_e$— (wherein e is 0, 1 or 2), —NR$^{11}$— or a direct bond;
when m plus n equals 1, Y represents —O—, —S(O)$_e$— (wherein e is 0, 1 or 2), or —NR$^{11}$—;
when m plus n equals 3, Y represents a direct bond;
R$^{10}$ represents H or alkyl;
each R$^{11}$ independently represents H, alkyl or aryl;
each R$^{13}$ independently represents alkyl or aryl;
each R$^{14}$ independently represents H or alkyl;
each R$^a$ independently represents H or lower alkyl;
j represents 1, 2 or 3;
T represents CH, C or N, with the dotted line attached to T representing a double bond when T is C and being absent when T is CH or N;
when Z represents the dotted line between carbon atoms 5 and 6 represents an optional double bond, such that when a double bond is present, A and B each independently represent —R$^{11}$, —OR$^{13}$, halo or —OC(O)R$^{11}$, and when no double bond is present between carbon atoms 5 and 6, A and B each independently represent H$_2$, —(OR$^{13}$)$_2$, (alkyl and H), (alkyl)$_2$, (—H and —OC(O)R$^{11}$), (H and —OR$^{11}$), =O or =NOR$^{14}$; and with the proviso that when Z represents

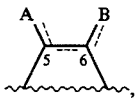

and X represents CH, and T represents C such that the dotted line attached to T represents a double bond, then L represents N$^+$O$^-$. Preferably, for the compounds of Formula I: R$^1$, R$^2$, R$^3$, and R$^4$ are each independently selected from the group consisting of H, alkyl, halo, —N(R$^{11}$)$_2$, and —OR$^{11}$; R$^5$ and R$^6$ are each independently selected from the group consisting of H and lower alkyl; R$^7$ and R$^8$ are each H; R$^9$ is selected from the group consisting of H, halo, —CF$_3$, —OR$^{11}$, —SR$^{11}$, —N(R$^{11}$)$_2$, and lower alkyl, with R$^9$ most preferably being H; T is selected from the group consisting of N and C; L is the N-oxide (i.e., N$^+$O$^-$), and most preferably L is in the para position relative to the bond connecting the pyridine ring (ring w) to the rest of the compound; j is 1; R$^{10}$ is H; and R$^{11}$ is selected from the group consisting of H or lower alkyl.

In one embodiment of this invention, Z represents

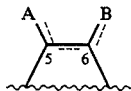

in Formula I, thus providing compounds represented by Formula Ia:

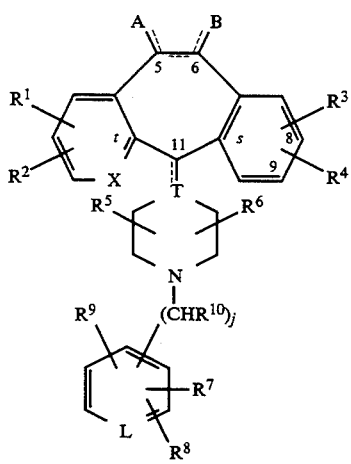

Ia or a pharmaceutically acceptable salt or solvate thereof, wherein R$^1$, R$^2$, R$^3$, R$^4$, R$^5$, R$^6$, R$^7$, R$^8$, R$^9$, R$^{10}$, X, A, B, T and L are as defined above for Formula I.

Preferably, for the compounds represented by Formula Ia: the double bond between carbon atoms 5 and 6 is absent and (a) both A and B are H$_2$ or (b) one of A or B represents (H and OH) on the same carbon atom or is =O, and the other is H$_2$; R$^5$ and R$^6$ each independently represent H or lower alkyl; R$^1$, R$^2$, R$^3$ and R$^4$ each independently represent H, alkyl, halo, N(R$^{11}$)$_2$ or OR$^{11}$; R$^7$ and R$^8$ are both H; R$^9$ represents H, halo, —CF$_3$, —OR$^{11}$, —SR$^{11}$, —N(R$^{11}$)$_2$, or lower alkyl, and most preferably represents H; T represents N or C; L is in the para position relative to the bond connecting the pyridine ring to the rest of the compound; j is 1; and R$^{10}$ represents H.

A preferred embodiment of the compounds of Formula Ia is represented by the compounds of Formula Ib:

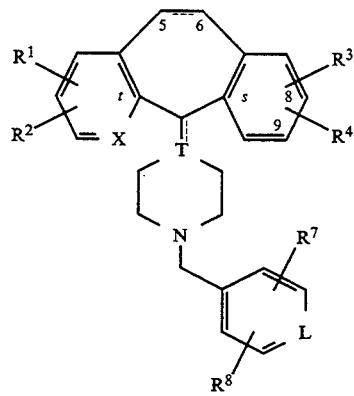

Ib or a pharmaceutically acceptable salt or solvate thereof, wherein:

the dotted lines represent optional double bonds;

X represents CH, N or N$^+$O$^-$;

R$^7$ and R$^8$ each independently represent H, halo, —CF$_3$, —OR$^{11}$, —SR$^{11}$, —N(R$^{11}$)$_2$, alkyl, aryl, alkenyl or alkynyl;

with the proviso that when X represents CH, and T represents C such that the dotted line attached to T represents a double bond, then L represents N$^+$O$^-$; and all other substituents for Formula Ib are as defined above for Formula I.

Preferably, in compounds of Formula Ib: the optional double bond between carbon atoms 5 and 6 is absent; R$^1$ and R$^2$ each independently represent H, alkyl or halo; and R$^3$ and R$^4$ each independently represent H or halo, with R$^3$ most preferably representing H, Cl, Br or F in the indicated 8 position and R$^4$ most preferably representing H in the indicated 9 position.

Representative compounds of Formula Ib include:

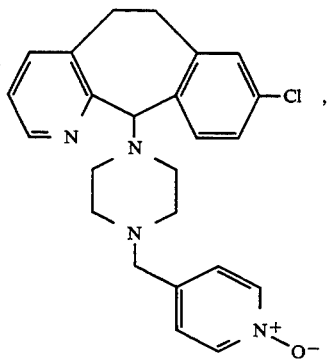

Ic

Ic (S-enantiomer)
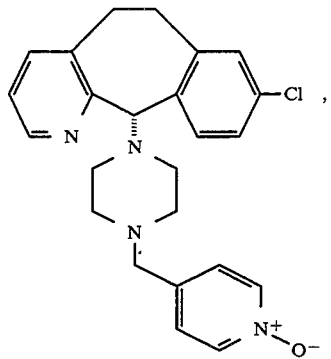
Ic (R-enantiomer)
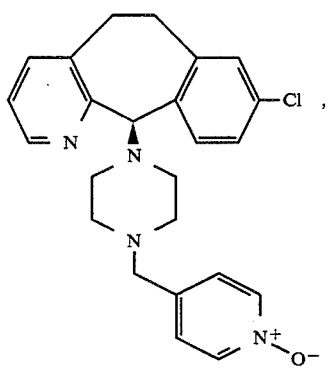
Id
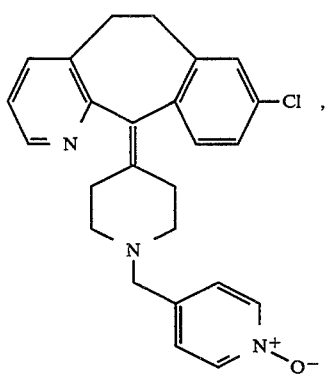
Ie
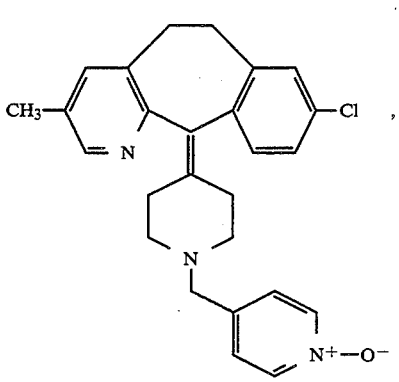
If
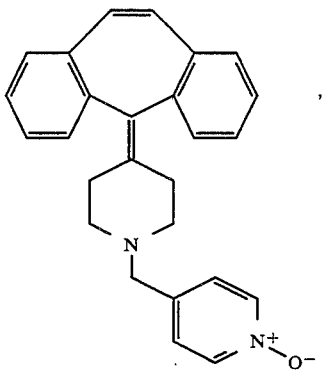
Ig
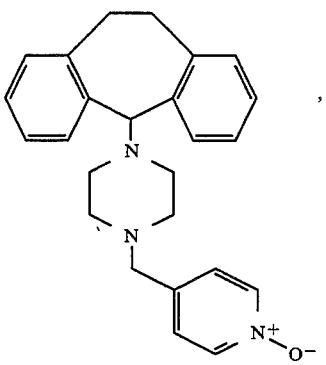
Ih, or
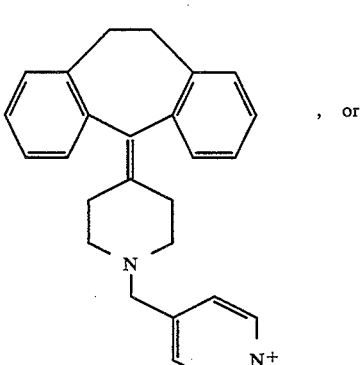
Ii
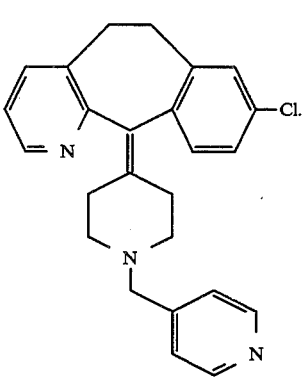
In another embodiment of this invention, Z represents —$(C(R^a)_2)_m$—Y—$(C(R^a)_2)_n$— in Formula I, thus providing compounds represented by Formula Ij:

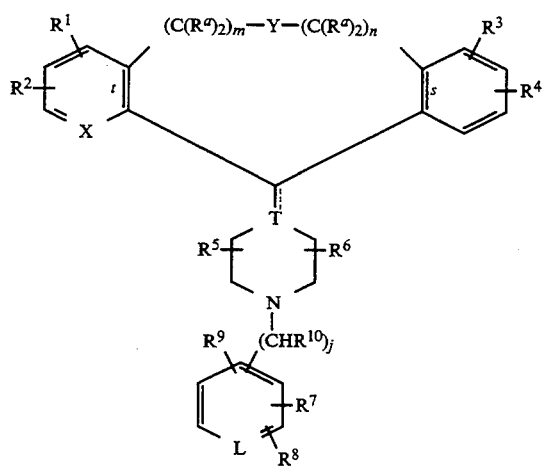

Ij or a pharmaceutically acceptable salt or solvate thereof, wherein the substituents are as defined above for Formula I.

Preferably, in the compounds of Formula Ij: $R^1$, $R^2$, $R^3$ and $R^4$ each independently represent H, alkyl, halo, $N(R^{11})_2$ or $OR^{11}$; $R^5$ and $R^6$ each independently represent H or lower alkyl; $R^7$ and $R^8$ are both H; $R^9$ represents H, halo, $-CF_3$, $-OR^{11}$, $-SR^{11}$, $-N(R^{11})_2$, or lower alkyl, and most preferably represents H; T represents N or C, with the dotted line attached to T representing a double bond when T is C; L is in the para position relative to the bond connecting the pyridine ring to the rest of the compound; j is 1; $R^{10}$ is H; and $R^{11}$ represents H or lower alkyl.

A preferred embodiment of the compounds of Formula Ij provides compounds of Formula Ik:

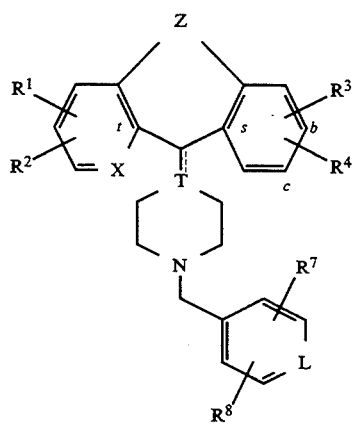

Ik or a pharmaceutically acceptable salt or solvate thereof, wherein:

X represents CH, N or $N^+O^-$;

$R^7$ and $R^8$ each independently represent H, halo, $-CF_3$, $-OR^{11}$, $-SR^{11}$, $-N(R^{11})_2$, alkyl, aryl, alkenyl or alkynyl;

Z represents $-C(R^a)_2-Y-$, $-Y-C(R^a)_2-$, $-Y-$, $-CH_2CH_2CH_2-$ or a direct bond where Y represents $-O-$, $-S-$, $-NR^{10}$; and all of the other substituents in Formula Ik are as defined above for Formula I.

Preferably, in the compounds of Formula Ik: L represents $N^+O^-$; $R^1$ and $R^2$ each independently represent H, alkyl or halo; $R^3$ and $R^4$ each independently represent H or halo; $R^7$ and $R^8$ represent H; Z represents $-CH_2-Y-$, $-Y-CH_2-$, $-Y-$, $-CH_2CH_2CH_2-$ or a direct bond wherein Y represents $-O-$ or $-S-$; and T represents C or N, with the dotted line attached to T representing an optional double bond when T is C.

Representative compounds of Formula Ik include:

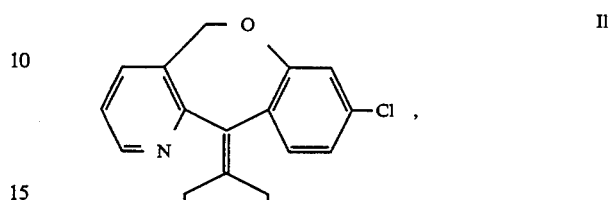

Il

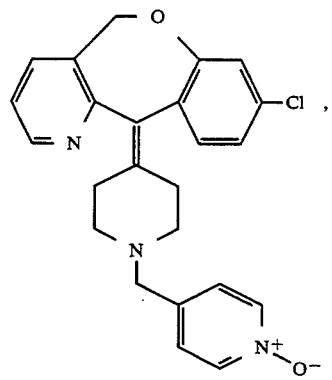

Im

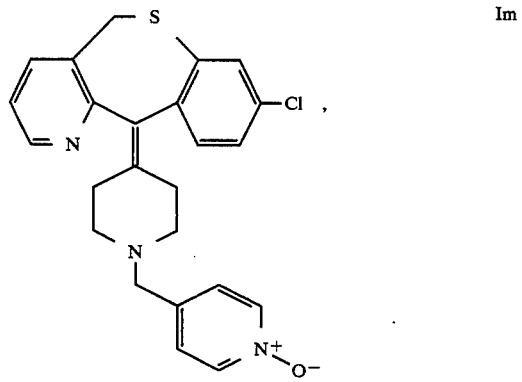

In

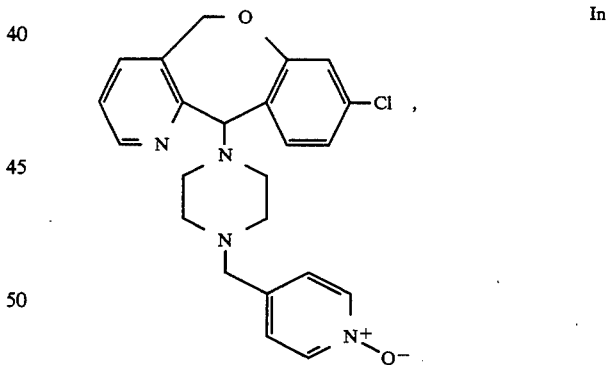

Io

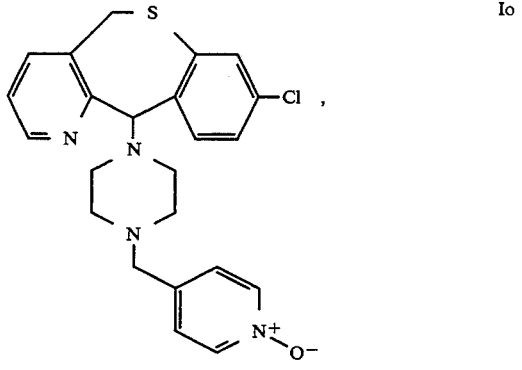

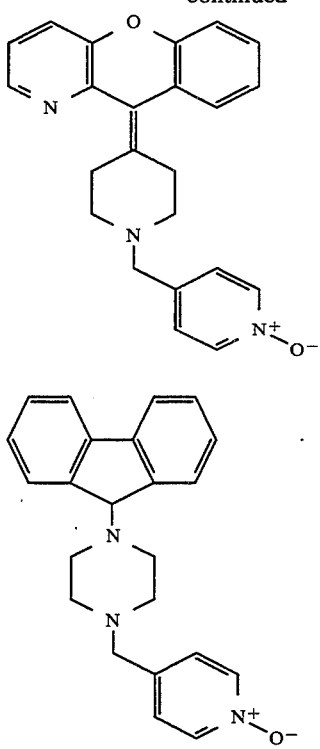

The invention also involves a pharmaceutical composition comprising a compound of Formula I of the invention in combination with a pharmaceutically acceptable carrier.

The invention further involves a method for treating allergic reaction or inflammation in a mammal comprising administering to the mammal an effective amount of a compound of Formula I of the invention for such purpose.

DETAILED DESCRIPTION OF THE INVENTION

Certain compounds of the invention may exist in different isomeric (e.g., enantiomers and diastereoisomers) as well as conformational forms. The invention contemplates all such isomers both in pure form and in admixture, including racemic mixtures. Enol forms are also included. For example, hydroxy substituted pyridinyl groups can also exists in their keto form:

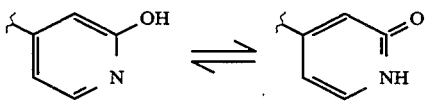

The compounds of the invention of Formula I can exist in unsolvated as well as solvated forms, including hydrated forms, e.g., hemi-hydrate. In general, the solvated forms, with pharmaceutically acceptable solvents such as water, ethanol and the like are equivalent to the unsolvated forms for purposes of the invention.

As noted above, the pyridine and benzene ring structures of formula I may contain one or more substituents $R^1$, $R^2$, $R^3$ and $R^4$, and the pyridine ring containing L (ring w) may contain one or more substituents $R^7$, $R^8$, and $R^9$. In compounds where there is more than one substituent on a ring, the substituents may be the same or different. Thus compounds having combinations of such substituents are within the scope of the invention. Also, the lines drawn into the rings from the $R^1$, $R^2$, $R^3$, $R^4$, $R^7$, $R^8$, and $R^9$ groups indicate that such groups may be attached at any of the available positions. For example, the $R^1$ and $R^2$ groups may be attached to a carbon atom at the f, g, h, or i positions while the $R^3$ and $R^4$ groups may be attached at any of the a, b, c or d positions.

$R^5$ and $R^6$ are attached to the piperidyl, piperidylidenyl or piperazinyl ring. As such they may be the same or different. The variables $R^5$ and $R^6$ in addition to representing H, may represent variables attached to the same or different carbon atoms in said ring. For example, when $R^5$ and $R^6$ are combined to represent =O or =S, they are attached to the same carbon atom.

The N-oxides are illustrated herein using the terms NO, N→O, N—O and N+O−. All are considered equivalent as used herein.

Lines drawn into the ring systems indicate that the indicated bond may be attached to any of the substitutable ring carbon atoms.

Certain compounds of the invention will be acidic in nature, e.g. those compounds which possess a carboxyl or phenolic hydroxyl group. These compounds may form pharmaceutically acceptable salts. Examples of such salts may include sodium, potassium, calcium, aluminum, gold and silver salts. Also contemplated are salts formed with pharmaceutically acceptable amines such as ammonia, alkyl amines, hydroxyalkylamines, N-methylglucamine and the like.

Certain basic compounds of the invention also form pharmaceutically acceptable salts, e.g., acid addition salts. For example, the pyrido-nitrogen atoms may form salts with strong acid, while compounds having basic substituents such as amino groups also form salts with weaker acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those in the art. The salts are prepared by contacting the free base form with a sufficient amount of the desired acid to produce a salt in the conventional manner. The free base forms may be regenerated by treating the salt with a suitable dilute aqueous base solution such as dilute aqueous sodium hydroxide, potassium carbonate, ammonia and sodium bicarbonate. The free base forms differ from their respective salt forms somewhat in certain physical properties, such as solubility in polar solvents, but the acid and base salts are otherwise equivalent to their respective free base forms for purposes of the invention.

All such acid and base salts are intended to be pharmaceutically acceptable salts within the scope of the invention and all acid and base salts are considered equivalent to the free forms of the corresponding compounds for purposes of the invention.

As used herein, the following terms are used as defined below unless otherwise indicated:

alkyl—(including the alkyl portions of alkoxy, alkylamino and dialkylamino)—represents straight and branched carbon chains and contains from one to twenty carbon atoms, preferably one to six carbon atoms;

cycloalkyl—represents saturated carbocyclic rings branched or unbranched of from 3 to 20 carbon atoms, preferably 3 to 7 carbon atoms;

alkenyl—represents straight and branched carbon chains having at least one carbon to carbon double bond and containing from 2 to 12 carbon atoms, preferably from 2 to 6 carbon atoms;

alkynyl—represents straight and branched carbon chains having at least one carbon to carbon triple bond and containing from 2 to 12 carbon atoms, preferably from 2 to 6 carbon atoms;

aryl—represents a carbocyclic group (preferably phenyl or substituted phenyl) containing from 6 to 14 carbon atoms and having at least one phenyl or fused phenylene ring, with all available substitutable carbon atoms of the carbocyclic group being intended as possible points of attachment, said carbocyclic group being optionally substituted with one or more of halo, alkyl, hydroxy, alkoxy, phenoxy, cyano, cycloalkyl, alkenyloxy, alkynyloxy, —SH, —S(O)$_e$R$^{13}$ (wherein e is 1 or 2 and R$^{13}$ is alkyl or aryl), —CF$_3$, amino, alkylamino, dialkylamino, —COOR$^{13}$ or —NO$_2$;

lower alkyl—represents straight and branched carbon chains and contains from one to six carbon atoms, with one to three carbon being preferred;

substituted phenyl—represents a phenyl group in which 1 to 3 hydrogen atoms thereof are replaced by the same or different substituents independently chosen from halo, alkyl, hydroxy, alkoxy, phenoxy, cyano, cycloalkyl, alkenyloxy, alkynyloxy, —SH, —S(O)$_e$R$^{13}$ (wherein e is 1 or 2 and R$^{13}$ is alkyl or aryl), —CF$_3$, amino, alkylamino, dialkylamino, —COOR$^{13}$ or —NO$_2$; and halo—represents fluoro, chloro, bromo and iodo.

PREPARATION OF COMPOUNDS OF THE INVENTION I

The following processes may be employed to produce compounds of Formula I.

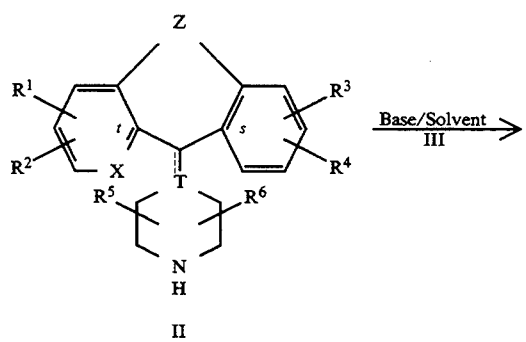

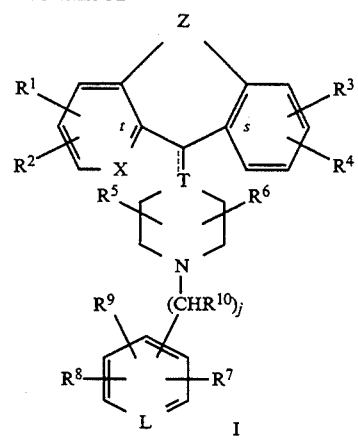

wherein III represents

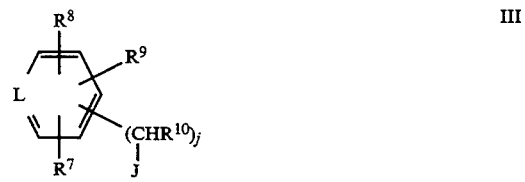

Compounds of Formula I can best be prepared via alkylation of the unsubstituted piperidines of Formula II as illustrated above. Treatment of II with a suitably substituted pyridyl reagent of Formula III, wherein J is a leaving group such as halo, mesyl or tosyl, provides compounds of Formula I. The reaction is usually conducted in an inert solvent such as tetrahydrofuran or methylene chloride at a suitable temperature, usually at reflux, although temperatures in the range of 0° C. to 80° C. can be employed. A suitable base, such as triethylamine or pyridine, is generally utilized. In some reactions, such as when the compound can act as its own base, a base may not be necessary. The pyridyl reagent III can be prepared from the corresponding alcohol using well known procedures (e.g., mesyl chloride in triethylamine for J=OSO$_2$CH$_3$, triphenylphosphine/carbon tetrabromide for J=Br, and thionyl chloride for J=Cl).

Alternatively, many of the compounds of Formula I may be prepared via reductive amination of the unsubstituted piperidine II with the appropriately substituted pyridinecarboxaldehyde IV as illustrated below:

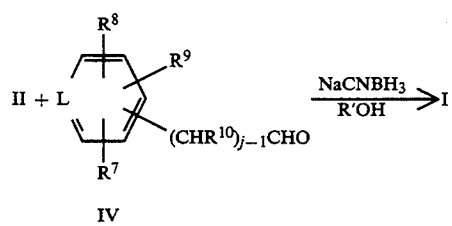

The reaction is typically carried out in a polar solvent, such as methanol or ethanol, and optionally in the presence of a dehydrating agent such as 3Å molecular sieves. The presence of a reducing agent such as NaCNBH$_3$ or H$_2$/Pd—C is necessary in order to reduce the intermediate Schiff base. Temperatures for the reaction are typically held between about 0° to about 100° C. which temperatures are easily determined by one skilled in the art based upon the solvent employed and the pyridinecarboxaldehyde IV used.

Some of the compounds of Formula I may be prepared via reduction of the corresponding amides of Formula V as illustrated below:

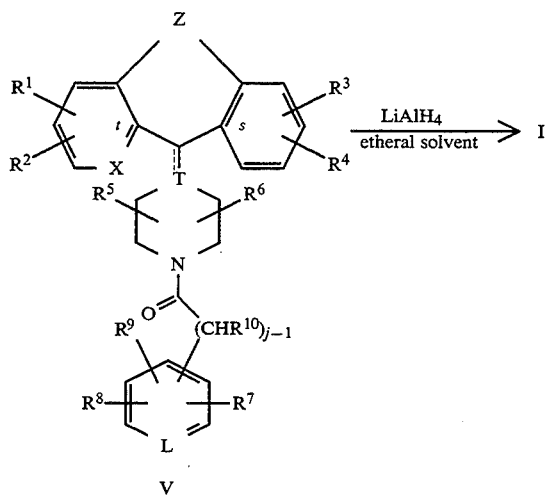

V

Thus, if the amide V were to be treated with lithium aluminum hydride or similar reducing agent, the carbonyl function would be reduced to provide the compound of Formula I. The reaction would be typically carried out in an inert solvent at a temperature range of about 0° C. to reflux. Usually an etheral solvent such as tetrahydrofuran or ethyl ether would be used. This method would be limited to cases where the reducing agent will not affect the reduction of other functional groups such as esters and ketones. The substituted amide V can be obtained via the acylation of II with a compound of formula VI in the presence of a base as illustrated below.

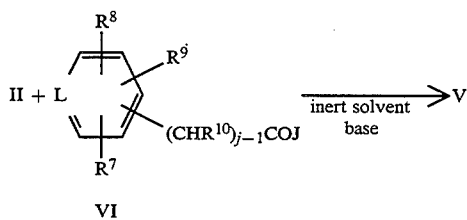

VI wherein J is a leaving group. If compound VI is an acyl halide (i.e., J=halo) or an acyl anhydride (i.e., J=O(-CO)R' wherein R' can be, for example,

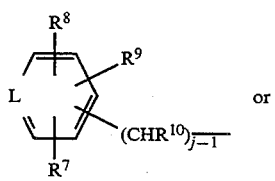

alkyl or aryl), the corresponding amide V is usually formed by simple treatment of VI with the amine II at room temperature. The reaction is usually conducted in an inert solvent, such as methylene chloride, tetrahydrofuran or toluene, in the presence of a base such as triethylamine. Alternatively, if J is hydroxy, a coupling reagent is necessary to form the compound of formula V. Examples of coupling agents include 1-(3-dimethylaminopropyl)-3-ethyl carbodiimide hydrochloride (DEC), N,N-dicyclohexylcarbodiimide (DCC) and N,N'-carbonyl-diimidazole (CDI).

The corresponding N-oxides of the invention (e.g., when X in Formula I is $N^+$—$O^-$) can be prepared by treating the corresponding non-oxidized compound (provided that T is carbon) with an appropriate oxidizing agent in an inert solvent. Suitable oxidizing agents are 3-chloroperoxybenzoic acid in methylene chloride or peracetic acid in acetic acid. The reaction is usually carried out at low temperature (e.g. about −10° C.) in order to minimize the formation of side products, although temperatures in the range of about 0° C. to reflux are sometimes employed. If T=N, then this nitrogen must be protected as its salt or other complex (e.g., complex with $BF_3$) before oxidation.

Compounds of Formula II are prepared by removal of the carbamoyl moiety ($CO_2R''$ wherein R'' is an alkyl or aryl group) from the corresponding carbamate VII via either acid ($HCl/H_2O$/reflux) or base ($KOH/H_2O$/reflux) hydrolysis as illustrated below:

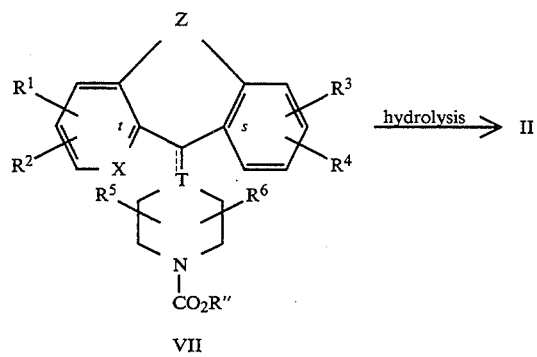

VII

Alternatively, depending on the nature of R'', as determined by those skilled in the art, a compound of Formula VII may be treated with an organometalic reagent (e.g., $CH_3Li$ wherein R'' is an alkyl group such as ethyl) or a reductive reagent (e.g., Zn in acid wherein R'' is 2,2,2-trichloroethyl) in order to produce a compound of Formula II.

Compound VII may be prepared from the N-alkyl (preferably N-methyl) compound shown as Formula VIII below, in accordance with the procedures disclosed in U.S. Pat. No. 4,282,233 and U.S. Pat. No. 4,335,036.

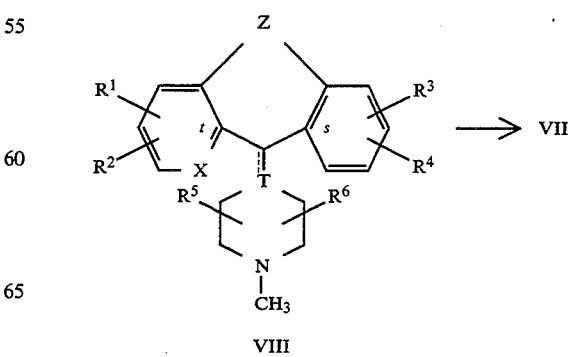

VIII

For example, the compound of Formula VIII can be reacted with the corresponding alkyl chloroformate in an inert solvent, such as toluene, at a suitable temperature (e.g., about 50° to about 100° C.) to form a compound of Formula VII.

It also will be apparent to one skilled in the art that there are other methods for converting a compound of Formula VIII to compound II. For example, treatment of a compound of Formula VIII with BrCN via von Braun reaction conditions would provide a nitrile of Formula IX as illustrated below. Subsequent hydrolysis of the nitrile IX under either aqueous basic or acidic conditions will produce a compound of Formula II. This method is preferable when there is substitution on the piperidine or piperazine ring.

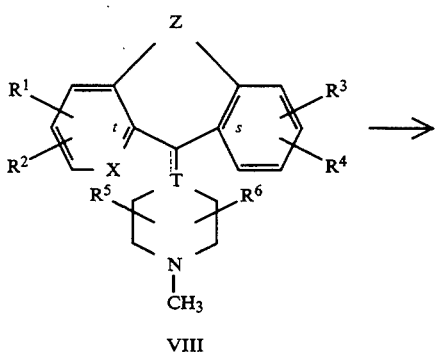

VIII

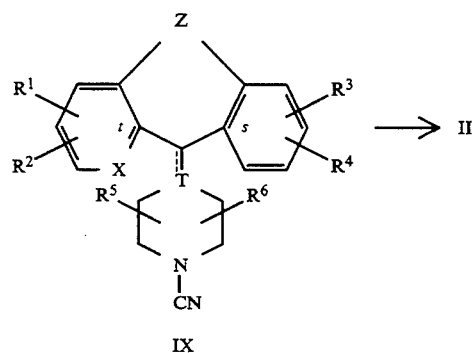

IX

PREPARATION OF COMPOUNDS OF FORMULAS II AND VIII WHEREIN Z REPRESENTS:

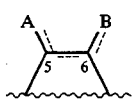

(A). COMPOUNDS OF FORMULA VIII WHEREIN X REPRESENTS NITROGEN (I.E., VIIIa).

The syntheses of compounds of the Formula VIIIa:

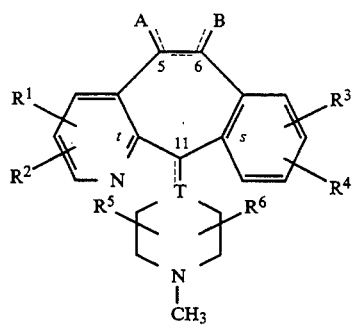

VIIIa have been previously described. They may be produced by one of several methods disclosed generally in U.S. Pat. No. 3,326,924; U.S. Pat. No. 3,357,986; U.S. Pat. No. 3,409,621; U.S. Pat. No. 3,419,565; U.S. Pat. No. 4,804,666; U.S. Pat. No. 4,826,853; WO 88/03138 and WO 90/13548. For example, WO 88/03138 discloses how to make the starting materials having either saturation or unsaturation in the 5-6 bridgehead position, having a double or single bond at the labelled 11-position of the tricyclic ring system, having piperazine groups attached at the 11-position of the tricyclic ring system, having substitution on the bridgehead carbon atoms 5 and/or 6, and having various $R^1$, $R^2$, $R^3$, and/or $R^4$ substituents on the tricyclic portion of the compounds of the invention. WO 90/13548 discloses how to make starting materials having the tricyclic ring N atom N-oxidized and/or having $R^1$ and/or $R^2$ substituents on the pyridine ring of the tricyclic ring system. Scheme I is illustrative of the process used to prepare compounds of the type VIIIa wherein X is nitrogen.

(B) COMPOUNDS OF FORMULA II WHEREIN X AND T REPRESENT NITROGEN (I.E., IIa).

In general, compounds of Formula II can be prepared as described above. However, the syntheses of compounds of Formula IIa (note: T=N)

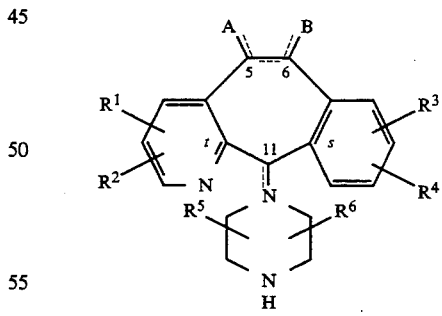

IIa are preferably prepared by different procedures known in the art—see for example, U.S. Pat. No. 3,409,621 and WO 88/03138. Scheme II is illustrative of the process used to prepare compounds of the type IIa wherein X and T are nitrogen.

(C) COMPOUNDS OF FORMULA II AND VIII WHEREIN X REPRESENTS CARBON (I.E., IIb and VIIIb).

The syntheses of compounds of Formulas IIb and VIIIb

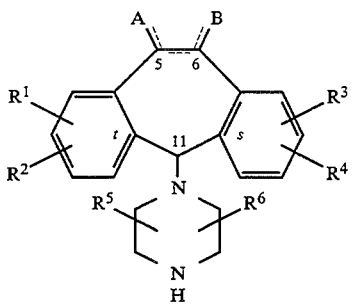

IIb

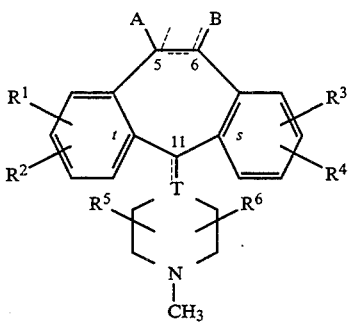

VIIIb have also been previously described—see for example, U.S. Pat. No. 3,014,991; the *Jour. of Med. Chem.* 8, 829 (1965); and the *Jour. of Org. Chem.*, 50, 339 (1985). In general, many of the methods utilized in the preparation of compounds of the type VIIIa and IIa can be used to prepare derivatives of the type VIIIb and IIb. For example, the piperazine derivatives (T=N) in the all carbon tricyclic series (X=CH) can be prepared via the alkylation sequence described for the preparation of the corresponding derivatives in the pyridine series (X=N) as described in U.S. Pat. No. 3,409,621 and WO 88/03138.

Illustrations of the routes discussed above are shown in Schemes III–V below in which A, B, $R^1$–$R^6$ and X are as defined above. In Scheme IV, the product of Formula VIII is saturated or unsaturated at the indicated 5,6-position depending upon which of the two reaction courses are used to reach Formula VIII.

PREPARATION OF COMPOUNDS OF THE FORMULA VIII WHEREIN Z REPRESENTS;

—$(C(R^a)_2)_m$—Y—$(C(R^a)_2)_n$—

(A) COMPOUNDS OF FORMULA VIII WHEREIN M PLUS N IS 0 AND Y REPRESENTS A DIRECT BOND (I.E., VIIIc)

The syntheses of compounds of Formula VIIIc

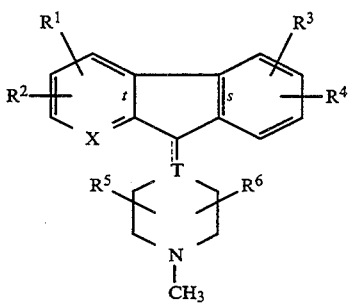

VIIc wherein m plus n is 0 and Y represents a direct bond have been previously described and are disclosed in WO 89/10369 for the cases wherein X is nitrogen. Scheme VI is illustrative of the process used to prepare compounds of the type VIIIc wherein X is nitrogen.

Those skilled in the art will recognize that compounds wherein X is carbon can also be prepared by the procedure disclosed in WO 89/10369. Scheme VII is illustrative of the process used to prepare compounds of the type VIIIc wherein X is carbon.

In general, compounds of Formula II wherein m plus n is 0 and Y represents a direct bond can be prepared as described above. However, the syntheses of compounds of Formula IIc

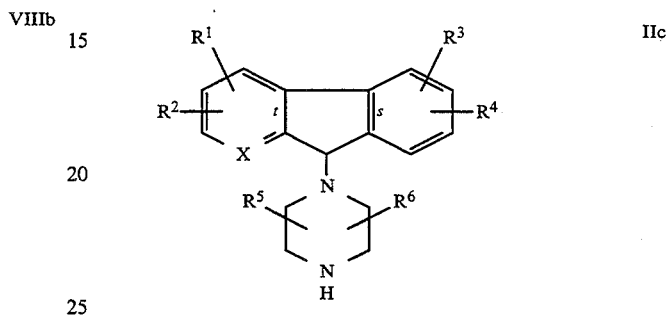

IIc (note: T is nitrogen) are preferably prepared by different procedures known in the art. For example, see: U.S. Pat. No. 3,409,621; WO 88/03138; and WO 89/10369. Scheme VIII is illustrative of the process used to prepare compounds of the type IIc wherein T is nitrogen.

(B) COMPOUNDS OF FORMULA VIII WHEREIN M PLUS N IS 0 AND Y REPRESENTS —O—, —S(O)$_e$—, OR —NR$^{11}$— (I.E., VIIId).

The syntheses of compounds of Formula VIIId

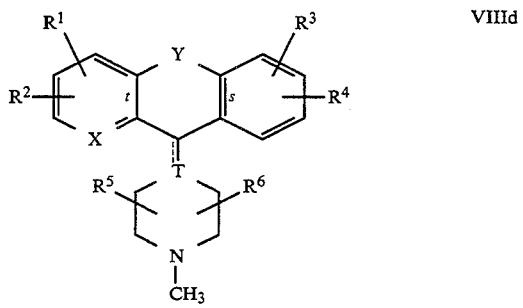

VIIId wherein m plus n is 0 and Y represents —O—, —S(O)$_e$—, or —NR$^{11}$— have been previously described for the cases wherein X is nitrogen—see, for example, WO 89/10369; U.S. Pat. No. 3,803,153; U.S. Pat. No. 3,803,154; and U.S. Pat. No. 3,325,501. Scheme IX is illustrative of the process used to prepare compounds of the type VIIId wherein X is nitrogen.

The syntheses of compounds of Formula VIIId wherein X is carbon are known in the art—see, for example, Collect. Czech. Chem. Comm. 54(5), 1388–1402, (1989); J. Med. Chem. 17, 57 (1974); U.S. Pat. No. 3,391,143; U.S. Pat. No. 4,021,561; U.S. Pat. No. 4,086,350; U.S. Pat. No. 4,616,023; West German Patent 1670334; BE 707523; BE 815078; BR 1,153,977; DT 2549841 and WO 87/07894. Scheme X is illustrative of the process used to prepare compounds of the type VIIId wherein X is carbon.

In general, compounds of Formula II wherein m plus n is 0 and Y represents —O—, —S(O)$_e$—, —NR$^{11}$— can be prepared as described above. However, the syntheses of compounds of Formula IId

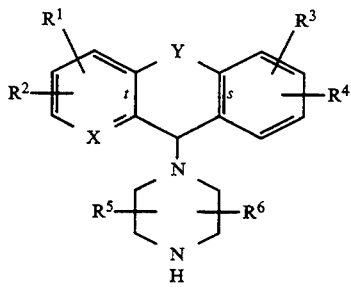

IId (note: T is nitrogen) are preferably prepared by different procedures known in the art. For example, see U.S. Pat. No. 3,157,658; U.S. Pat. No. 3,290,313; U.S. Pat. No. 3,350,402; U.S. Pat. No. 3,409,621; U.S. Pat. No. 4,826,853; WO 88/03138; and WO 89/10369. Scheme XI is illustrative of the process used to prepare compounds of the type IId wherein T is nitrogen.

(C) COMPOUNDS OF FORMULA VIII WHEREIN M PLUS N IS 1 AND Y REPRESENTS —O—, —S(O)$_e$—, OR, —NR$^{11}$— (I.E., VIIIe).

The syntheses of compounds of Formula VIIIe

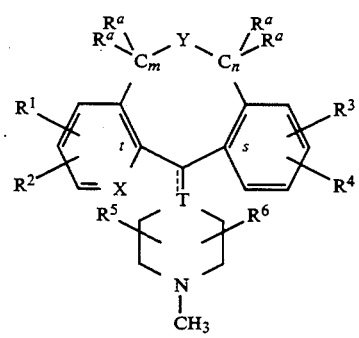

VIIIe wherein m plus n is 1 and Y represents —O—, —S(O)$_e$—, or —NR$^{11}$— are known and are disclosed, for example, in WO 89/10369 for the cases wherein X is nitrogen. Scheme XII is illustrative of the process used to prepare compounds of the type VIIIe wherein X is nitrogen.

The syntheses of compounds of Formula VIIIe wherein X is carbon are well known—see, for example, Collect. Czech. Chem. Comm. 54(5), 1388-1402, (1989); J. Med. Chem.17, 57 (1974); U.S. Pat. No. 3,267,094; U.S. Pat. No. 4,021,561; U.S. Pat. No. 4,086,350; U.S. Pat. No. 4,616,023; West German Patent 1670-334; BE 707523; BE 815078; FR 1,391,767 and WO 87/07894. In general, these compounds may also be prepared in a similar manner to compounds VIIIe wherein X is nitrogen. Scheme XIII is illustrative of the process used to prepare compounds of the type VIIIe wherein X is carbon.

In general, compounds of Formula II wherein m plus n is 1 and Y represents —O—, —S(O)$_e$—, or —NR$^{11}$— can be prepared as described above. However, the syntheses of compounds of Formula IIe

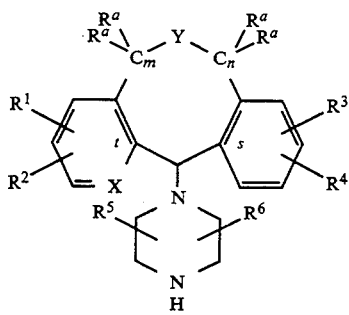

IIe (note: T is nitrogen) are preferably prepared by a different known in the art procedure. For example, see U.S. Pat. No. 3,409,621; DE 3906-920-A; WO 87/07894-A; WO 88/03138; and WO 89/10369. Scheme XIV is illustrative of the process used to prepare compounds of the type IIe wherein T is nitrogen.

(D) COMPOUNDS OF FORMULA VIII WHEREIN M PLUS N IS 3 AND Y REPRESENTS A DIRECT BOND (I.E., VIIIf).

The syntheses of compounds of the formula VIIIf

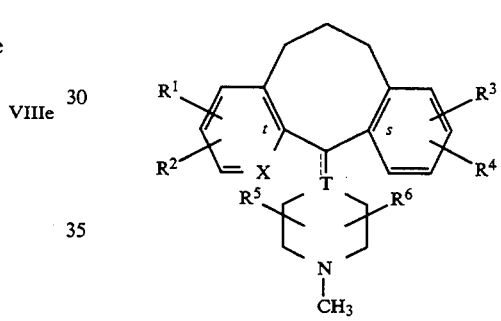

VIIIf wherein m plus n is 3 and Y represents a direct bond are known for the cases wherein X is nitrogen—see, for example, WO 89/10369. Scheme XV is illustrative of the process used to prepare compounds of the type VIIIf.

Those skilled in the art will appreciate that the procedures in WO 89/10369 can also be used to prepare compounds of Formula VIIIf wherein X is carbon.

In general, compounds of the formula II wherein m plus n is 3 and Y represents a direct bond may be prepared as described above. However, the syntheses of compounds of Formula IIf

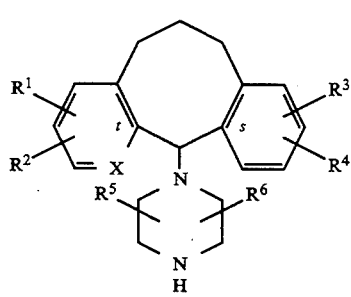

IIf (note: T is nitrogen) are preferably prepared by a different known in the art procedure. For example, see U.S. Pat. No. 3,409,621; WO 88/03138; and WO 89/10369.

Scheme XVI is illustrative of the process used to prepare compounds of the type IIf.

Those skilled in the art will appreciate that many of the substituents ($R^1$–$R^9$, A, and B) present in the various intermediates of the synthetic sequences described above can be used to generate different substituents by methods known to those skilled in the art. For example, a ketone can be converted to a thioketone via its treatment with $P_2S_5$ or Lawesson's reagent. These reagents introduce sulfur in place of oxygen. The reaction may take place at room or higher temperatures in pyridine, toluene or other suitable solvents. A ketone can also be converted to an alkyl or aryl group. This is accomplished via treatment of the ketone with a Wittig reagent or other organometalic species (e.g. Grignard reagent) to produce the corresponding olefin or alcohol, respectively. These derivatives in turn can be converted to the alkyl or aryl compounds.

In the above processes, in accordance with procedures well known to those skilled in the art, it is sometimes desirable and/or necessary to protect certain of the substituent groups, e.g., $R^1$, $R^2$, $R^3$, $R^4$, $R^5$, $R^6$, $R^7$, $R^8$, and $R^9$, during the reactions. Conventional protecting groups are operable as described in Greene, T. W., "Protective Groups In Organic Synthesis," John Wiley & Sons, New York, 1981; the disclosure of which is incorporated herein by reference thereto. For example, the groups listed in column 1 of Table 1 below may be protected as indicated in column 2 of Table 1:

TABLE 1
PROTECTED GROUPS

| 1. GROUP TO BE PROTECTED | 2. PROTECTED GROUP |
|---|---|
| —COOH | —COOalkyl, —COObenzyl, —COOphenyl, ![structure] |
| >NH | >NCOalkyl, >NCObenzyl, >NCOphenyl |
| >CO | ![cyclic ketal structures] |
| —OH | —O-(tetrahydropyranyl), —OCH₂phenyl, —OCH₃ OSi(CH₃)₂(t-Bu), |
| —NHR, wherein R is any substituent on an amino group within the scope of the claims | —N-(tetrahydropyranyl), —NR—CO—CF₃, —NRCOCH₃, —NRCH₂phenyl |
| —NH₂ | ![succinimide structure], —NH—C(O)—O(t-Bu) |

Other protecting groups well known in the art may also be used. After the reaction or reactions, the protecting groups may be removed by standard procedures.

SCHEME I

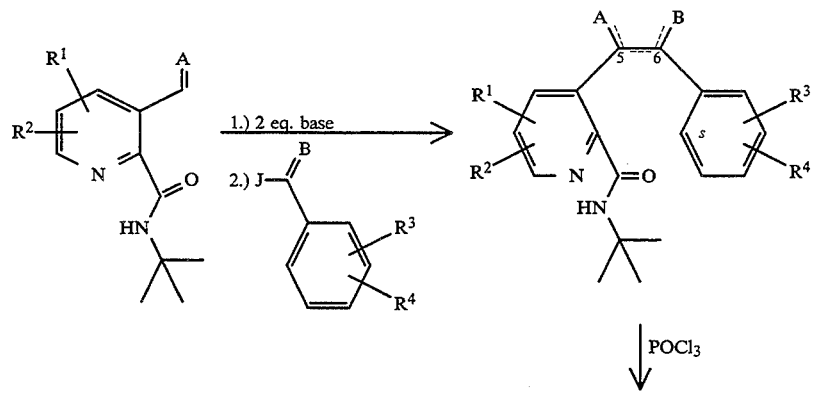

SCHEME I -continued
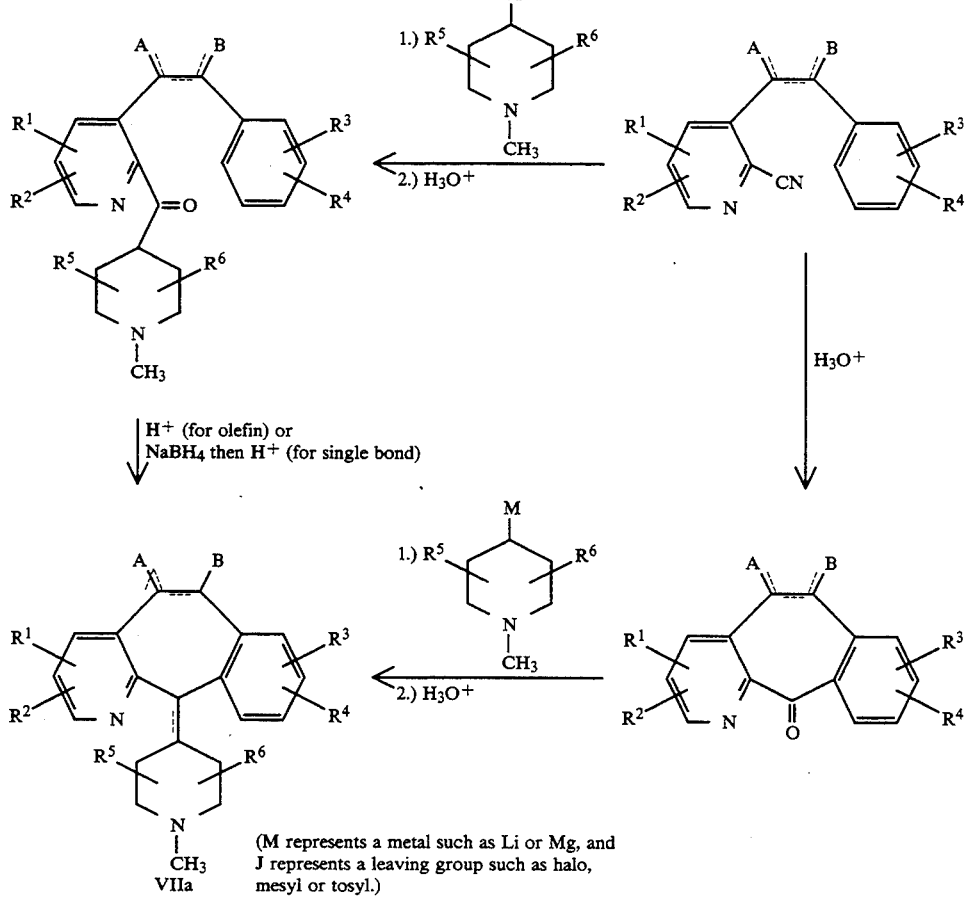
(M represents a metal such as Li or Mg, and J represents a leaving group such as halo, mesyl or tosyl.)
SCHEME II
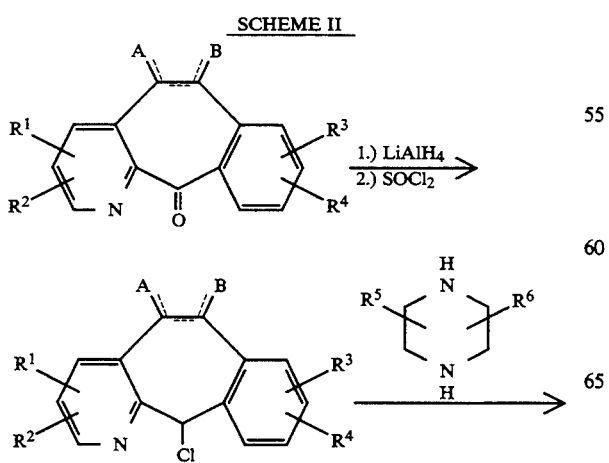
-continued
SCHEME II
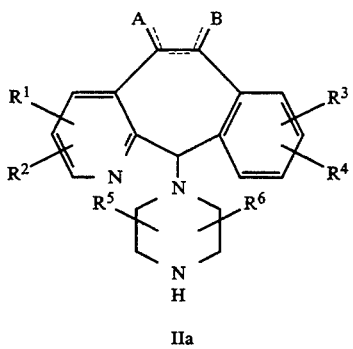

SCHEME III
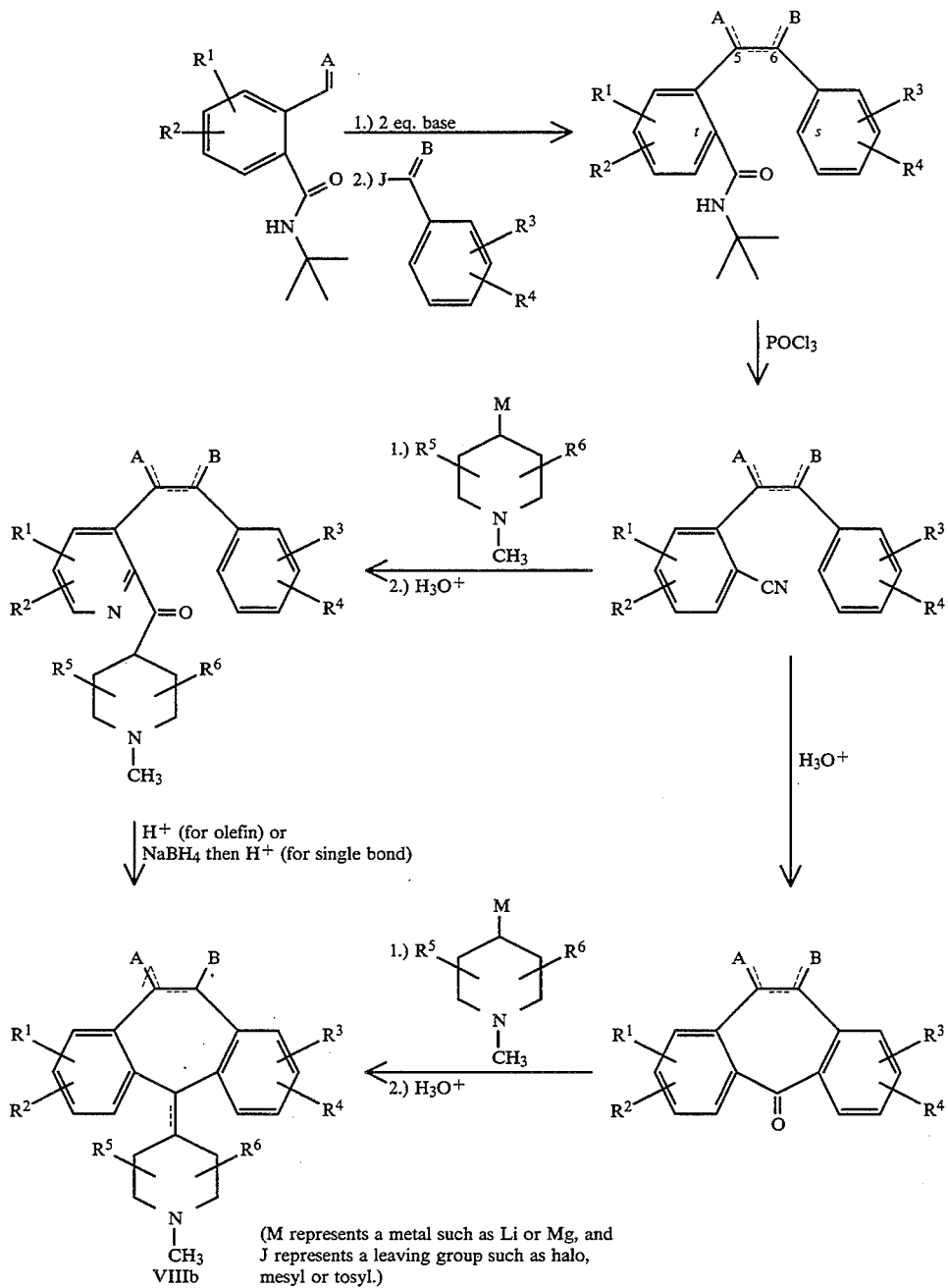
SCHEME IV
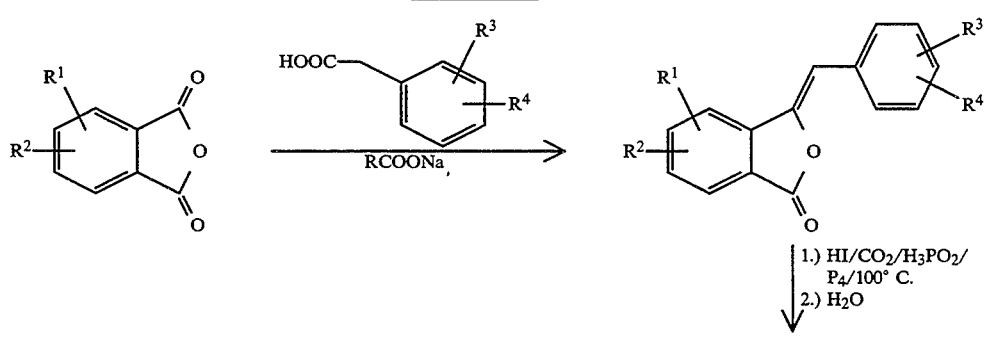

5,422,351
-continued
SCHEME IV
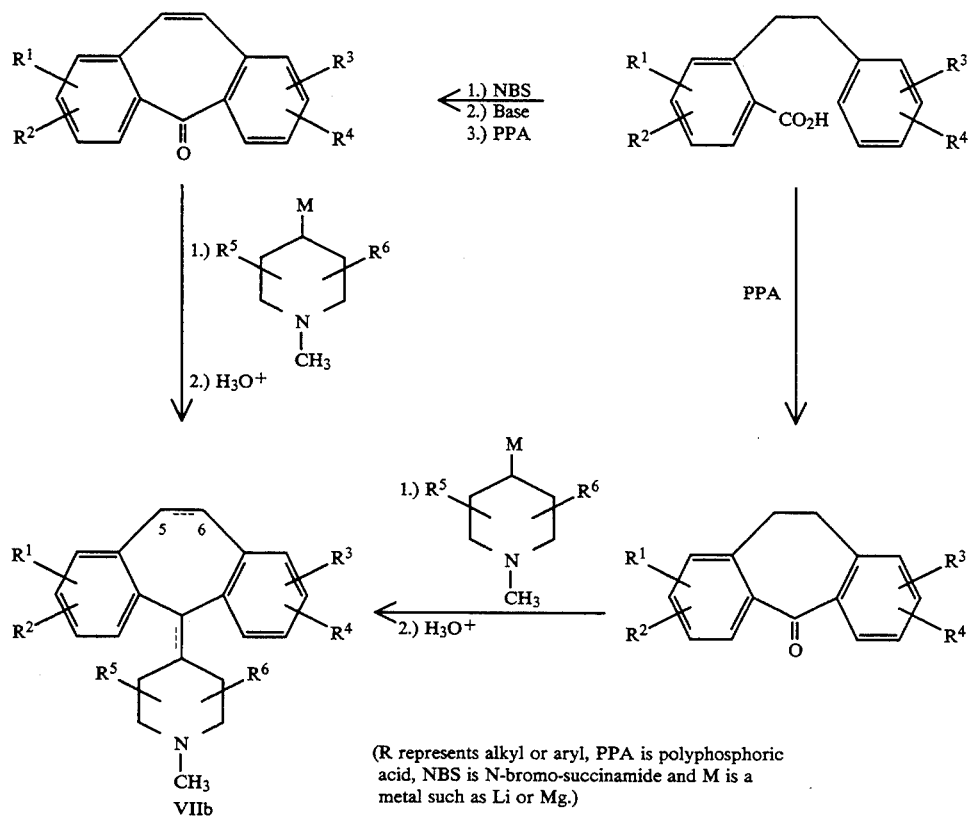
(R represents alkyl or aryl, PPA is polyphosphoric acid, NBS is N-bromo-succinamide and M is a metal such as Li or Mg.)
SCHEME V
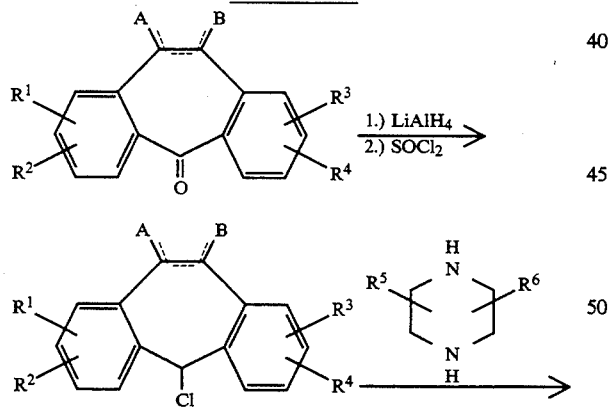
-continued
SCHEME V
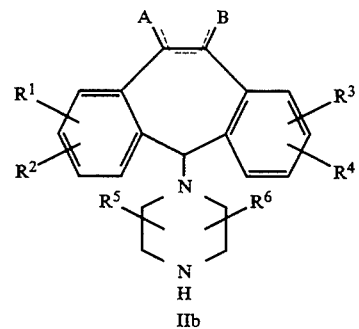
SCHEME VI
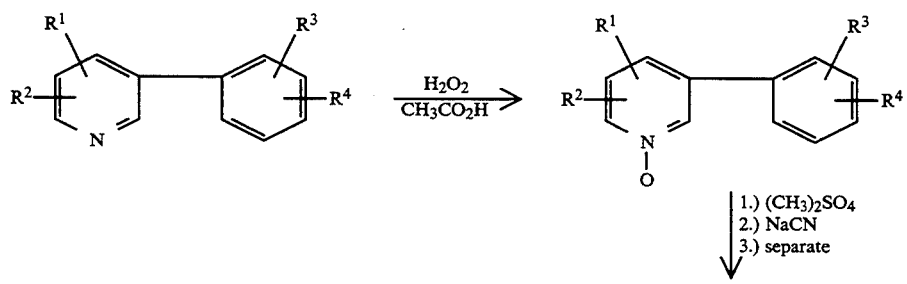

-continued
SCHEME VI
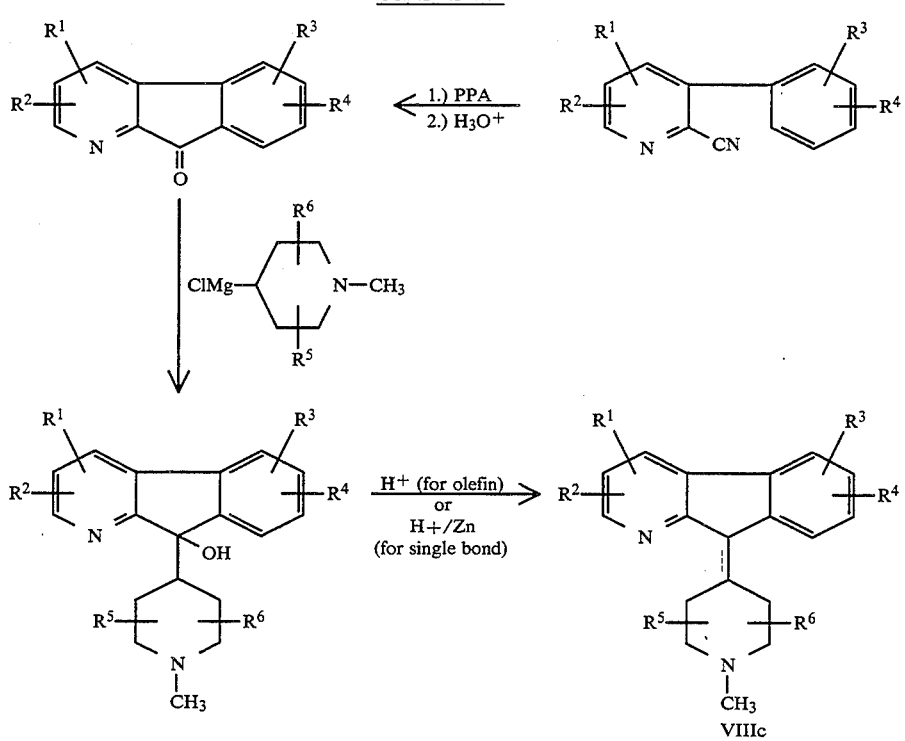
SCHEME VII
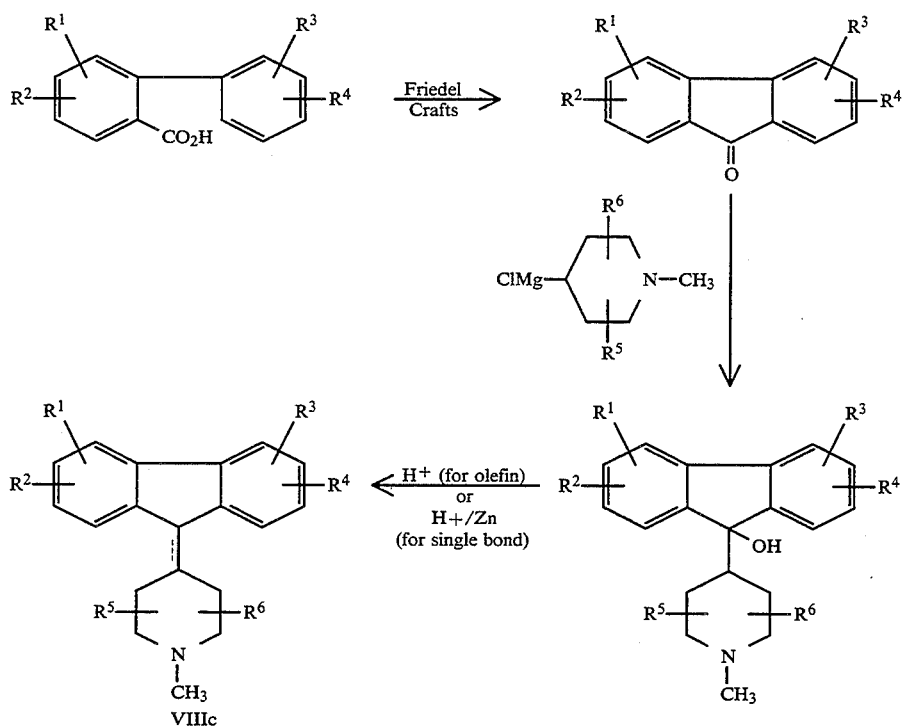

SCHEME VIII
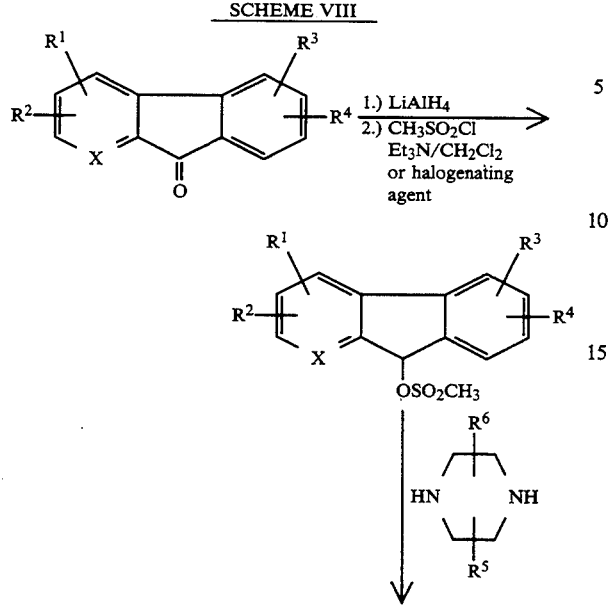
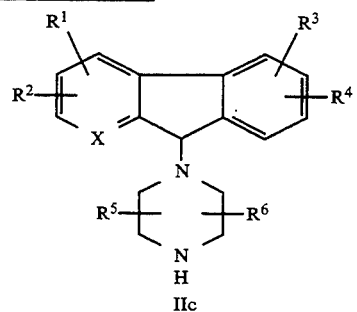
SCHEME IX
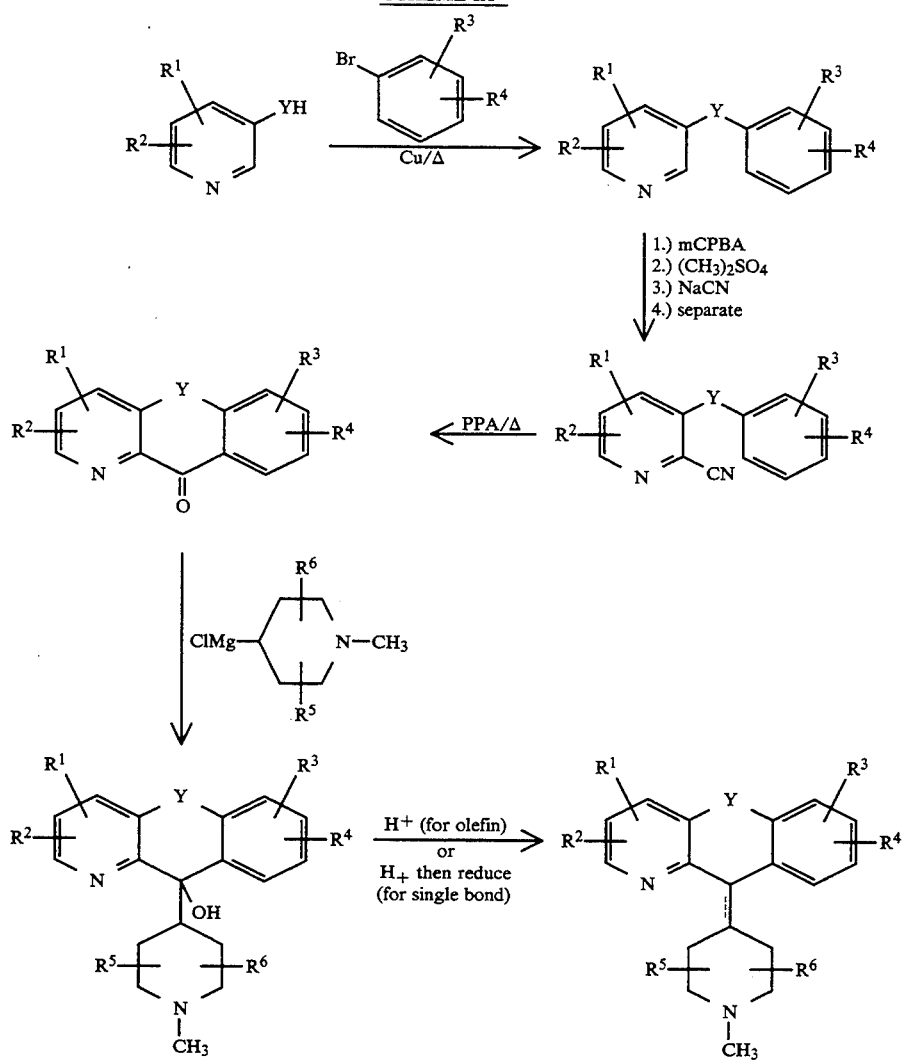

SCHEME X
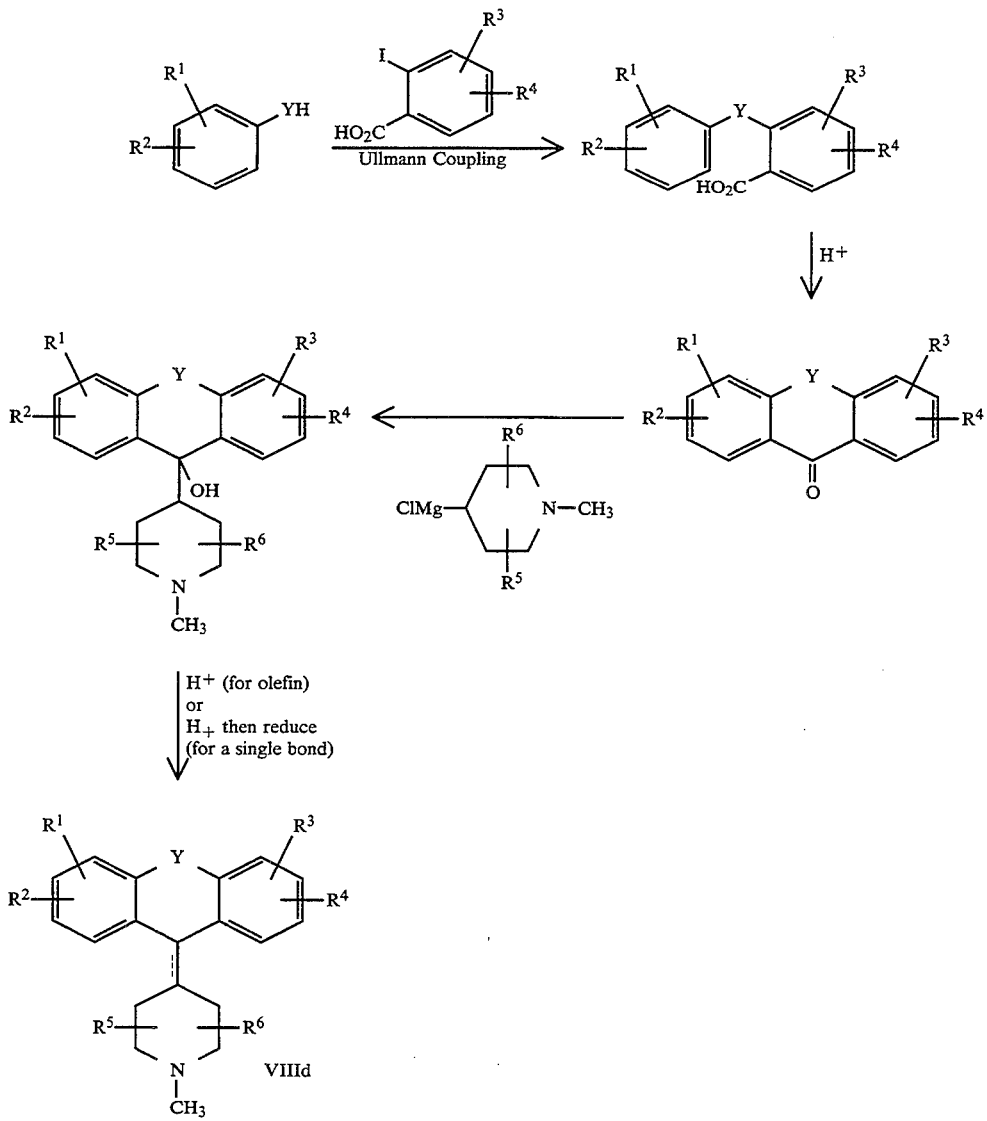
SCHEME XI
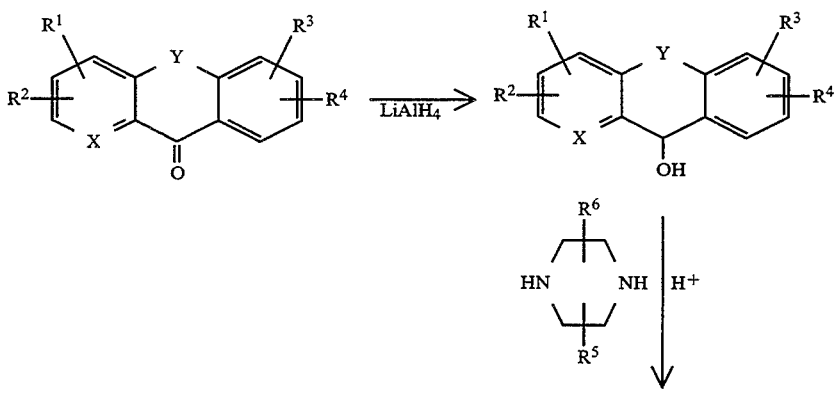

-continued
SCHEME XI
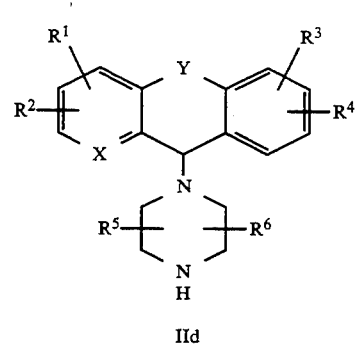
IId
SCHEME XII
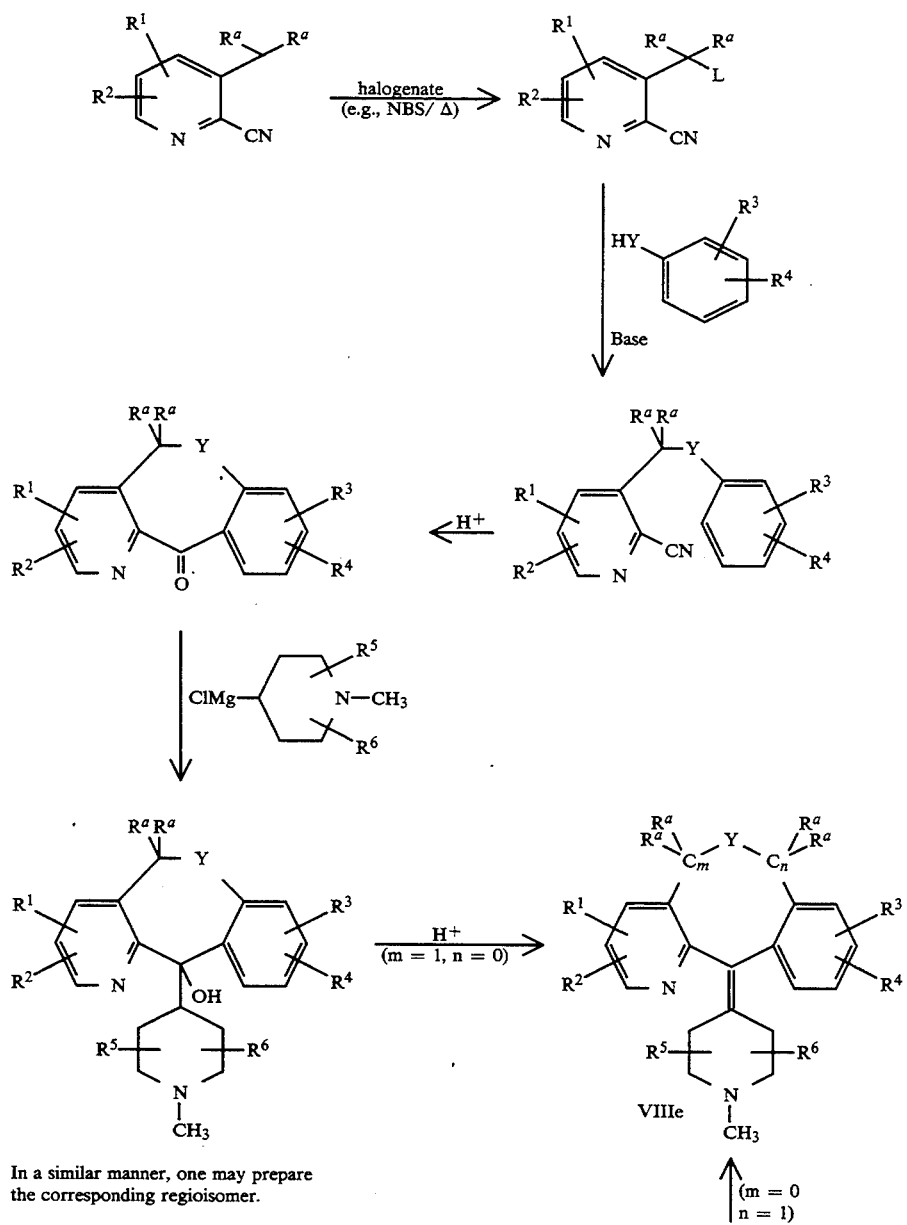
In a similar manner, one may prepare the corresponding regioisomer.

-continued
SCHEME XII
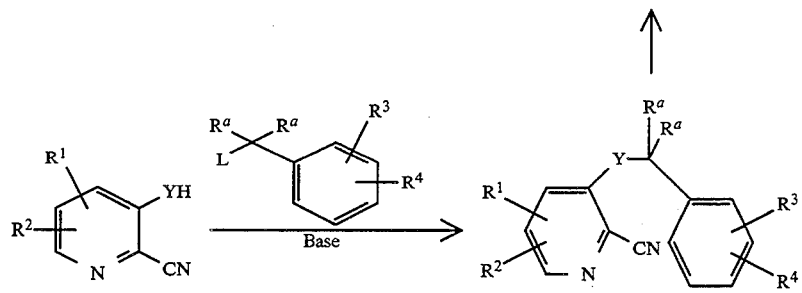
SCHEME XIII
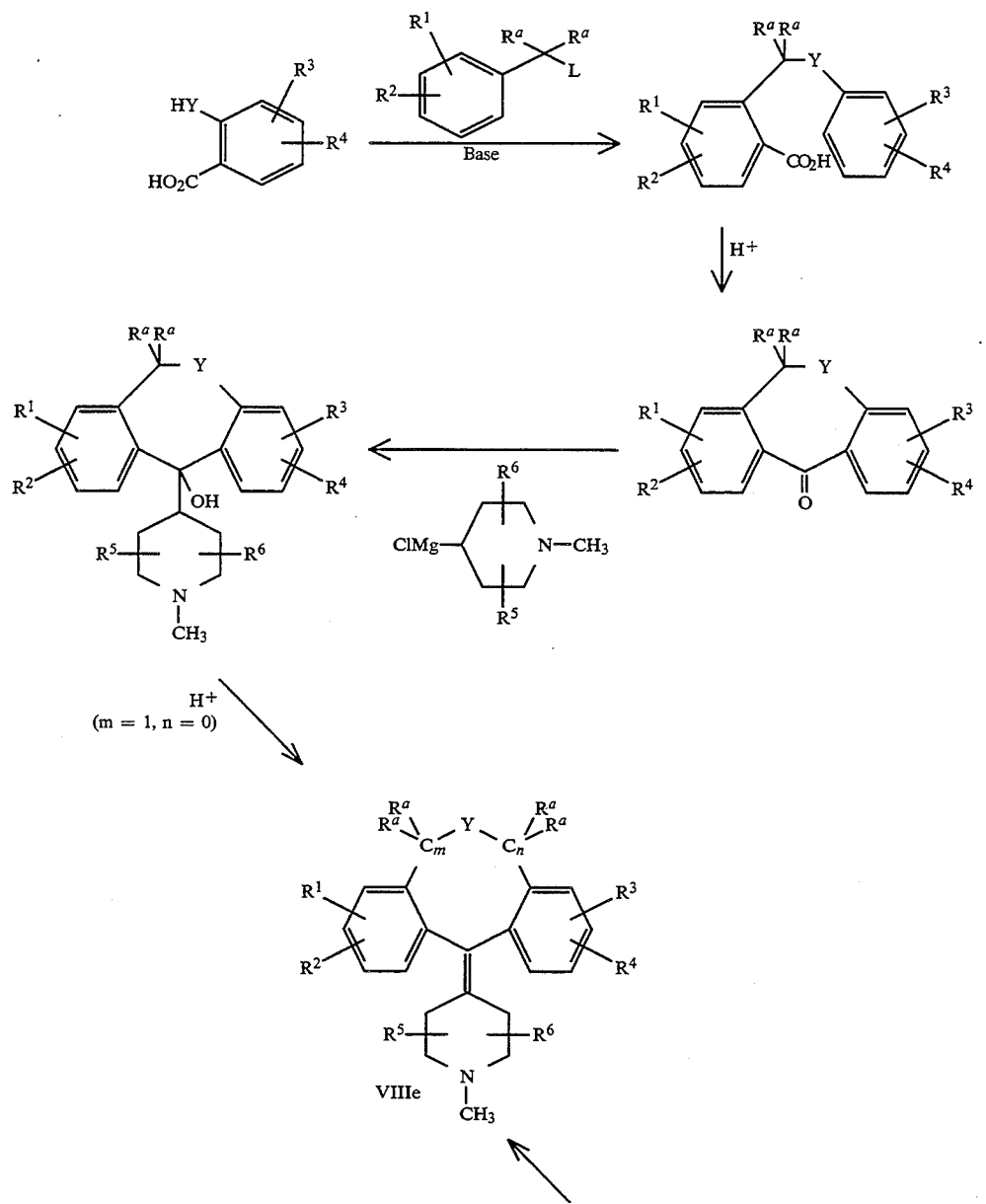

SCHEME XIII
In a similar manner, one may prepare the corresponding regioisomer.
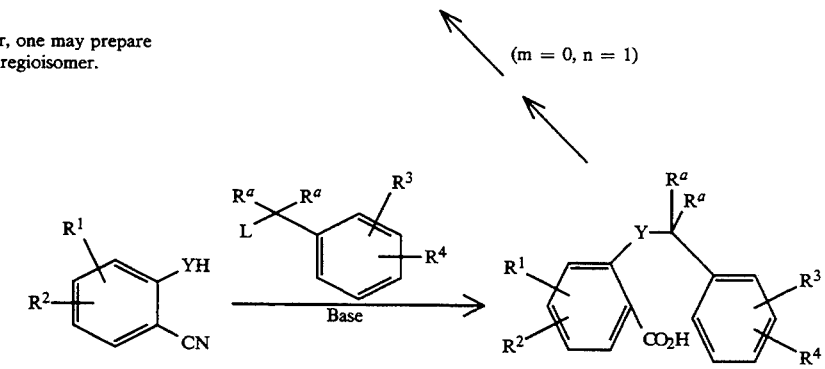
(m = 0, n = 1)
SCHEME XIV
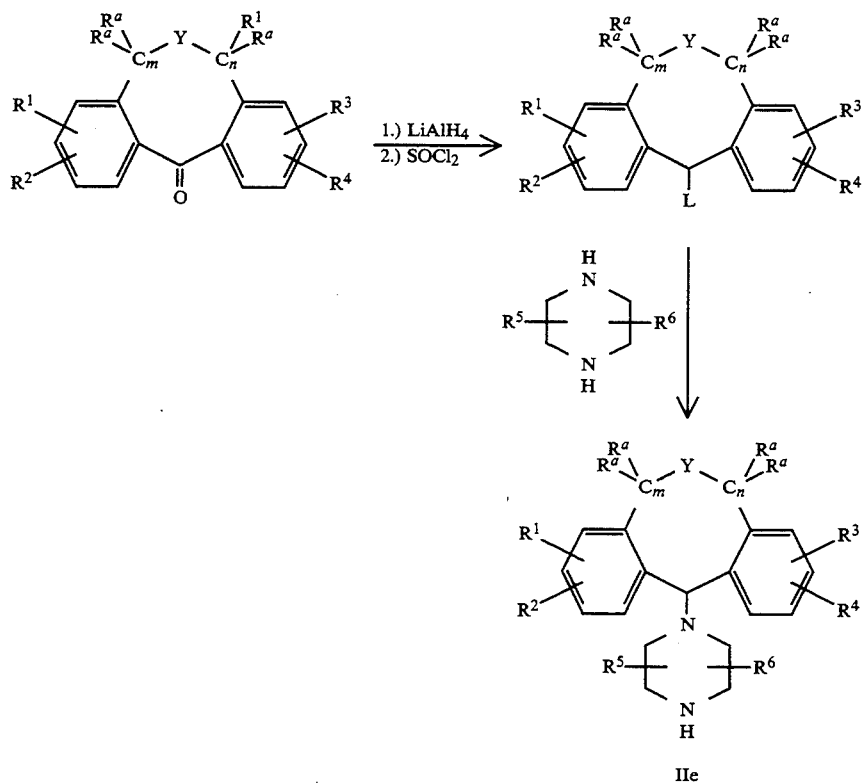
SCHEME XV
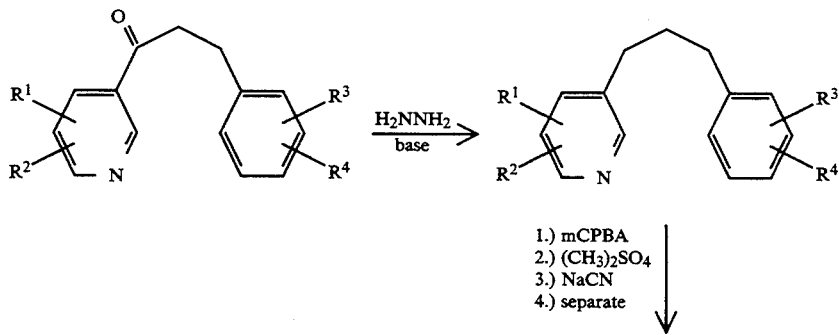
1.) mCPBA
2.) (CH$_3$)$_2$SO$_4$
3.) NaCN
4.) separate

SCHEME XV -continued

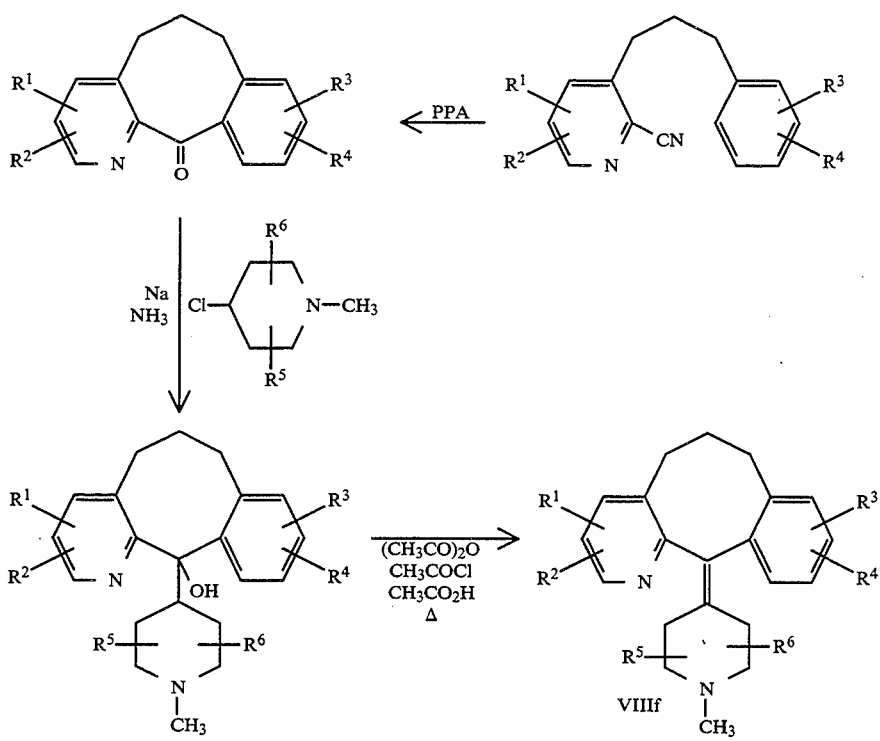

SCHEME XVI

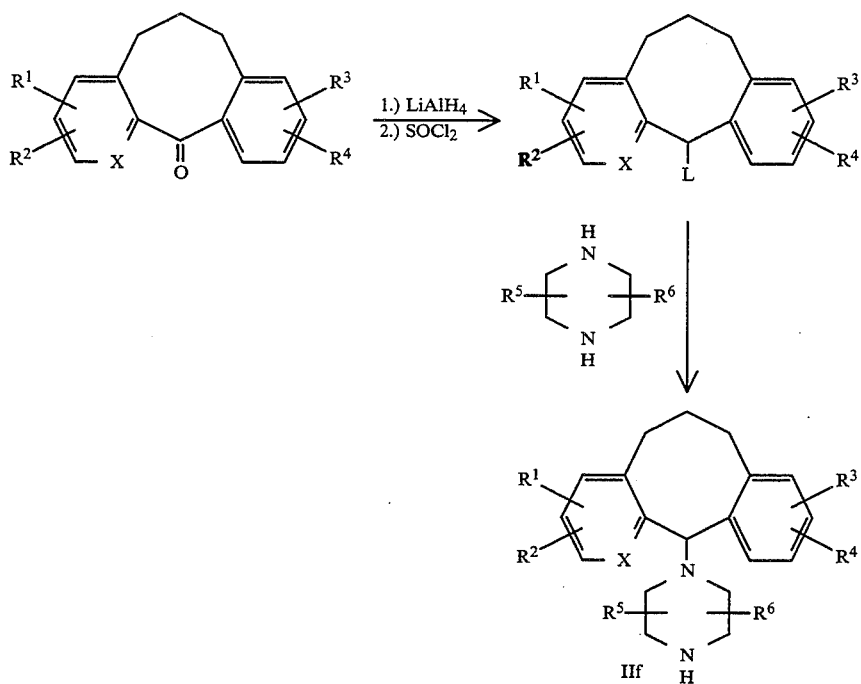

The compounds of the invention possess platelet-activating factor ("PAF") and histamine antagonistic properties. The compounds of the invention are, therefore, useful when PAF and/or histamine are factors in the disease or disorder. This includes allergic diseases such as asthma, allergic rhinitis, adult respiratory distress syndrome, urticaria and inflammatory diseases such as rheumatoid arthritis and osteo-arthritis. For example, PAF is an important mediator of such processes as platelet aggregation, smooth muscle contraction (especially in lung tissue), eosinophil chemotxis, vascular permeability and neutrophil activation. Recent evidence implicates PAF as an underlying factor involved in airway hyperreactivity.

The PAF antagonistic properties of these compounds may be demonstrated by use of standard pharmacological testing procedures as described below. These test procedures are standard tests used to determine PAF antagonistic activity and to evaluate the usefulness of said compounds for counteracting the biological effects of PAF. The in vitro assay is a simple screening test, while the in vivo test mimics clinical use of PAF antagonists to provide data which simulates clinical use of the compounds described herein.

A. In Vitro Studies

Platelet Aggregation Assay

Platelet-activating factor (PAF) causes aggregation of platelets by a receptor-mediated mechanism. Therefore, PAF-induced platelet aggregation provides a simple and convenient assay to screen compounds for PAF antagonism.

Human blood (50 ml) was collected from healthy male donors in an anticoagulant solution (5 ml) containing sodium citrate (3.8%) and dextrose (2%). Blood was centrifuged at 110× g for 15 min. and the supernatant platelet-rich plasma (PRP) carefully transferred into a polypropylene tube. Platelet-poor-plasma (PPP) was prepared by centrifuging PRP at 12,000× g for 2 min. (Beckman Microfuge B). PRP was used within 3 hr. of drawing the blood.

PAF was dissolved in chloroform:methanol (1:1, v/v) at a concentration of 2 mg/ml and stored at $-70°$ C. An aliquot of this solution was transferred to a polypropylene tube and dried under a flow of nitrogen gas. To the dried sample was added Hepes-saline-BSA (BSA=bovine serum albumen) buffer (25 mM Hepes, pH 7.4, 1254 mM NaCl, 0.7 mM $MgCl_2$ and 0.1% BSA) to obtain a 1 mM solution and sonicated for 5 min. in a bath sonicator. This stock solution was further diluted to appropriate concentrations in Hepes-saline-BSA buffer. Collagen (Sigma) and adenosine diphosphate (ADP) (Sigma) were purchased as solutions. Test compounds were initially dissolved in dimethyl sulfoxide (DMSO) at a concentration of 50 mM and then further diluted in Hepes-saline-BSA buffer to achieve appropriate concentrations.

When an aggregating agent such as PAF is added to PRP, platelets aggregate. An aggregometer quantifies this aggregation by measuring and comparing light (infra-red) transmission through PPP and PRP. Aggregation assays were performed using a dual-channel aggregometer (Model 440, Chrono-Log Corp., Havertown, Pa.). PRP (0.45 ml) in aggregometer cuvettes was continually stirred (37° C.). Solutions (50 μL) of test compounds or vehicel were added to the PRP and, after incubation for 2 min., 10–15 μl aliquots of PAF solution were added to achieve a final concentration of $1-5\times10^{-8}M$. In different experiments the aggregatory response was kept within a set limit by varying the concentration of PAF. Incubations were continued until the increase in light transmission reached a maximum (usually 2 min.). This increase in light transmission reflecting platlet aggregation is transmitted to a computer by the Chrono-Log model 810 AGGRO/LINK interface. The AGGRO/LINK calculates the slope of transmission change, thus providing the rate of aggregation. Values for inhibition were calculated by comparing rates of aggregation obtained in the absence and the presence of the compound. For each experiment, a standard PAF antagonist such as 8-chloro-6,11-dihydro-11-(1-acetyl-4-piperidylidene)-5H-benzo[5,6]cyclohepta[1,2-b]pyridine was used as a positive control.

Compounds that inhibit PAF-induced aggregation were tested against several other aggregating agents including collagen (0.2 mg/ml) and ADP (2 μM). Compounds showing no activity against these latter agents were considered to be specific PAF antagonists. Results are shown in TABLE 2 below.

B. In Vivo Studies: Agonist-Induced Responses

Spasmogen-Induced Bronchospasm in Guinea Pigs

Male Hartley guinea pigs (450–550 g) were obtained from Charles River Breeding Laboratories. The animals were fasted overnight and the following day were anesthetized with 0.9 ml/kg i.p. of dialurethane (containing 0.1 g/ml diallylbarbituric acid, 0.4 g/ml ethylurea and 0.4 g/ml urethane). The left jugular vein was cannulated for the administration of compounds. The trachea was cannulated and the animals were ventilated by a rodent respirator at 55 strokes/min. with a stroke volume of 4 ml. A side arm to the tracheal cannula was connected to a pressure transducer to obtain a continuous measure of inflation pressure. Bronchoconstriction was measured as the percent increase in inflation pressure that peaked within 5 min. after challenge with spasmogen. The animals were challenged i.v. with either histamine (10 ug/kg), methacholine (10 μg/kg), 5-hydroxytryptamine (10 μg/kg), or PAF (0.4 μg/kg in isotonic saline containing 0.25% BSA). Each animal was challenged with only a single spasmogen. The effect of a compound on the bronchospasm is expressed as a percent inhibition of the increase in inflation pressure compared to the increase in a control group. Results are shown in TABLE 2 below.

In TABLE 2 "CMPD NO." stands for "Compound Number" and the numbers in the CMPD NO. column refer to the following compounds:

(A) Compound Number 1 represents

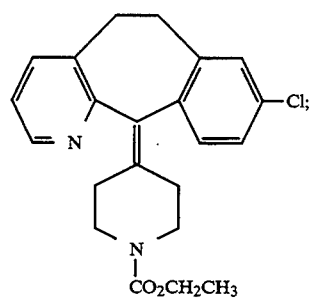

(B) Compound Number 2 represents

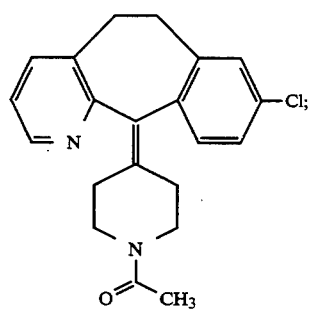

(C) Compound Number 3 represents

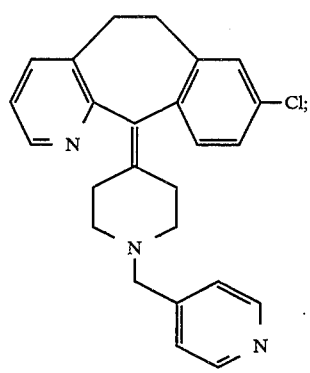
(D) Compound Number 4 represents
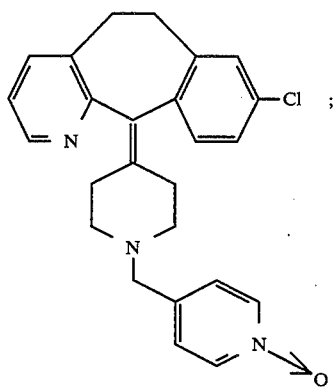
(E) Compound Number 5 represents
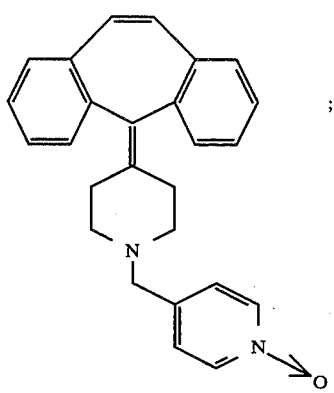
(F) Compound Number 6 represents
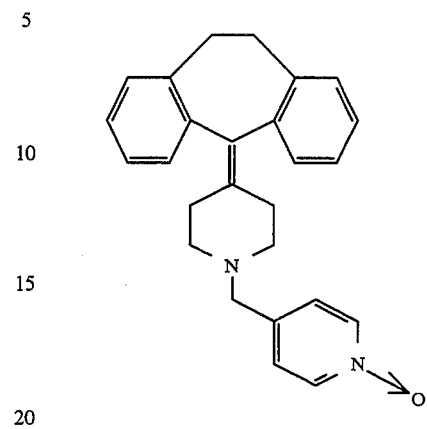
(G) Compound Number 7 represents
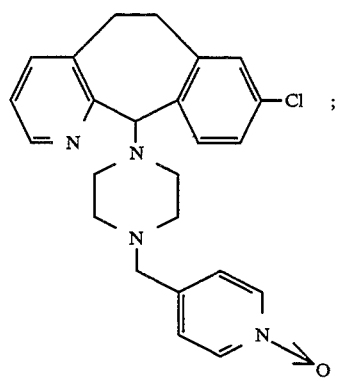
(H) Compound Number 8 represents
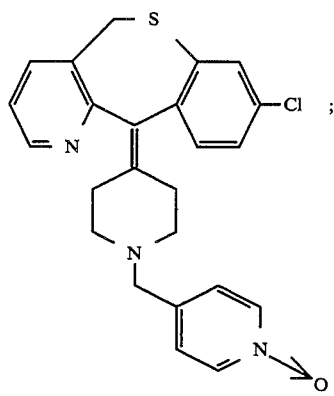
(I) Compound Number 9 represents

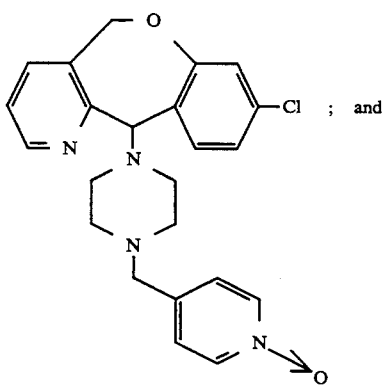

; and (J) Compound Number 10 represents

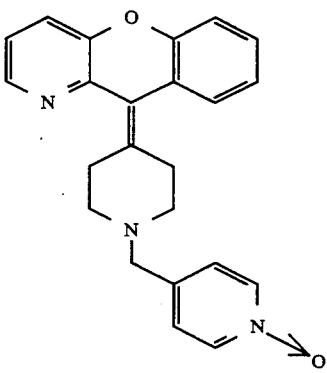

tories. The powders and tablets may be comprised of from about 5 to about 70 percent active ingredient. Suitable solid carriers are known in the art, e.g. magnesium carbonate, magnesium stearate, talc, sugar, lactose. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for parenteral injection.

Liquid form preparations may also include solutions for intranasal administration.

Aerosol preparations suitable for inhalation may include solutions and solids in powder form, which may be in combination with a pharmaceutically acceptable carrier, such as an inert compressed gas.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

TABLE 2

| CMPD NO | PAF Antagonism (in vitro) IC$_{50}$ ($\mu$M) | Agonist Bronchospasm (in Vivo)-oral | | | |
|---|---|---|---|---|---|
| | | PAF | | Histamine | |
| | | Dose | % Inhibition | Dose | % Inhibition |
| 1 | 175 | 10 mg/kg | <50 | 1 mg/kg | >50 |
| 2 | 0.61 | 5 mg/kg | 59 | 3 mg/kg | 49 |
| 3 | 7.3 | 3 mg/kg | 32 | — | — |
| 4 | 4.1 | 3 mg/kg | 35 | 1 mg/kg | 96 |
| 5 | 7.4 | 10 mg/kg | 15 | — | — |
| 6 | 3.4 | 3 mg/kg | 0 | — | — |
| 7 | 0.71 | 3 mg/kg | 81 | 3 mg/kg | 100 |
| 8 | 1.0 | 5 mg/kg | 67 | 1 mg/kg | 83 |
| 9 | 1.7 | 3 mg/kg | 22 | — | — |
| 10 | 8.1 | — | — | — | — |

As seen from the data of TABLE 2 above, the compounds of structural formula I exhibit PAF antagonist and antihistaminic properties to varying degrees, i.e., certain compounds have strong PAF antagonistic activity, but have weaker antihistaminic activity. Other compounds are strong antihistamines but weaker PAF antagonists. In general, compounds of this invention are stronger antihistamines than the previous dual PAF and histamine antagonists known in the art (cf: compound numbers 3-10 with 2). Several of the compounds are both strong PAF antagonists and potent antihistamines. Consequently, it is within the scope of this invention to use each of these compounds when clinically appropriate.

For preparing pharmaceutical compositions from the compounds described by this invention, inert, pharmaceutically acceptable carriers can be either solid or liquid. Solid form preparations include powders, tablets, dispersible granules, capsules, cachets and supposi- Preferably, the pharmaceutical preparation is in unit dosage form. In such form, the preparation is subdivided into unit doses containing appropriate quantities of the active component, e.g., an effective amount to achieve the desired purpose.

The quantity of active compound in a unit dose of preparation may be varied or adjusted from about 0.1 mg to 1000 mg, more preferably from about 1 mg. to 300 mg, according to the particular application. The appropriate dosage can be determined by comparing the activity of the compound with the activity of a known antihistaminic compound such as 8-chloro-6,11-dihydro-11-(1-ethoxycarbonyl-4-piperidylidene)-5H-benzo[5,6]cyclohepta[1,2-b]pyridine, which compound is disclosed in U.S. Pat. No. 4,282,233.

The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The amount and frequency of administration of the compounds of the invention and the pharmaceutically acceptable salts thereof will be regulated according to the judgment of the attending clinician considering such factors as age, condition and size of the patient as well as severity of the symptoms being treated. A typical recommended dosage regimen is oral administration of from 10 mg to 1500 mg/day preferably 10 to 1000 mg/day, in two to four divided doses to achieve relief of the symptoms. The compounds are non-toxic when administered within this dosage range.

The invention disclosed herein is exemplified by the following preparative examples, which should not be construed to limit the scope of the disclosure. Alternative mechanistic pathways and analogous structures within the scope of the invention may be apparent to those skilled in the art.

PREPARATIVE EXAMPLE 1

A. N-(1,1-DIMETHYLETHYL)-3-METHYL-2-PYRIDINE CARBOXAMIDE

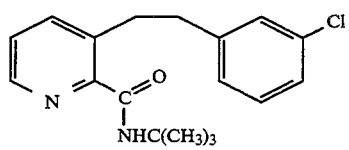

Suspend 2-cyano-3-methyl pyridine (400 g) in t-butanol (800 mL) and heat to 70° C. Add concentrated sulphuric acid (400 mL) dropwise over 45 minutes. Maintain the temperature at 75° C., until the reaction is complete, and for an additional 30 minutes. Dilute the mixture with water (400 mL), charge with toluene (600 mL) and bring to pH 10 with concentrated aqueous ammonia. Maintain the temperature at 50°–55° C. during the work up. Separate the toluene phase, and reextract the aqueous layer. Combine toluene phases and wash with water. Remove the toluene to yield the title compound N-(1,1-dimethylethyl)-3-methyl-2-pyridine carboxamide, as an oil, from which solid product is crystallized. (Yield 97%, as determined by an internal standard assay with gas chromatography).

B. 3-[2-(3-CHLOROPHENYL)ETHYL]-N-(1,1-DIMETHYLETHYL)-2-PYRIDINE CARBOXAMIDE

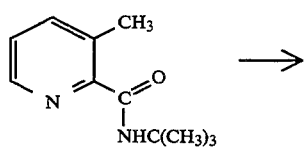

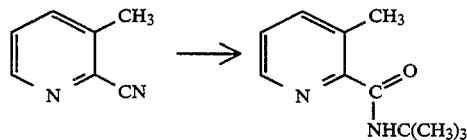

Dissolve the title compound of Preparative Example 1A, N-(1,1-dimethylethyl)-3-methyl-2-pyridine carboxamide (31.5 g.) in tetrahydrofuran (600 mL) and cool the resulting solution to −40° C. Add n-butyllithium (2 eq.) in hexane while maintaining the temperature at −40° C. The solution turns deep purple-red. Add sodium bromide (1.6 g) and stir the mixture. Add solution of m-chlorobenzylchloride (26.5 g., 0.174 mole) in tetrahydrofuran (125 mL) while maintaining the temperature at −40° C. Stir the reaction mixture until the reaction is complete as determined by thin layer chromatography. Add water to the reaction until the color is dissipated. Extract the reaction mixture with ethyl acetate, wash with water, and concentrate to a residue which is the title compound. (Yield 92% as shown by chromatography).

C. 3-[2-(3-CHLOROPHENYL)ETHYL]-2-PYRIDINE-CARBONITRILE

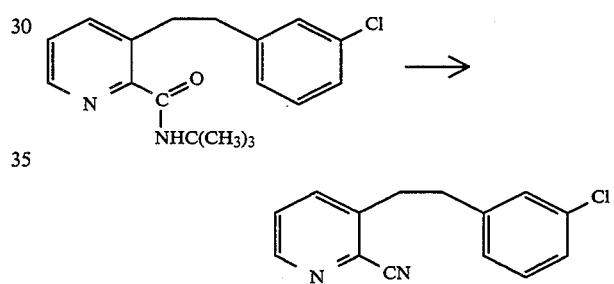

Heat a solution of the title compound of Preparative Example 1B, 3-[2-(3-chlorophenyl)ethyl]-N-(1,1-dimethylethyl)-2-pyridine carboxamide (175 g, 0.554 mole) in phosphorous oxychloride (525 mL, 863 g, 5.63 mole) and reflux for 3 hours. Determine completion of the reaction by thin layer chromatography. Remove any excess phosphorous oxychloride by distillation at reduced pressure and quench the reaction in a mixture of water and isopropanol. Bring to pH 5–7 by adding 50% aqueous sodium hydroxide solution while maintaining the temperature below 30° C. Filter the crystalline slurry of crude product and wash with water. Purify the crude product by slurrying the wet cake in hot isopropanol, and cool to 0°–5° C. Filter the product, wash with hexane and dry at a temperature below 50° C. to yield the title compound. (Yield: 118 g (HPLC purity 95.7%), m.p. 72° C.–73° C., 89.4% of theory).

D. 1-(METHYL-4-PIPERIDINYL)[3-(2-(3-CHLOROPHENYL)ETHYL)-2-PYRIDINYL]METHANONE HYDROCHLORIDE

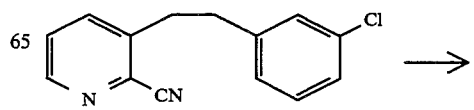

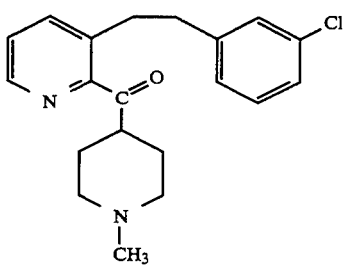

Dissolve the title compound of Preparative Example 1C, (118 g, 0.487 mole) in dry tetrahydrofuran (1.2 L) and add N-methylpiperidyl magnesium chloride (395 mL, 2.48 mole/liter, 0.585 mole, 1.2 eq.) over 15 minutes. Maintain the temperature at 40° C.–50° C. by cooling with water as necessary, for 30 minutes. Determine completion of the reaction by thin layer chromatography. Quench the reaction by reducing the pH to below 2 with 2N HCl and stir the resulting solution at 25° C. for 1 hour. Remove the bulk of the tetrahydrofuran by distillation and adjust the resulting solution to pH 3.5 by addition of aqueous sodium hydroxide. Cool to 0° to 5° C. and filter off the crystalline hydrochloride salt product. Wash with ice cold water and dry to constant weight at 60° C. to yield the title compound. (Yield: 168.2 g (HPLC purity 94%), m.p. 183°–185° C., 89% of theory).

E. 8-CHLORO-11-(1-METHYL-4-PIPERIDYLIDENE)-6,11-DIHYDRO-5H-BENZO[5,6]CYCLOHEPTA[1,2-b]PYRIDINE

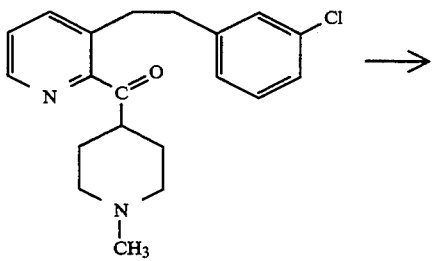

Dissolve the title compound of Preparative Example 1D above (59 g, 0.15 mole) in hydrofluoric acid (120 mL, 120 g, 6.0 mole) at −35° C. and add boron trifluoride (44.3 g, 0.66 mole) over 1 hour. Determine completeness of the reaction by thin layer chromatography. Quench the reaction using ice, water and potassium hydroxide bringing the solution to a final pH of 10. Extract the product with toluene and wash with water and brine. Concentrate the toluene solution to a residue, and dissolve in hot hexane. Remove the insolubles by filtration and concentrate the filtrate to yield the title compound as an off-white powder. (Yield: 45.7 g (HPLC purity: 95%), 92% of theory).

Alternative Step E: 8-CHLORO-11-(1-METHYL-4-PIPERIDYLIDENE)-6,11-DIHYDRO-5H-BENZO[5,6]CYCLOHEPTA[1,2-b]PYRIDINE React the title compound of Preparative Example 1D above (177 g, 0.49 mole) in trifluoromethanesulfonic acid (480 ml, 814.1 g, 5.31 mole) at 90°–95° C. for 18 hours under nitrogen. Determine the completeness of the reaction by thin layer chromatography. Cool the reaction and quench the reaction with ice-water and adjust the pH to 6 with barium carbonate. Extract the product with methylene chloride, and concentrate under reduced pressure to about 1 liter. Wash with water, and extract the product into 1N HCl which is treated with 30 g of activated charcoal, and filter through celite. Adjust the pH of the filtrate to 10 with aqueous sodium hydroxide (50%), extract the product into methylene chloride, and remove under reduced pressure to form a residue. Dissolve the residue in hot hexane, and filter to remove insolubles. Concentrate the filtrate to yield the title compound as a beige powder. (Yield: 126 g (HPLC purity 80%), 65% of theory).

F. 8-CHLORO-11-(1-ETHOXYCARBONYL-4-PIPERIDYLIDENE)-6,11-DIHYDRO-5H-BENZO[5,6]CYCLOHEPTA[1,2-b]PYRIDINE

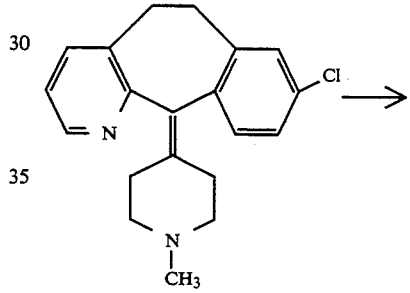

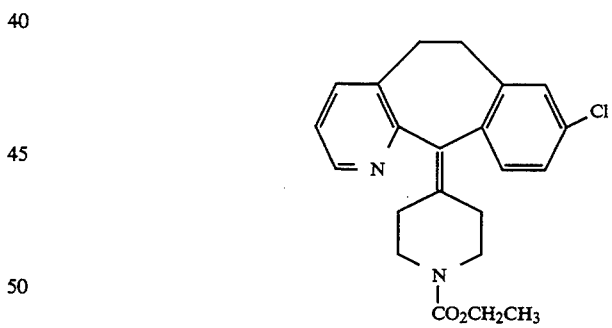

Dissolve the title compound of Preparative Example 1E above (45.6 g, 0.141 mole) in toluene (320 mL) at 80° C. and to it gradually add ethyl chloroformate (40.4 mL, 45.9 g, 0.423 mole). Following complete addition, maintain the temperature at 80° C. for 1 hour, then add diisopropylethylamine (2.7 mL, 2.00 g, 0.016 mole) and additional ethyl chloroformate (4.1 mL, 4.65 g, 0.0429 mole). Monitor completeness of the reaction by thin layer chromatography. Upon completion, cool the reaction mixture to ambient temperature, and wash the toluene solution with water. Concentrate the organic layer to a residue and dissolve in hot acetonitrile (320 mL). Decolorize the solution with 14 g of activated charcoal. Remove the activated charcoal by filtration and concentrate the filtrate to a crystalline slurry. Cool the mixture to 0°–5° C., and isolate the product by filtration.

Wash with cold acetonitrile and dry the product at below 70° C. to yield the title compound. (Yield: 42.4 g (HPLC purity 97.4%), 80% of theory).

G. 8-CHLORO-11-(4-PIPERIDYLIDENE)-6,11-DIHYDRO-5H-BENZO[5,6]CYCLOHEPTA[1,2-b]PYRIDINE

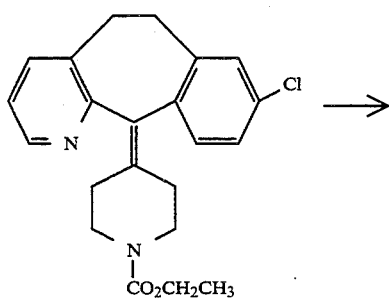

Hydrolize the title compound of Preparative Example 1F, 8-chloro-11-(1-ethoxycarbonyl-4-piperidylidene)-6,11-dihydro-5H-benzo[5,6]cyclohepta[1,2-b]pyridine (39 g, 0.101 mole) with KOH (50 g) in ethanol (305 mL) and water (270 mL) at reflux under an argon atmosphere for 64 hours. Partially distill off the ethanol and dilute the residue with brine, and extract with ethyl acetate (3×). Wash the combined organic phases with water and dry with $Na_2SO_4$. Remove the solvent to give a solid which can be recrystallized from toluene to give the title compound as a white solid. (Yield: 24.5 g, 77%, melting point 154°–155° C.).

H. By substituting in step 1B above, an appropriately substituted benzylic halide listed in TABLE 3 below for meta-chlorobenzylchloride, and employing basically the same methods as steps C through G, the products listed in TABLE 3 below are prepared. Reaction times are determined by TLC or HPLC. In some instances purification of the product by chromatography is necessary.

TABLE 3

Product of step G

| hadide | $R^3$ | $R^4$ | A | m.p. |
|---|---|---|---|---|
| 3-F-benzyl bromide | F | H | H | 133.5–134.5° C.[a] |
| 3,4-diCl-benzyl chloride | Cl | Cl | H | 150–152° C.[b] |
| 3-CH3-benzyl bromide | $CH_3$ | H | H | 142–144° C.[c] |
| 3-Br-benzyl bromide | Br | H | H | 146–148° C. |
| 3-OCH3-benzyl bromide | $OCH_3$ | H | H | crude solid |
| 2-naphthylmethyl bromide | $R^3$ & $R^4$ = fused benzo | | H | glass |
| CH3I - Then repeat step B with 3-Cl-benzyl bromide | Cl | H | $CH_3$ | glass |

[a]Step E required trifluoromethanesulfonic acid.
[b]Recrystallized from toluene.
[c]Recrystallized from acetone and pentane.

PREPARATIVE EXAMPLE 2

A. N-(1,1-DIMETHYLETHYL)-3-[2-(4-FLUOROPHENYL)ETHYL]-2-PYRIDINE CARBOXAMIDE

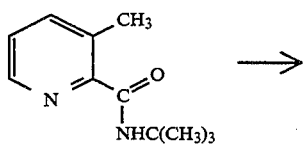

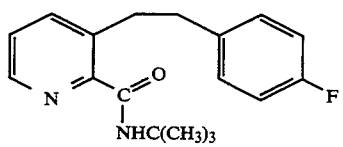

Cool a solution of N-(1,1-dimethylethyl)-3-methyl-2-pyridinecarboxamide (38.4 g, 0.2 mole) in dry THF (250 mL) to −40° C. and add n-butyl lithium (185 mL, 0.44 mole). Add sodium bromide (1.9 g, 18 mmol.) and stir for 15 minutes. Add 4-fluorobenzylchloride (31.8 g, 0.22 mole) and stir for 2.5 hours while warming to −5° C. Quench the reaction with water and extract the product twice with ethyl acetate, then wash with brine (2×). Dry the organic phase over Na₂SO₄, filter and remove the solvent to give the title compound. (60.0 g, Yield 99%, m.p. 59°–61° C.)

B.  3-[2-(4-FLUOROPHENYL)ETHYL]-2-PYRIDINE CARBONITRILE

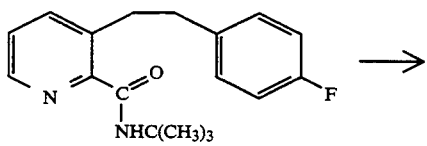

Heat the title compound of Preparative Example 2A above (60.0 g, 0.2 mole) in POCl₃ (200 mL) to 110° C. under an argon atmosphere for 3.5 hours. Pour the reaction mixture onto ice and basify with NaOH (50%) solution. Extract the mixture with ethyl acetate (3×) and wash with water. Wash with brine and dry over Na₂SO₄. Remove the solvent and pass the residue through a coarse SiO₂ (60–200 mesh) column to give the title compound as a white solid (40 g, Yield 88%, m.p. 48°–49° C.).

C.  9-FLUORO-5,6-DIHYDRO-11H-BENZO[5,6]-CYCLOHEPTA[1,2-b]PYRIDIN-11-ONE

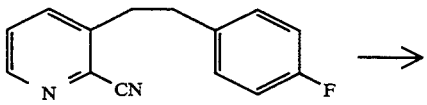

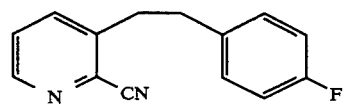

Cyclize the title compound of Preparative Example 2B above (31.5 g, 139 mmol) in polyphosphoric acid (1.24 kg) at 200° C. for 5.5 hours. Pour onto ice and basify with NaOH solution (50%). Extract the product with chloroform (3×) and wash with brine. Dry the organic phase with Na₂SO₄, filter and remove the solvent to give the title compound (20.4 g, yield 64%, m.p. 78°–81° C. after recrystallization from diisopropyl ether).

D.  9-FLUORO-11-(1-METHYL-4-PIPERIDINYL)-6,11-DIHYDRO-5H-BENZO[5,6]CYCLOHEPTA[1,2-b]PYRIDIN-11-OL

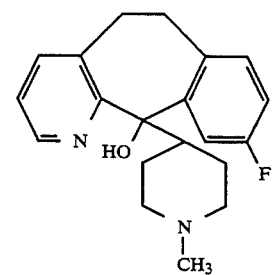

Dissolve the title compound of Preparative Example 2C above (10.0 g, 44 mmol) in THF (100 mL) and add slowly to a cooled (−40° C.) solution of the Grignard reagent prepared from N-methyl-4-chloropiperidine (57.9 mL, 88 mmol) and magnesium in THF (70 mL). Stir the mixture for about 1 hour while warming up to 0° C. Quench the reaction with NH₄Cl solution and extract with ethyl acetate (2×). Wash the organic phase with brine and dry over Na₂SO₄, filter and remove the solvent. Purify the residue with flash chromatography and elute with methanol (5%) in CHCl₃ to give the title compound as white granular crystals. (10.1 g, Yield 70%, m.p. 126°–127° C. after recrystallization from diisopropyl ether.)

E.  9-FLUORO-11-(1-METHYL-4-PIPERIDYLENE)-6,11-DIHYDRO-5H-BENZO[5,6-]CYCLOHEPTA[1,2-b]PYRIDINE

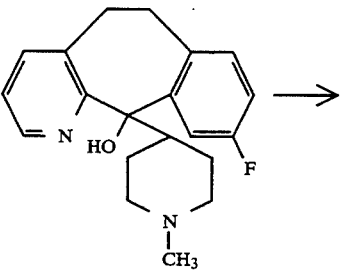

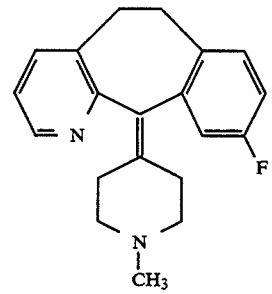

Add the title compound of Preparative Example 2D above (7.3 g, 22.3 mmol) to a mixture of cooled H₂SO₄ and CF₃SO₃H (1:1), (146 mL). Stir the reaction mixture for 0.5 hours at ice bath temperature and then at room temperature for 1.5 hours. Pour the reaction mixture onto ice and basify with NaOH (50%) solution. Extract the product with ethyl acetate (3×) and wash with brine. Dry the organic phase over Na₂SO₄, filter and remove the solvent to give a crude oil. Charcoal the oil and recrystallize from ethyl acetate and isopropyl ether to give the title compound. (5.6 g, Yield 82%, m.p. 134.5°–135.5° C.).

F. 9-FLUORO-11-(1-ETHOXYCARBONYL-4-PIPERIDYLIDENE)-6,11-DIHYDRO-5H-BENZO[5,6]CYCLOHEPTA[1,2-b]PYRIDINE

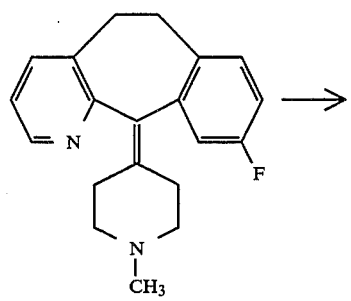

↓

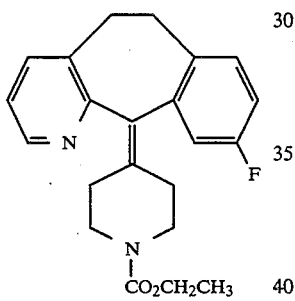

Stir a solution of the title compound of Preparative Example 2E above (5.0 g, 16.2 mmol) and triethylamine (2.6 g, 26 mmol) in dry toluene (60 mL) at 80° C. under an argon atmosphere, and add ethylchloroformate (9.8 g, 90 mmol) via a syringe. Stir the reaction at this temperature for 30 minutes and at room temperature for one hour. Filter the reaction and remove the solvent. Pass the residue through a coarse SiO₂ column (60–200 mesh), and elute with CHCl₃ to yield the title compound as a white solid. (4.5 g, Yield 76%, m.p. 112°–114° C. after trituration with pentane).

G. 9-FLUORO-11-(4-PIPERIDYLIDENE)-6,11-DIHYDRO-5H-BENZO[5,6]CYCLOHEPTA[1,2-b]PYRIDINE

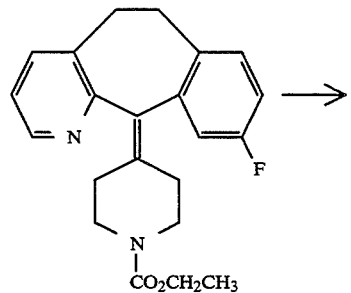

→

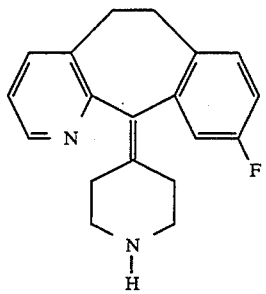

Reflux the title compound of Preparative Example 2F above (3.83 g, 10.4 mmol) with KOH (4.6 g) in 50 mL of ethanol/H₂O (1:1) for 4 hours under an argon atmosphere. Pour the reaction mixture into a brine solution and extract with ethyl acetate (2×), dry over Na₂SO₄ and filter. Remove the solvent to give the title compound (2.86 g, Yield 90%, m.p. 138°–140° C.).

H. By employing the appropriately substituted benzyl halide listed in Table 4 in place of 4-fluorobenzyl chloride in step 2A above, the desired products shown in the second column of TABLE 4 below are prepared by employing basically the same process as described in steps 2A–2G. Workup time is determined by either TLC or HPLC. In some instances purification of the product by chromatography is necessary.

TABLE 4

| halide | Product of step G | | |
|---|---|---|---|
| | R³ | R⁴ | m.p. |
| Br—CH₂—C₆H₄—Cl | H | Cl | 134–135° C.ᵃ |
| Cl—CH₂—C₆H₄—F | H | F | 138–140° C.ᵇ |
| Br—CH₂—C₆H₃(F)(F) | F | F | 120–122° C.ᵇ |

ᵃRecrystallized from ethyl acetate and pentane.
ᵇTriturated with pentane.

PREPARATIVE EXAMPLE 3

A. 8-CHLORO-11H-BENZO[5,6]CYCLOHEPTA[1,2-b]PYRIDIN-11-ONE

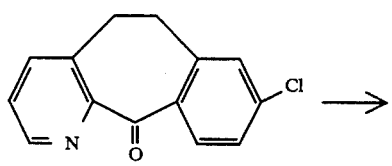

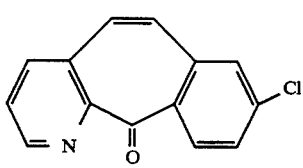

Reflux a mixture of 8-chloro-5,6-dihydro-11H-benzo[5,6]cyclohepta[1,2-b]pyridin-11-one (25.99 g, 0.107 mol.), recrystallized N-bromosuccinimide (21.35 g, 0.120 mol) and 167 mg (0.102 mmol) of azobisisobutyrylnitrile (AIBN) in 400 mL of carbon tetrachloride under an argon atmosphere for 1.25 hours. Cool the solution slowly to 50° C. and filter off the resultant precipitate.

Reflux the precipitate with 1,8-diazabicyclo[5.4.0]undec-7-ene (DBU) (20 mL, 0.134 mol) in $CH_2Cl_2$ (400 mL) for 1 hour. Wash with water (3×), dry over magnesium sulfate, filter and concentrate in vacuo. Recrystallize the crude product from $CH_2Cl_2$/toluene to give the title compound as colorless needles (8.93 g, yield 35%).

B.  8-CHLORO-11-(1-METHYL-4-PIPERIDINYL)-11H-BENZO[5,6]CYCLOHEPTA[1,2-b]PYRIDIN-11-OL

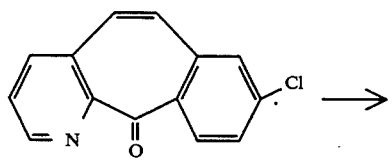

To a mixture of 22 mL of 0.5M Grignard reagent of N-methyl-4-chloropiperidine (11.0 mmole) in THF at 45° C. and under a nitrogen atmosphere was added dropwise over 15 min. a solution of 1.06 gm (4.39 mmole) of 8-chloro-11H-benzo[5,6]cyclohepta[1,2-b]pyridin-1-one in 23 mL of dry THF. After 2 hr. 40 min. the reaction mixture was poured into water and extracted three times with ethyl acetate (EtOAc). The organic portions were combined, washed two times with brine, dried over $MgSO_4$, filtered, and concentrated in vacuo. The residue was purified via flash chromatography [10% $CH_3OH$ in $CH_2Cl_2$] to give 970 mg (65%) of the title compound as a glass.

C.  8-CHLORO-11-(1-METHYL-4-PIPERIDILIDENE)-11H-BENZO[5,6]CYCLOHEPTA[1,2-b]PYRIDINE

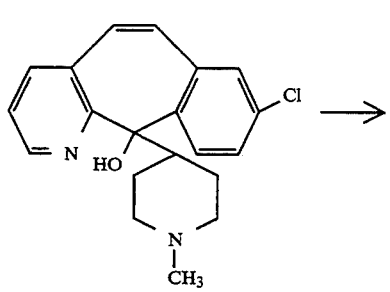

A mixture of 847 mg (2.48 mmole) of 8-chloro-11-(1-methyl-4-piperidinyl)-11H-benzo[5,6]cyclohepta[1,2-b]pyridin-11-ol in 5 mL of concentrated sulfuric acid and 5 mL of trifluoromethanesulfonic acid was heated at 70° C. for 4.1 hr. The mixture was cooled to room temperature, poured into ice cold 30% aqueous KOH, and extracted three times with $CH_2Cl_2$. The organic portions were combined, washed once with water, dried over $MgSO_4$, filtered, and concentrated in vacuo to yield 755 mg (94%) of the title compound as a glass.

D.  8-CHLORO-11-[1-(2,2,2-TRICHLOROETHOXYCARBONYL)-4-PIPERIDYLIDENE]-11H-BENZO[5,6]CYCLOHEPTA[1,2-b]PYRIDINE

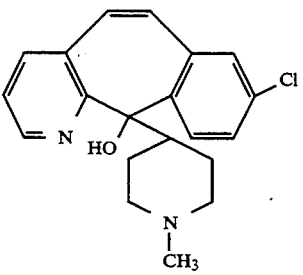

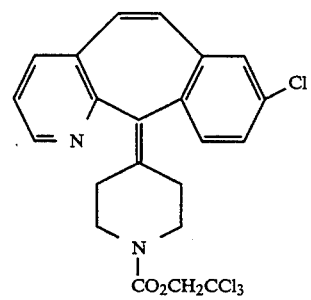

To a mixture of 755 mg (2.34 mmole) of 8-chloro-11-(1-methyl-4-piperidylidene)-11H-benzo[5,6]cyclohepta[1,2-b]pyridine and 1.5 mL of triethylamine in 25 mL of dry toluene at room temperature and under a nitrogen atmosphere was added 650 μL (4.72 mmole) of 2,2,2-trichloroethyl chloroformate. The mixture was then heated to 90° C. Additional amounts of the chloroformate (500 μL and 300 μL) and triethylamine (1.0 mL each time) were added to the mixture after 2 hr. and 3 hr. 40 min., respectively. After a total reaction time of 5 hr. the mixture was poured into water and extracted three times with $CH_2Cl_2$. The combined organic portions were dried over $MgSO_4$, filtered and concentrated in vacuo. The residue was purified via flash chromatography [1.5% $CH_3OH$ in $CH_2Cl_2$] to afford 639 mg (56%) of the title compound as a glass.

E. 8-CHLORO-11-(4-PIPERIDYLIDENE)-11H-BENZO[5,6]CYCLOHEPTA[1,2-b]PYRIDINE

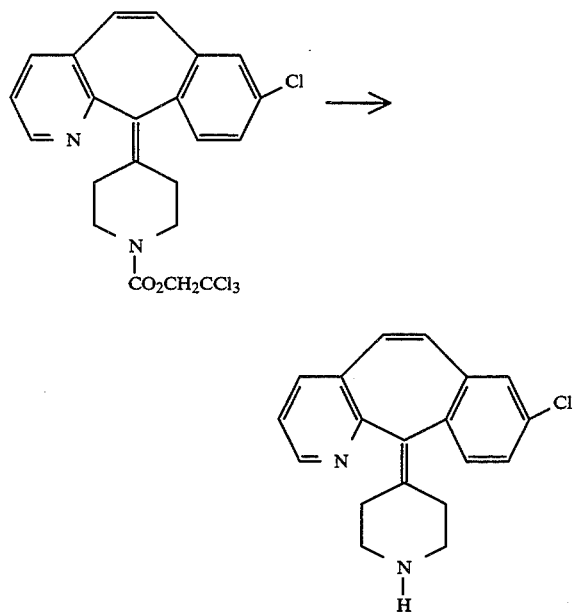

A mixture of 210 mg (0.434 mmole) of 8-chloro-11-[1-(2,2,2-trichloroethoxycarbonyl)-4-piperidylidene]-11H-benzo[5,6]cyclohepta[1,2-b]pyridine and 526 mg (8.05 mmole) of zinc dust in 4 mL of acetic acid was heated at 60°–70° C. After 2 hr. 20 min. another 547 mg (8.37 mmole) of zinc dust was added. After another 30 min. the mixture was basified with 10% aqueous NaOH and extracted four times with $CH_2Cl_2$. The combined organic portions were washed once with water, dried over $MgSO_4$, filtered, and concentrated in vacuo. The residue was purified via flash chromatography [5→6% $CH_3OH/NH_3$ in $CHCl_3$] to yield 71 mg (53%) of the title compound as a glass.

PREPARATIVE EXAMPLE 4

A. 5-METHOXY-8-CHLORO-11H-BENZO[5,6]CYCLOHEPTA[1,2-b]PYRIDIN-11-ONE
B. 6-METHOXY-8-CHLORO-11H-BENZO[5,6]CYCLOHEPTA[1,2-b]PYRIDIN-11-ONE

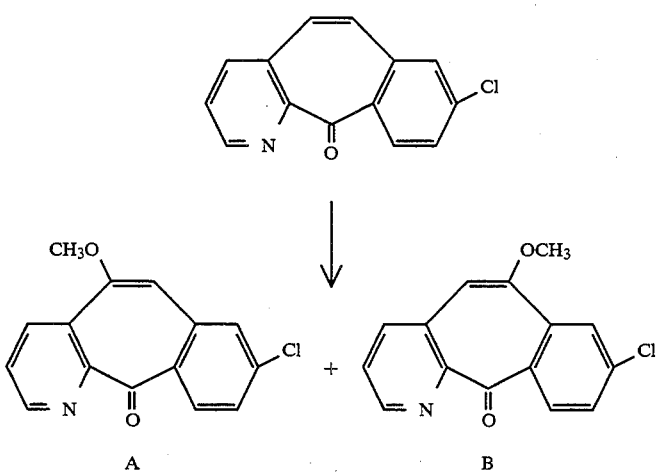

Add $Br_2$ (5.10 mL, 99 mmol) to a mixture of 8-chloro-11H-benzo[5,6]cyclohepta[1,2-b]pyridin-11-one (8.15 g, 33.7 mmol) and powdered $AgNO_3$ (23.19 g, 137 mmol) in 300 mL of dry methanol at room temperature and under an argon atmosphere. After 8 hours, add additional $AgNO_3$ (5.90 g, 34.7 mmol) followed by additional $Br_2$ (1.7 mL, 33.0 mmol). After 0.5 hours pour the mixture into water and extract (4×) with $CH_2Cl_2$. Combine the organic phases, dry over magnesium sulfate, filter and concentrate in vacuo to give a mixture of the crude bromo ethers.

Dissolve the crude product in $CH_2Cl_2$ (200 mL) at room temperature and place under an argon atmosphere. Add DBU (20 mL, 134 mmol) and reflux for 1.3 hours. Add additional DBU (10 mL, 67 mmol) and reflux the mixture for an additional hour. Pour the mixture into water and extract (3×) with $CH_2Cl_2$. Combine the organic phases, wash with water and dry over magnesium sulfate. Filter and concentrate in vacuo. The two isomeric vinyl ethers, title compounds A and B, are separated via flash chromatography [40%→75% ethyl acetate in hexanes] and recrystallize from ethyl acetate hexanes to give title compound A (1.51 g, 14.3%, mp 156° to 158° C.) and title compound B (3.68 g, 35%, mp: 161°–162° C.).

C. 5-METHOXY-8-CHLORO-11-(1-METHYL-4-PIPERIDINYL)-11H-BENZO[5,6]CYCLOHEPTA[1,2-b]PYRIDIN-11-OL

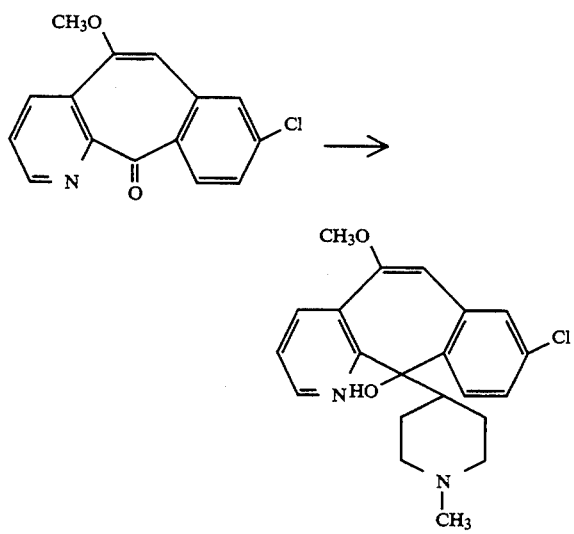

Add a 1.5M Grignard solution of N-methyl 4-chloropiperidine (150 mL, 22.5 mmol) in THF dropwise over a 7 minute period to 5-methoxy-8-chloro-11H-benzo[5,6]cyclohepta[1,2-b]pyridin-11-one (5.00 g, 18.4 mmol) in THF (70 mL) at 0° C. and under an argon atmosphere. Quench the reaction after 30 minutes with a saturated solution of NH$_4$Cl (pH 8) and extract (3×) with CHCl$_3$. Combine the organic portions, wash with brine, dry over sodium sulfate, filter and concentrate in vacuo. Purify via flash chromatography (5% CH$_3$OH in CH$_2$Cl$_2$) to give the title compound (3.60 g, 53%) as a solid. The solid may be recrystallized from isopropyl ether to give a white powder (mp: 168°–170° C.).

D. 8-CHLORO-11-(1-METHYL-4-PIPERIDYLIDENE)-6,11-DIHYDRO-5H-BENZO[5,6]CYCLOHEPTA[1,2-b]PYRIDIN-5-ONE

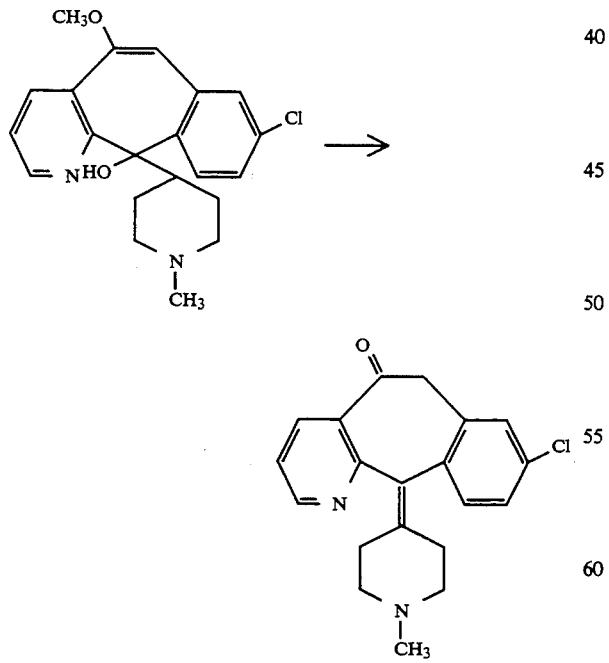

Dissolve 5-methoxy-8-chloro-11-(1-methyl-4-piperidinyl)-11H-benzo[5,6]cyclohepta[1,2-b]pyridin-11-ol (4.26 g) in CH$_3$OH (6 mL) at 0° C. under an argon atmosphere. Add slowly a cooled solution of 92% aqueous H$_2$SO$_4$ (54 mL). Allow the mixture to warm to room temperature for 35 minutes. Pour the solution onto ice, basify with aqueous NaOH (25%), and extract with methylene chloride (3×). Combine the organic portions, wash with brine and dry over sodium sulfate. Filter and concentrate in vacuo. Triturate the residue with isopropyl ether to give an intermediate, 8-Chloro-6,11-dihydro-11-(1-methyl-4-piperidinyl)-5,11-epoxy-5H-benzo[5,6]-cyclohepta[1,2-b]pyridin-5-ol as a white solid (3.58 g., 92%, m.p: 170° to 174° C. as HCl salt).

Dissolve the intermediate compound (3.58 g, 10.0 mmol) in trifluoromethane sulfonic acid (50 mL) and heat to 45° C. under an argon atmosphere for 3 hours. Pour the mixture onto ice, basify with aqueous NaOH (25% w/v), and extract with CHCl$_3$ (3×). Combine the organic portions, wash with brine and dry over sodium sulfate. Filter and concentrate in vacuo. Chromatograph on silica gel (5% CH$_3$OH in CH$_2$Cl$_2$) to give the title compound as an off white solid (1.703 g, 50%, 58% based on recovered starting material). An analytical sample was prepared by recrystallization of the product with ethyl acetate/isopropyl ether (mp: 162°–163° C.).

E. ETHYL-4-(8-CHLORO-5-ETHOXYCARBONYLOXY-11H-BENZO[5,6]CYCLOHEPTA[1,2-b]PYRIDIN-11-YLIDENE)-1-PIPERIDINE CARBOXYLATE

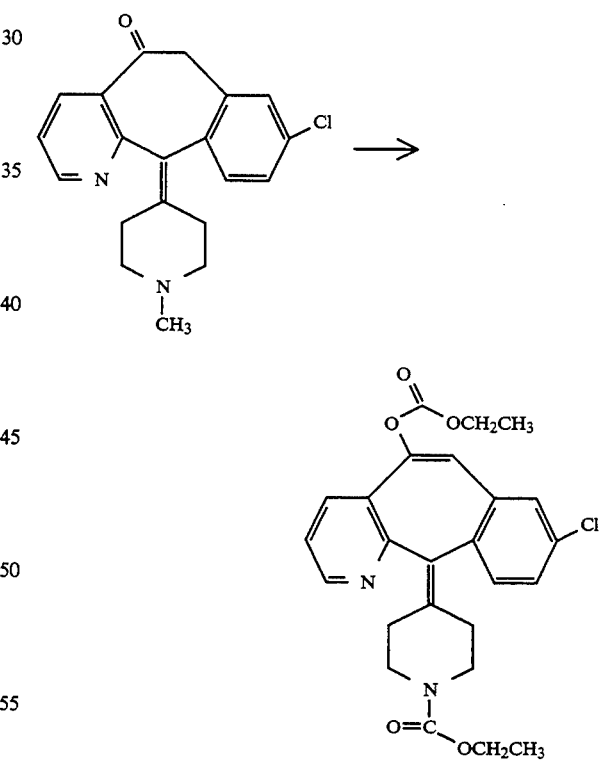

Dissolve the 8-chloro-11-(1-methyl-4-piperidylidene)-6,11-dihydro-5H-benzo[5,6]cyclohepta[1,2-b]pyridin-5-one (617 mg, 1.82 mmol) and triethylamine (0.50 mL, 3.58 mmol) in toluene (12 mL) at 80° C. under an argon atmosphere. Add dropwise over 2 minutes ethyl chloroformate (0.87 mL, 9.10 mmol). After 25 minutes cool the mixture to room temperature, filter, and concentrate in vacuo. Purify the crude product via flash chromatography (1% CH$_3$OH in CH$_2$Cl$_2$) to yield the title compound as a glass (834 mg, 98%).

F. 8-CHLORO-11-(4-PIPERIDYLIDENE)-6,11-DIHYDRO-5H-BENZO[5,6]CYCLOHEPTA-[1,2-b]PYRIDIN-5-ONE

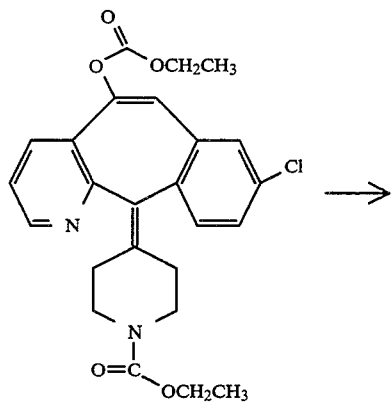

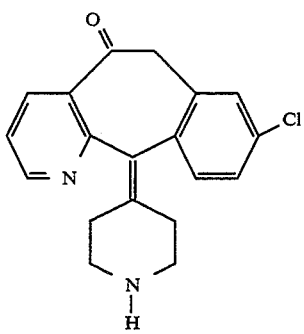

Mix ethyl 4-(8-chloro-5-ethoxycarbonyloxy-11H-benzo[5,6]cyclohepta[1,2-b]pyridi-11-ylidene)-1-piperidine carboxylate (897 mg, 1.91 mmol) and aqueous KOH (20 mL, 13% w/v) in ethanol (15 mL) and reflux under an argon atmosphere for 25 hours. Pour the mixture into water and extract with CHCl$_3$ (3×). Combine the organic portions, wash with brine, dry over sodium sulfate, filter, and concentrate in vacuo. Purify the residue via flash chromatography (2% CH$_3$OH saturated with NH$_3$ in CH$_2$Cl$_2$) and triturate with isopropyl ether to give the title compound as a white solid (417 mg, 67%, mp: 194°–196° C. (dec)).

G. 5-HYDROXY-8-CHLORO-11-(4-PIPERIDYLIDENE)-6,11-DIHYDRO-5H-BENZO[5,6]CYCLOHEPTA[1,2-b]PYRIDINE

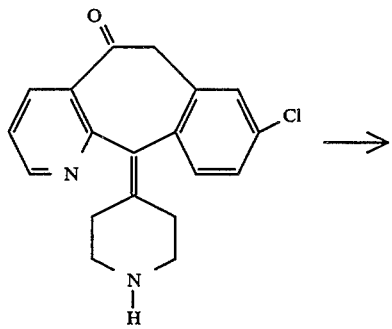

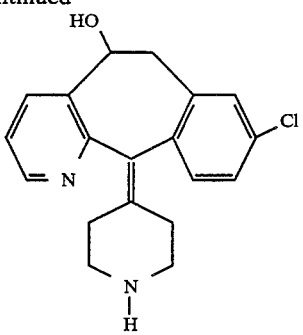

To a mixture of 457 mg (1.41 mmol) of 8-chloro-11-(4-piperidylidene)-6,11-dihydro-5H-benzo[5,6]cyclohepta[1,2-b]pyridin-5-one in 30 mL of methanol at 0° C. and under an argon atmosphere was added in three portions each 5 min apart 263 mg (6.95 mmol) of sodium borohydride. After 1.8 h the mixture was poured into water and extracted with methylene chloride (3×) followed by ethyl acetate (3×). The combined organic portions were dried over MgSO$_4$, filtered, and concentrated in vacuo to afford a product which was precipitated out of 10% methanol saturated with ammonia in methylene chloride to give 410 mg (89%) of the title compound as a white solid. The product is unstable in chlorinated solvents for extended periods of time possibly due to formation of its hydrochloride salt. It could be further purified by crystallization of the product from ethanol to yield the title compound as a white solid: mp 245°–248° C. dec.

H. 6-HYDROXY-8-CHLORO-11-(4-PIPERIDYLIDENE)-6,11-DIHYDRO-5H-BENZO[5,6]CYCLOHEPTA[1,2-b]PYRIDINE

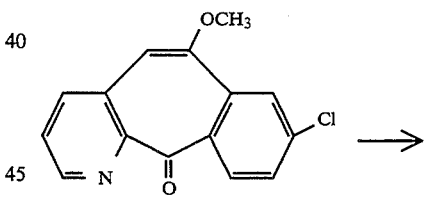

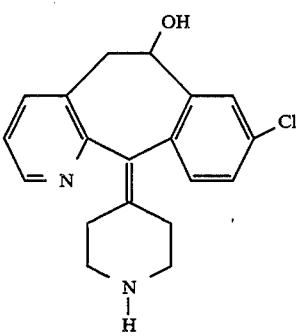

By using a similar procedure to that described in Parts C through G above of Preparative Example 4, one can prepare 6-hydroxy-8-chloro-11-(4-piperidylidene)-6,11-dihydro-5H-benzo[5,6]cyclohepta[1,2-b]pyridine from 6-methoxy-8-chloro-11H-benzo[5,6]cyclohepta[1,2-b]pyridin-11-one of in Part B. However, in Part D of Preparative Example 4, one may use the following procedure in its place:

A mixture of 2.00 g (5.39 mmol) of 6-methoxy-8-chloro-11-(1-methyl-4-piperidinyl)-11H-benzo[5,6]cyclohepta[1,2-b]pyridin-11-ol in 87% aqueous sulfuric acid was stirred at room temperature and under an argon atmosphere. After 30 min 30 mL of trifluoromethanesulfonic acid was added and the mixture was heated to 115° C. One hour later the mixture was cooled to room temperature, poured onto ice, basified with 5% aqueous sodium hydroxide and extracted with methylene chloride (2×). The combined organic portions were washed with brine, dried over Na2SO4, filtered, and concentrated in vacuo to give 1.41 g of 8-chloro-5,11-dihydro-11-(1-methyl-4-piperidinylidene)-6H-benzo[5,6]cyclohepta-[1,2-b]pyridin-6-one. The material was recrystallized from ethyl acetate/isopropyl ether to give 1.12 g (61%) of the ketone as a granular solid: mp 181°–183° C.

PREPARATIVE EXAMPLE 5

A. 1,2,6-TRIMETHYL-4-CHLOROPIPERIDINE

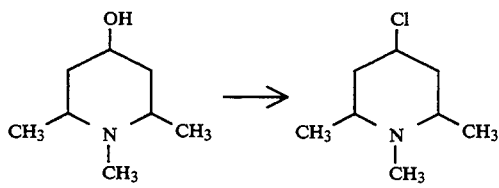

The starting material, 1,2,6-trimethyl-4-piperidinol, may be prepared by the method disclosed in *Archi Kem*, Volume 27, pages 189–192 (1955). To a cooled (ice-bath) solution of 1,2,6-trimethyl-4 -piperidinol (12.2 g, 85.3 mmol) in 120 mL of dry benzene was slowly added thionylchloride (17 mL, 233 mmole). The dark reaction mixture was then warmed to 70° C. for 20 min. The reaction was cooled and then suspended in water followed by filtration. The filtrate was extracted once with diethylether. The aqueous layer was separated and then basified with 30% NaOH solution. The product was then extracted twice with CH2Cl2, washed once with brine, dried (Na2SO4), filtered and solvent removed to give a crude brown liquid which was distilled (2–4 mmHg, 62°–64° C.) to give the title compound (8.0 g, 58% yield).

B. 8-CHLORO-11-(1,2,6-TRIMETHYL-4-PIPERIDINYL)-6,11-DIHYDRO-5H-BENZO[5,6-]CYCLOHEPTA[1,2-b]PYRIDIN-11-OL

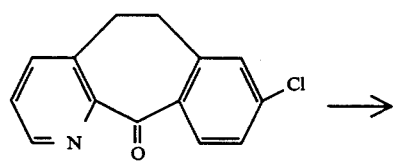

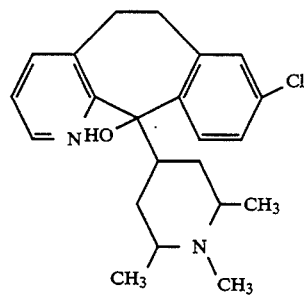

The chloride, 1,2,6-trimethyl-4-chloropiperidine, (4.2 g, 26 mmol) was slowly dripped into a solution of dry THF (18 mL) containing Mg (633 mg, 26.3 mm). The Grignard reagent was then formed after heating for 6 hours at 70° C.

To a cooled (ice-bath), stirred solution of 8-chloro-5,6-dihydro-11H-benzo[5,6]cyclohepta[1,2-b]pyridin-11-one (6.3 g, 26 mmol) in THF (50 mL) was added the above Grignard reagent. The reaction was allowed to stir for 1 hr. at this temperature and then quenched with NH4Cl solution. The product was extracted 3× with ethyl acetate, washed once with brine, dried (Na2SO4), filtered and solvent removed to give a crude brown material which was chromatographed to give the title compound (5.1 g, 53% yield) as a yellowish glass.

C. 8-CHLORO-11-(1-METHYL-(Z)-2,6-DIMETHYL-4-PIPERIDYLIDENE)-6,11-DIHYDRO-5H-BENZO[5,6]CYCLOHEPTA[1,2-b]PYRIDINE AND THE E ISOMER THEREOF

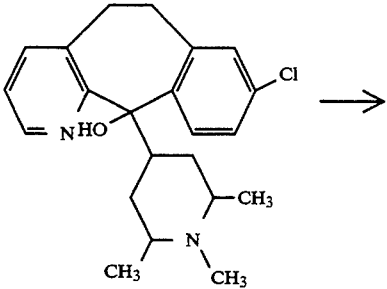

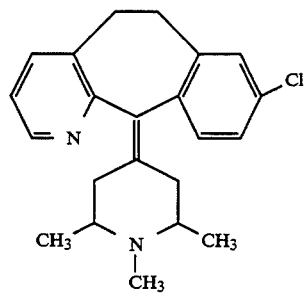

A mixture of 8-chloro-11-(1,2,6-trimethyl-4-piperidinyl)-6,11-dihydro-5H-benzo[5,6]cyclohepta[1,2-b]pyridin-11-ol (5.0 g, 14.1 mmol) in 85% H2SO4 (100 mL) was heated in an oil bath (60°–65° C.) for 3 hours. The reaction was cooled and diluted with water followed by basification with 25% aq. NaOH solution. The crude product was extracted with CH2Cl2, washed with brine, dried (Na2SO4), filtered and solvent removed. Purification and separation of the E and Z isomers via chromatography (2%→5% MeOH saturated with NH₃ in CH₂Cl₂) gave a fraction of the pure Z isomer (300 mg, 6%) and a fraction containing a mixture of E and Z isomers (4.18 g, 82%).

D. 8-CHLORO-11-(1-CYANO-(Z)-2,6-DIMETHYL-4-PIPERIDYLIDENE)-6,11-DIHYDRO-5H-BENZO[5,6]CYCLOHEPTA[1,2-b]PYRIDINE

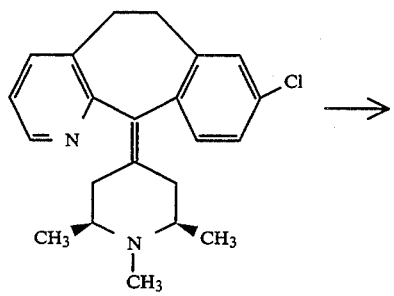

A solution of 300 mg (0.85 mmol) of 8-chloro-11-(1-methyl-(Z)-2,6-dimethyl-4-piperidylidene)-6,11-dihydro-5H-benzo[5,6]cyclohepta[1,2-b]pyridine in benzene (4.5 mL) was slowly dripped into a stirred solution of BrCN (133 mg, 1.2 mmol) in benzene (4.5 mL) at room temperature. This was allowed to stir for 2½ hr under argon. The reaction mixture was suspended between water and ethyl acetate(EtOAc). The EtOAc layer was washed with brine and dried (Na₂SO₄). After filtration the solvent was removed and the crude material was chromatographed (3% CH₃OH in CH₂Cl₂) to give the title compound (251 mg, 81% yield).

E. 8-CHLORO-11-((Z)-2,6-DIMETHYL-4-PIPERIDYLIDENE)-6,11-DIHYDRO-5H-BENZO[5,6]CYCLOHEPTA[1,2-b]PYRIDINE

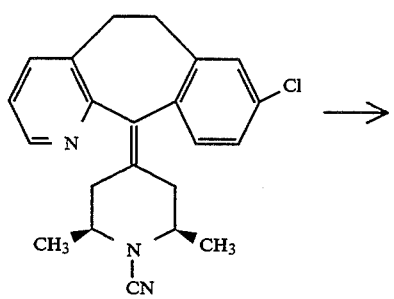

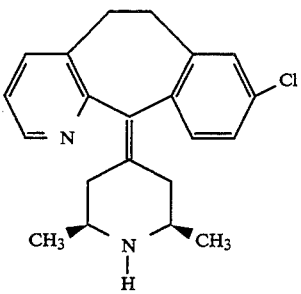

A mixture of 8-chloro-11-(1-cyano-(Z)-2,6-dimethyl-4-piperidylidene)-6,11-dihydro-5H-benzo[5,6]cyclohepta[1,2-b]pyridine (200 mg, 0.55 mmol) in 80% HCl (20 mL) was allowed to reflux for 7 hours. The mixture was cooled and then basified with 25% NaOH. The product was extracted with CH₂Cl₂ (2×), separated, washed once with brine, dried (Na₂SO₄), filtered and solvent removed to give the title compound (174 mg, 93% yield) as a white glass.

F. 8-CHLORO-11-((E)-2,6-DIMETHYL-4-PIPERIDYLIDENE)-6,11-DIHYDRO-5H-BENZO[5,6]CYCLOHEPTA[1,2-b]PYRIDINE

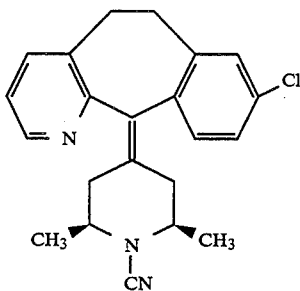

By following similar procedures in steps D & E above, 8-chloro-11-(1-methyl-(E)-2,6-dimethyl-4-piperidylidene)-6,11-dihydro-5H-benzo[5,6]cyclohepta[1,2-b]pyridine was converted to 8-chloro-11-((E)-2,6-dimethyl-4-piperidylidene)-6,11-dihydro-5H-benzo[5,6]cyclohepta-[1,2-b]pyridine.

PREPARATIVE EXAMPLE 6

A. 3,5-DIMETHYLPYRIDINIUM N-OXIDE

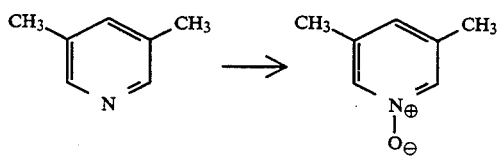

A solution of 285 mL (1.31 mol) of 35% peracetic acid was slowly added to a stirred solution of 149 g (1.39 mol) of 3,5-dimethylpyridine during which the temperature rose to 85° C. and was maintained at this temperature during addition. After the temperature of the mixture dropped to about 35° C. the reaction was stored at 5° C. overnight.

After partial removal of 185 ml of acetic acid via distillation under vacuum, the reaction was washed with NaHSO₄ solution and then neutralized with 10% NaOH solution to pH of about 7. The product was extracted with CH₂Cl₂ to give the title compound as a white solid (yield 142 g, 83%).

B. 1-METHOXY-3,5-DIMETHYLPYRIDINIUM METHYL SULFATE

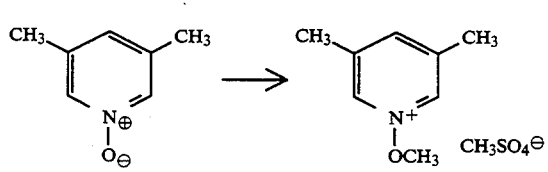

Dimethylsulfate (42.0 g, 0.33 mol) was slowly added to 41.0 g (0.33 mol) of 3,5-dimethylpyridinium N-oxide with mechanical stirring. The mixture was then heated on a steam bath for 1 hr. Then vacuum was applied while cooling to give a brownish solid of the title compound in quantitative yield.

C. 2-CYANO-3,5-DIMETHYLPYRIDINE

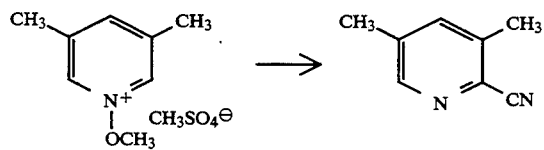

To a cooled (0° C.) solution of sodium cyanide (49.0 g, 0.999 mol, 3.0 eq.) in 135 mL of water (air free) was dripped 1-methoxy-3,5-dimethyl pyridinium methyl sulfate (83.0 g, 0.33 mol) in 100 mL water (air free) in 1.25 hr., keeping the temperature below 3° C. The reaction mixture was stored at about 3° C. overnight. The mixture was filtered and washed with water to give 40 g of the title compound. An analytical sample was recrystallized from isopropyl ether and pentane (4:1) (m.p.: 61°–62° C.).

D. N-(1,1-DIMETHYLETHYL)-3,5-DIMETHYL-2-PYRIDINE CARBOXAMIDE

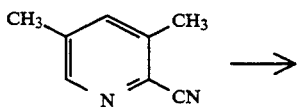

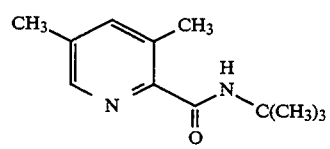

To a stirred solution of 20.3 g (0.153 mol) of 2-cyano-3,5-dimethylpyridine in 100 mL of 20 mL of conc. sulfuric acid within 10 minutes, followed by 20 mL of t-butanol over an additional 15 minutes. The solution was warmed at 75° C. for 30 minutes after which it was cooled to room temperature and basified with 25% NaOH. The product was extracted 3× with EtOAc (600 mL), which was combined and washed 1× with brine, dried (Na₂SO₄), filtered and concentrated in vacuo to give the title compound (31.26 g) as a yellowish oil.

E. 8-CHLORO-3-METHYL-11-(4-PIPERIDYLIDENE)-6,11-DIHYDRO-5H-BENZO[5,6]CYCLOHEPTA[1,2-b]PYRIDINE

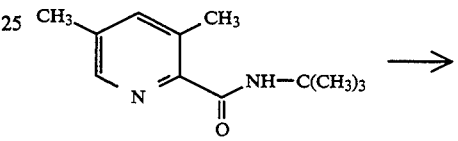

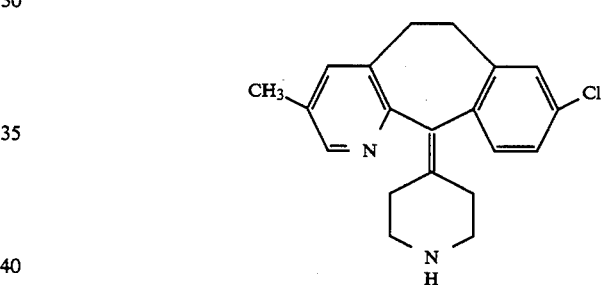

By substituting in step 1B above N-(1,1-dimethylethyl)-3,5-dimethyl-2-pyridine carboxamide for N-(1,1-dimethylethyl)-3-methyl-2-pyridine carboxamide and employing basically the same methods as steps B through G of Preparative Example 1, one obtains 8-chloro-3-methyl-11-(4-piperidylidene)-6,11-dihydro-5H-benzo[5,6]cyclohepta[1,2-b]pyridine. Reaction times are determined by TLC or HPLC.

PREPARATIVE EXAMPLE 7

A. 1-(1-METHYL-4-PIPERIDINYL)-1-[3-(2-PHENYLETHYL)-2-PYRIDYL]METHANOL

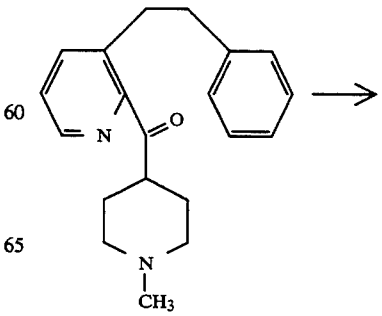

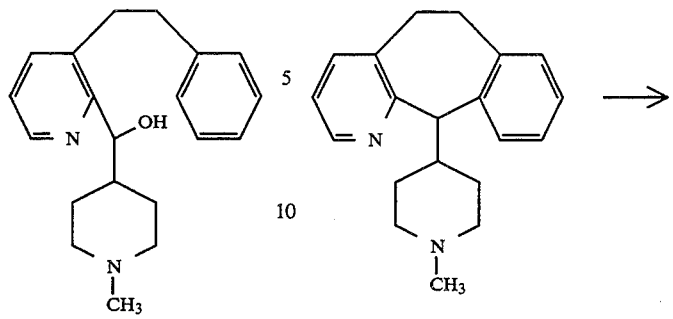

To a mixture of 5.0 g (16.2 mmole) of (1-methyl-4-piperidinyl)[3-(2-phenylethyl)-2-pyridinyl]methanone (which can be prepared in the same manner as described in Preparative Example 1 Steps A–D except using benzyl chloride in place of meta-chlorobenzyl chloride) in 70 mL of methanol was added portionwise 0.8 g (21.1 mmole) of sodium borohydride. The next day the solution was concentrated in vacuo to give a slurry which was dissolved in water and extracted with CHCl$_3$. The combined organic portions were dried over MgSO$_4$, filtered, and concentrated in vacuo to provide a liquid which was distilled (bp 190°–195° C. @1 mm Hg) to give 4.4 g of the title compound as a viscous oil.

B. 11-1-METHYL-4-PIPERIDYL)-6,11-DIHYDRO-5H-BENZO[5,6]CYCLOHEPTA[1,2-b]PYRIDINE

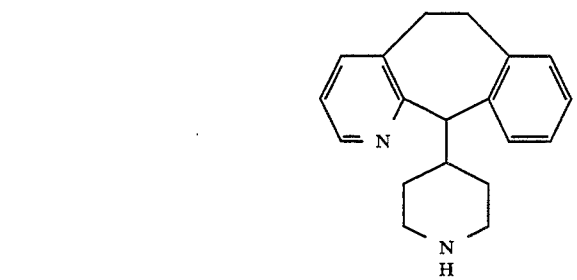

A mixture of 3.5 g (11.3 mmole) of 1-(1-methyl-4-piperidyl)-1-[3-(2-phenylethyl)-2-pyridyl]methanol and 200 g of polyphosphoric acid was heated between 160°–170° C. for 13 hours. The mixture was cooled to room temperature, poured into water, basified with aqueous NaOH and extracted with ether. The combined organic portions were concentrated in vacuo and the product recrystallized to give the title compound as a white solid, (mp 111°–114° C.).

C. 11-(4-PIPERIDYL)-6,11-DIHYDRO-5H-BENZO[5,6]CYCLOHEPTA[1,2,B]PYRIDINE

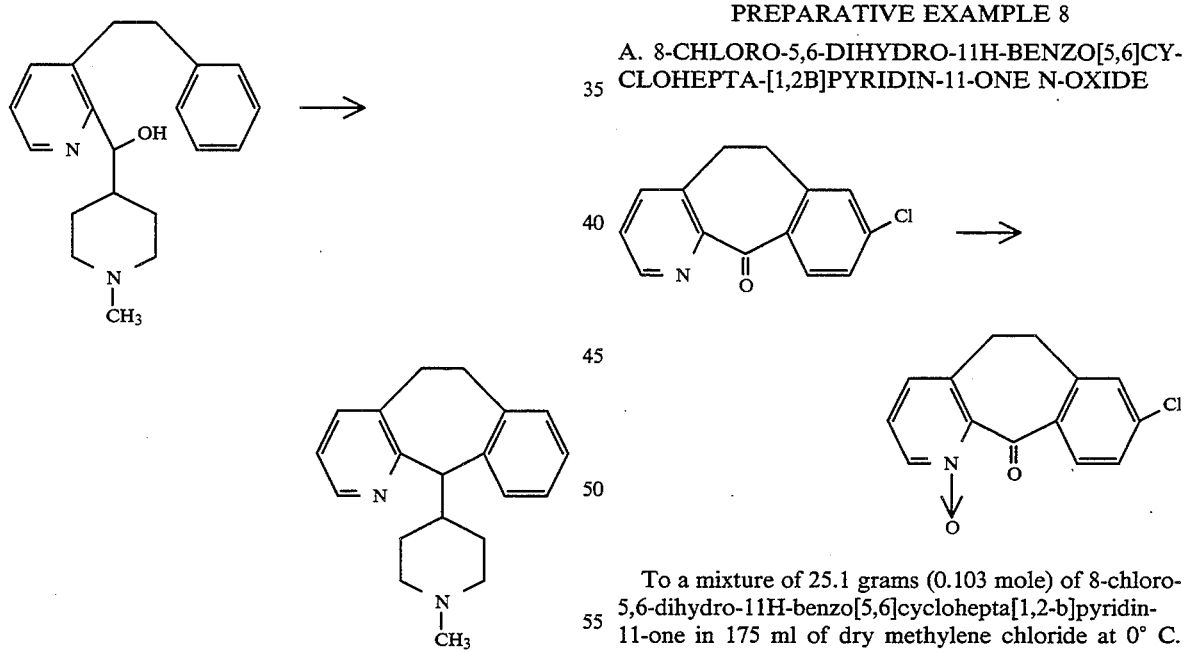

In a similar manner to that described in Preparative Example 1, Steps F–G, 11-(1-methyl-4-piperidyl)-6,11-dihydro-5H benzo[5,6]cyclohepta[1,2-b]pyridine can be converted to 11-(4-piperidyl)-6,11-dihydro-5H-benzo[5,6]cyclohepta[1,2-b]pyridine.

PREPARATIVE EXAMPLE 8

A. 8-CHLORO-5,6-DIHYDRO-11H-BENZO[5,6]CYCLOHEPTA-[1,2B]PYRIDIN-11-ONE N-OXIDE

To a mixture of 25.1 grams (0.103 mole) of 8-chloro-5,6-dihydro-11H-benzo[5,6]cyclohepta[1,2-b]pyridin-11-one in 175 ml of dry methylene chloride at 0° C. under an argon atmosphere was added dropwise over 70 minutes a solution of 24.12 grams of 3-chloroperoxybenzoic acid in 150 ml of methylene chloride. After the addition the solution was stirred for ½ hour after which the ice bath was removed. After two days the reaction was poured into 1.0N aqueous sodium hydroxide and extracted with methylene chloride. The organic portions were combined, washed once with water, dried over magnesium sulfate, filtered and concentrated in vacuo. The resultant product was triturated with isopropyl ether and filtered to provide 25.8 grams (96%) yield of the title compound.

B. 2,8-DICHLORO-5,6-DIHYDRO-11H-BENZO[5,6-]CYCLOHEPTA[1,2-B]PYRIDIN-11-ONE AND 4,8-DICHLORO-5,6-DIHYDRO-11H-BENZO[5,6]CYCLOHEPTA[1,2-b]PYRIDIN-11-ONE

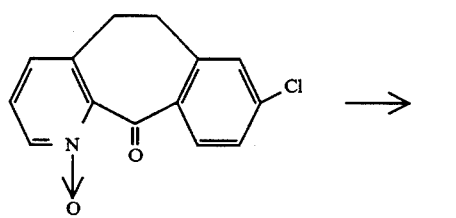

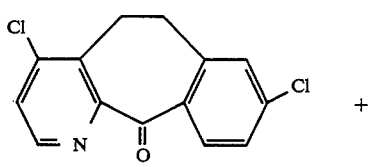

+

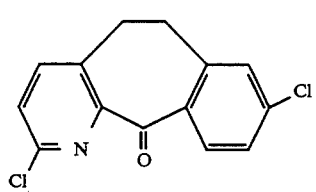

To a mixture of 29.13 grams (112.2 mmol) of the title compound from Preparative Example 9A above, in 40 ml of dry methylene chloride at 0° C. and under argon atmosphere was added 500 ml of 1.0M $SO_2Cl_2$ dropwise over 1 hour. The ice bath was then removed and the reaction stirred at room temperature for 1 hr and then refluxed for seven hours. The mixture was poured into 1.0N aqueous NaOH and extracted three times with $CH_2Cl_2$. The organic portions were combined, dried over $MgSO_4$, filtered and concentrated in vacuo to yield a product which was purified and separated via flash chromatography to yield the two title compounds.

C. 4-(2,8-DICHLORO-5,6-DIHYDRO-11H-BENZO[5,6]CYCLOHEPTA[1,2-b]PYRIDIN-11-YLIDENE)PIPERIDINE AND 4-(4,8-DICHLORO-5,6-DIHYDRO-11H-BENZO[5,6]CYCLOHEPTA[1,2-b]PYRIDIN-11-YLIDENE)PIPERIDINE

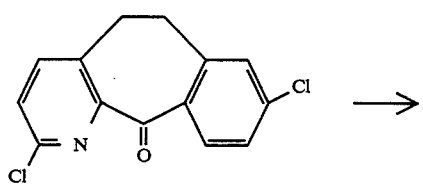

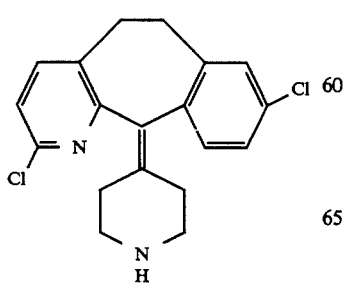

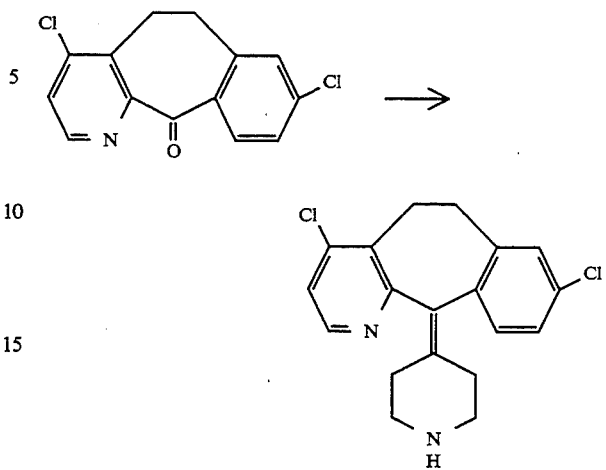

By following essentially the same procedure as that described in parts D–G of Preparative Example 2 above, the 2,8-dichloro and 4,8-dichloro products of Preparative Example 8B above were convened to the corresponding title compounds.

PREPARATIVE EXAMPLE 9

A. 4-(8-CHLORO-2-HYDROXY-5,6-DIHYDRO-11H-BENZO[5,6]CYCLOHEPTA[1,2-b]PYRIDIN-11-YLIDENE)PIPERIDINE

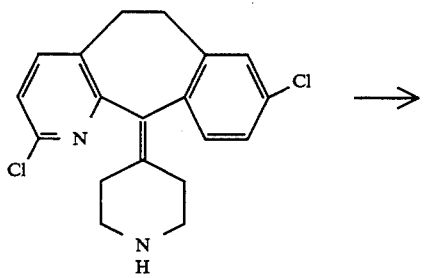

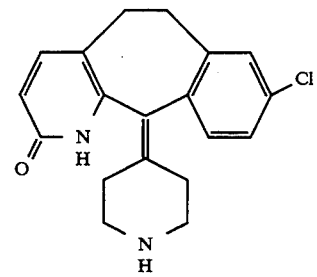

A mixture of 180 mg of the 2,8-dichloro title compound of Preparative Example 8-C above, 7 ml of 2.0N aqueous sodium hydroxide and 7 ml of methanol were heated at 160° C. under a nitrogen atmosphere in a sealed pressure vessel for two days. The vessel was then cooled to room temperature. The mixture was poured into water and extracted three times with methylene chloride. The organic portions were combined, dried over magnesium sulfate, filtered and concentrated in vacuo to provide a residue which was triturated with isopropyl ether/methylene chloride to provide 85 mg of the title compound as a white solid.

B. By using the procedure of Preparative Example 9 above, one may make substitutions of other groups at the 2-position by employing the appropriate nucleophile in place of sodium hydroxide (e.g. dimethylamine, ammonia, potassium thiolate, etc.).

PREPARATIVE EXAMPLE 10

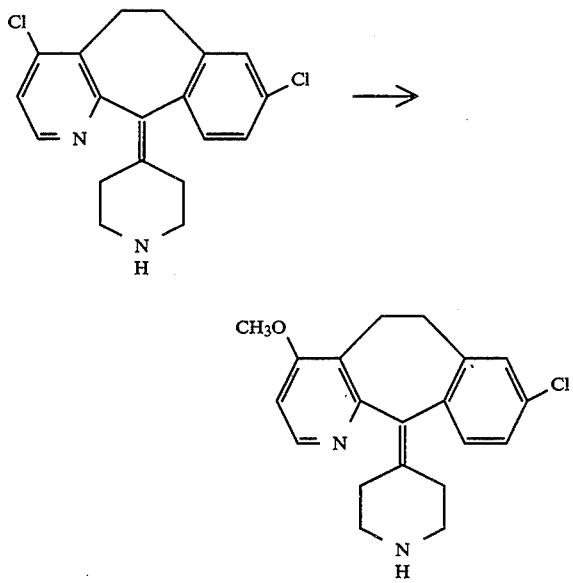

A. 4-(8-CHLORO-4-METHOXY-5,6-DIHYDRO-11H-BENZO[5,6]CYCLOHEPTA[1,2-b]PYRIDIN-11-YLIDENE)PIPERIDINE

A mixture of 212 mg of the 4,8-dichloro title compound of Preparative Example 8-C above, 7 ml of 2.0N aqueous sodium hydroxide and 7 ml of methanol were heated at 135° C. under a nitrogen atmosphere in a sealed pressure vessel for 18 hours. The vessel was then cooled to room temperature. The mixture was poured into water and extracted three times with methylene chloride. The organic portions were combined, dried over magnesium sulfate, filtered and concentrated in vacuo to provide a residue which was purified via flash chromatography (4→7% methanol saturated with ammonia in methylene chloride) and then triturated with isopropyl ether/methylene chloride to provide 144 mg of the title compound as a white glass.

B. By using the procedure of Preparative Example 10 above, one may make substitutions of other groups at the 4-position by employing the appropriate nucleophile in place of sodium hydroxide (e.g. dimethylamine, ammonia, potassium thiolate, etc.).

PREPARATIVE EXAMPLE 11

A. By substituting the compound listed in Column 1 TABLE 5 below for 3,5-dimethylpyridine in Preparative Example 6 above and following basically the same procedure (steps A-E), the compounds listed in Column 2 below can be prepared. Note that the addition of the nitrile group to the pyridine in step C. of Preparative Example 6 can result in the formation of other undesirable isomers which can be removed via flash chromatography.

TABLE 5

Column 2

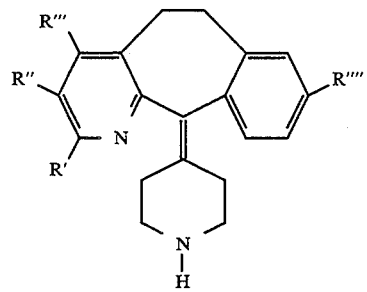

| Column 1 | R' = | R'' = | R''' = | R'''' = |
|---|---|---|---|---|
| Cl—pyridine—CH3 | H | Cl | H | H |
|  | H | Cl | H | Cl |
| Br—pyridine—CH3 | H | Br | H | Cl |
| Ph—pyridine—CH3 | H | Ph-group | H | Cl |

TABLE 5-continued

Column 2

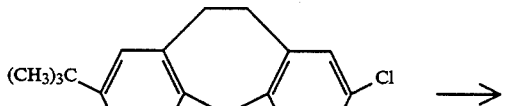

| Column 1 | R' = | R" = | R''' = | R'''' = |
|---|---|---|---|---|
| 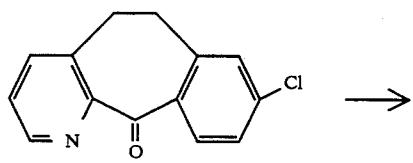 | CH₃ | H | H | Cl |
| 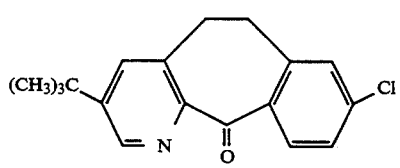 | H | H | CH₃ | Cl |

PREPARATIVE EXAMPLE 12

A. 3-(1,1-DIMETHYL-1-ETHYL)-8-CHLORO-5,6-DIHYDRO-11H-BENZO[5,6]CYCLOHEPTA[1,2-b]PYRIDIN-11-ONE

To a mixture of 20.05 grams (82.28 mmol) of 8-chloro-5,6-dihydro-11H-benzo[5,6]cyclohepta[1,2-b]pyridin-11-one in 400 ml of dry tetrahydrofuran at −72° C. and under an atmosphere of nitrogen was added dropwise over 40 minutes 66.0 ml of 2.7M t-butyl magnesium chloride in tetrahydrofuran. The reaction mixture was slowly warmed to room temperature and stirred overnight. The mixture was then poured into 10% aqueous ammonium chloride and extracted four times with methylene chloride. The combined organic portions were dried over magnesium sulfate, filtered, and concentrated in vacuo to give the title compound, along with 8-chloro-11-(1,1-dimethyl-1-ethyl)-6,11-dihydro-5H-benzo[5,6]cyclohepta[1,2-b]pyridin-11-ol. These compounds were separated via flash chromatography to give the title compound, which was recrystallized from isopropyl ether to give 4.37 grams (18%) of the title compound as a white solid.

B. 4-[3-(1,1-DIMETHYL-1-ETHYL)-8-CHLORO-5,6-DIHYDRO-11H-BENZO[5,6]CYCLOHEPTA[1,2-b]PYRIDIN-11-YLIDENE]PIPERIDINE

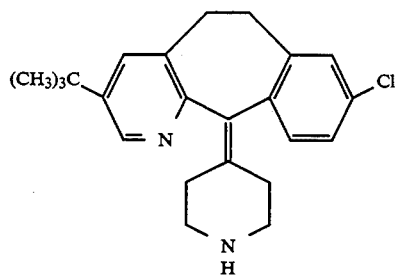

By using the title compound of Part A above and applying essentially the same procedure described in parts D–G of Preparative Example 2 above, one can obtain the title compound.

PREPARATIVE EXAMPLE 13

A. 4-[8-CHLORO-5,6-DIHYDRO-3-(1-HYDROXY-1-ETHYL)-11H-BENZO[5,6]CYCLOHEPTA[1,2-B]PYRIDIN-11-YLIDENE]PIPERIDINE

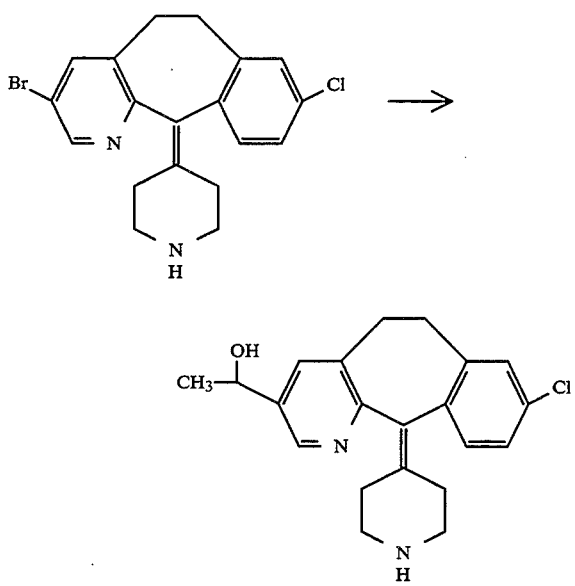

3-Bromo-8-chloro-6,11-dihydro-11-(4-piperidylidene)-5H-benzo[5,6]cyclohepta[1,2-b]pyridine (779.4 mg) in dry tetrahydrofuran (25 mL) was cooled to −76° C. under argon. To this was dripped in n-butyl lithium (1.76 mL in hexane, 2.2 eq.) keeping the temperature below −74° C. After stirring for 10 minutes acetaldehyde was bubbled into the solution until the reaction color turned yellowish in approximately 20 minutes. The mixture was allowed to stir for 20 minutes and then quenched with water followed by extraction with methylene chloride. The organic phase was dried (Na$_2$SO$_4$) and then filtered. Solvent was removed and the crude product was chromatographed on SiO$_2$, eluted with 10% methanol saturated with ammonia in methylene chloride to give 219 mg of the title compound.

B. By following essentially the same procedure as described above in Preparative Example 13, but using other electrophiles in place of acetaldehyde (e.g., CO$_2$, ethyl propargylate, ethyl formate, etc.), one may make compounds which contain a carboxy, a 3-carboethoxy-1-propen-1-yl, and formyl, respectively, at the 3-position.

PREPARATIVE EXAMPLE 14

A. 8-CHLORO-6,11-DIHYDRO-11-HYDROXY-5H-BENZO[5,6]CYCLOHEPTA[1,2-b]PYRIDINE

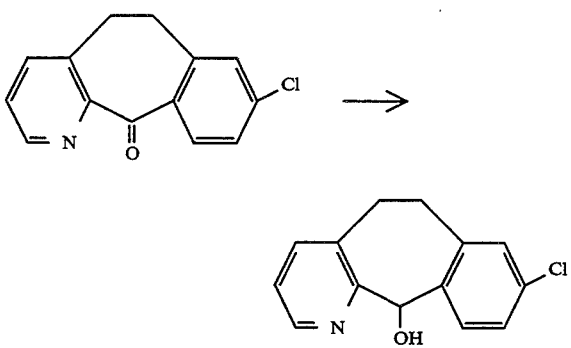

To a mixture of 25.03 (103 mmol) of 8-chloro-5,6-dihydro-11H-benzo[5,6]cyclohepta[1,2-b]pyridin-11-one in 200 mL of methanol at room temperature and under a nitrogen atmosphere was added portionwise over a period of about 1 hour 4.82 g (124 mmol) of sodium borohydride. Occasional cooling with an ice bath was necessary at times during the addition in order to avoid excessive reflux. After 1.6 hour the mixture was poured into ice cold water and then extracted with ethyl acetate (3×). The combined organic portions were washed with brine, dried over magnesium sulfate, filtered, and concentrated in vacuo. The residue was recrystallized from hot isopropyl ether. The remaining filtrate was purified via flash chromatography (20% ethyl acetate in hexanes) to yield more product which solidified on standing. Both batches were combined to yield 20.41 g of the title compound as a white solid.

B. 8,11-DICHLORO-6,11-DIHYDRO-5H-BENZO[5,6]CYCLOHEPTA[1,2-b]PYRIDINE

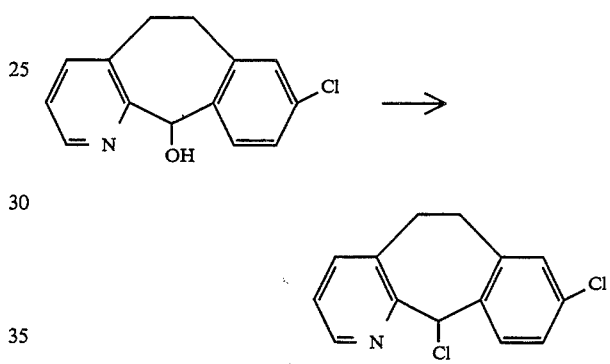

To a mixture of 13.3 g (54 mmol) of 8-chloro-6,11-dihydro-11-hydroxy-5H-benzo[5,6]cyclohepta[1,2-b]pyridine in 290 mL of toluene at −15° C. and under an atmosphere of nitrogen was added via syringe pump over a period of 1 hour 6.20 mL (85.7 mmol) of thionyl chloride. The extent of reaction was monitored by TLC (50% ethyl acetate in hexanes). When completed the mixture was poured into 300 mL of 1.0N aqueous sodium hydroxide and extracted with ethyl acetate (5×). The combined organic portions were washed with brine, dried over sodium sulfate, filtered, and concentrated in vacuo. The residue was taken up in ethyl acetate, quickly filtered through basic alumina, and concentrated again to yield a product which was triturated with pentane to yield 10.22 g of the title compound as a tan solid.

C. 8-CHLORO-11-(1-PIPERAZINYL)-6,11-DIHYDRO-5H-BENZO[5,6]CYCLOHEPTA[1,2-b]PYRIDINE

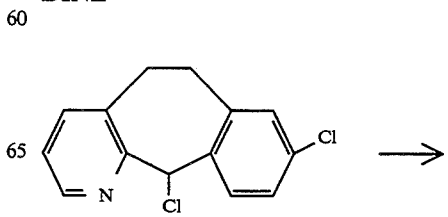

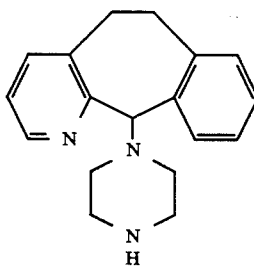

To a mixture of 10.0 g (37.9 mmol) of 8,11-dichloro-6,11-dihydro-5H-benzo[5,6]cyclohepta[1,2-b]pyridine and 1.0 mL of triethylamine in 200 mL of dry tetrahydrofuran at room temperature and under a nitrogen atmosphere was added 33.0 g of piperazine. The mixture was stirred at room temperature for 22.5 hours and then refluxed for 5.5 hours. It was then cooled to room temperature, poured into 250 mL of 5% aqueous sodium hydroxide, and extracted with methylene chloride (3×). The combined organic portions were washed with brine, dried over magnesium sulfate, filtered, and concentrated in vacuo. The residue was purified via flash chromatography (2→5% methanol saturated with ammonia in methylene chloride) to yield the title compound as a glass.

PREPARATIVE EXAMPLE 15

A. RESOLUTION OF (±)-8-CHLORO-6,11-DIHYDRO-11-(1-PIPERAZINYL)-5H-BENZO[5,6]CYCLOHEPTA[1,2-b]PYRIDINE

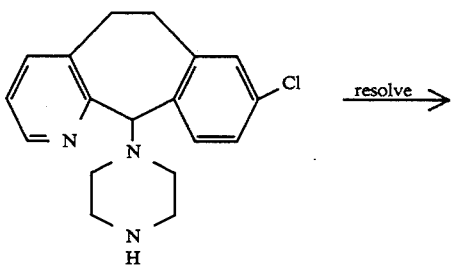

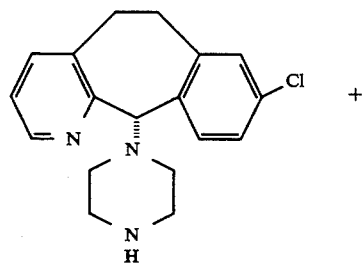

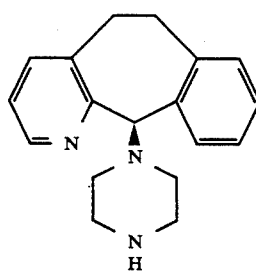

A solution of 2.51 g (8.0 mmol) of (±)-8-chloro-6,11-dihydro-11-(1-piperazinyl)-5H-benzo[5,6]cyclohepta[1,2-b]pyridine in 40 mL of 8% aqueous CH₃CN was mixed on a steam bath with a solution of 1.386 g (1 eq) of N-acetyl-L-leucine in 40 mL of 8% aqueous CH₃CN. This solution was filtered and then allowed to cool to room temperature overnight. The material that crystallized was removed by filtration and washed with 20 mL of 8% aqueous CH₃CN to afford 1.193 g of the (+)-salt.

Similarly, the above procedure was carried out with 6.904 g (22 mmol) of (±)-8-chloro-6,11-dihydro-11-(1-piperazinyl)-5H-benzo[5,6]cyclohepta[1,2-b]pyridine and 3.811 g (1 eq) of N-acetyl-L-leucine in 220 mL of 8% aqueous CH₃CN to afford 2.887 g of the same (+)-salt.

The combined (+)-salt, 4.08 g, was recrystallized from 150 mL of 10% aqueous CH₃CN to give 2.13 g of the (+)-salt: mp. 234°–236° C. (dec). The filtrate was concentrated and then recrystallized with 50 mL of 8% aqueous CH₃CN to afford another 652 mg of (+)-salt: mp. 234°–236° C. (dec).

$[\alpha]^{26}_D = +54.8°$.

The combined two batches of (+)-salt were used in Step B below.

The filtrates and washings of the combined two batches were concentrated and then dissolved in 0.5M K₂CO₃ solution and then extracted with CH₂Cl₂ to give 7.46 g of free base. This base was treated with N-acetyl-D-leucine similarly as described above to afford 5.413 g of salt. This salt was recrystallized with 205 mL of 12.5% aqueous CH₃CN to give 1.537 g of the (−)-salt, mp. 234°–236° C. (dec). The filtrate was concentrated and then recrystallized with 125 mL of 11.7% aqueous CH₃CN to give another 1.5 g of (−)-salt, mp. 234°–236° C. (dec). The combined (−)-salt was used in Step C below.

B. PURIFICATION OF (+)-8-CHLORO-6,11-DIHYDRO-11-(1-PIPERAZINYL)-5H-BENZO[5,6-]CYCLOHEPTA[1,2-b]PYRIDINE

The combined (+)-salt from step A above, 2.782 g, was suspended in 100 mL of 0.5M NaHCO₃ solution and 200 mL of CH₂Cl₂ and stirred until all salts disappeared. The aqueous phase was then extracted with 200 mL CH₂Cl₂. The combined CH₂Cl₂ layers were washed with 200 mL H₂O and then with 100 mL brine, dried over Na₂SO₄ and filtered. Upon removal of solvent, the residue was triturated with diisopropyl ether to give 1.7 g of (+)-8-chloro-6,11-dihydro-11-(1-piperazinyl)-5H-benzo[5,6]cyclohepta[1,2-b]pyridine: mp. 153°–155° C.

$[\alpha]^{26}_D = +76.7°$.

C. PURIFICATION OF (−)-8-CHLORO-6,11-DIHYDRO-11-(1-PIPERAZINYL)-5H-BENZO[5,6-]CYCLOHEPTA[1,2-b]PYRIDINE

The combined (−)-salt from step A above, 3.037 g, was converted into the free base and worked up as described in Step B above. Further washing with diisopropylether gave (−)-8-chloro-6,11-dihydro-11-(1-piperazinyl)-5H-benzo[5,6]cyclohepta[1,2-b]pyridine: mp. 153°–155° C.

$[\alpha]^{26}_D = -75.6°$.

PREPARATIVE EXAMPLE 16

A. 1-(10,11-DIHYDRO-5H-DIBENZO[a,d]CYCLOHEPTEN-5-YLIDENE)-4-(2,2,2-TRICHLOROETHYLOXYCARBONYL)PIPERIDINE

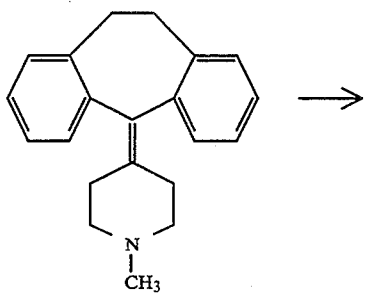 

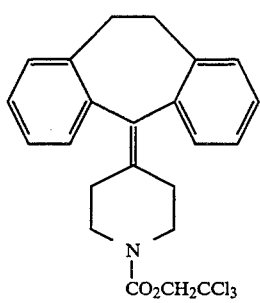

To a mixture of 4.35 g (15.1 mmol) of 1-(10,11-dihydro-5H-dibenzo[a,d]cyclohepten-5-ylidene)-4-methylpiperidine and 3.0 mL of triethylamine in 80 mL of dry toluene at 90° C. and under an atmosphere of nitrogen was added over 40 minutes 8.1 mL of 2,2,2-trichloroethyloxycarbonyl chloride. The reaction mixture was then stirred for two hours. It was quenched with 1.0N aqueous sodium hydroxide and extracted with ether (3×). The combined organic portions were washed once each with 5% aqueous hydrochloric acid and brine. It was dried over magnesium sulfate, filtered, and concentrated in vacuo. The resultant oil solidified on standing to provide 6.3 g of the title compound.

B. 1-(10,11-DIHYDRO-5H-DIBENZO[a,d]CYCLOHEPTEN-5-YLIDENE)PIPERIDINE

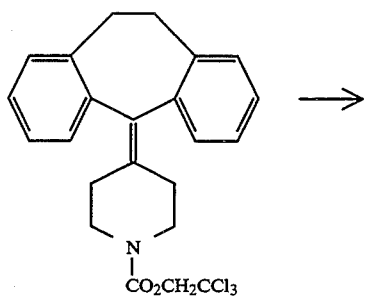 

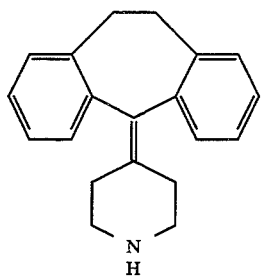

To a mixture of 6.3 g (18.2 mmol) of 1-(10,11-dihydro-5H-dibenzo[a,d]cyclohepten-5-ylidene)-4-(2,2,2-trichloroethyloxycarbonyl)piperidine in 100 mL of glacial acetic acid at 90° C. and under an atmosphere of nitrogen was added 12.36 g of zinc dust. After 3.5 hours reaction mixture was cooled and filtered. The filtrate was taken up ethyl acetate and basified with aqueous sodium hydroxide. The organic phase was dried over magnesium sulfate, filtered and concentrated in vacuo. The crude product was recrystallized to give 2.23 g of the title compound as a white solid.

PREPARATIVE EXAMPLE 17

1-(10,11DIHYDRO-5H-DIBENZO[a,d]CYCLOHEPTEN-5-YL)PIPERAZINE

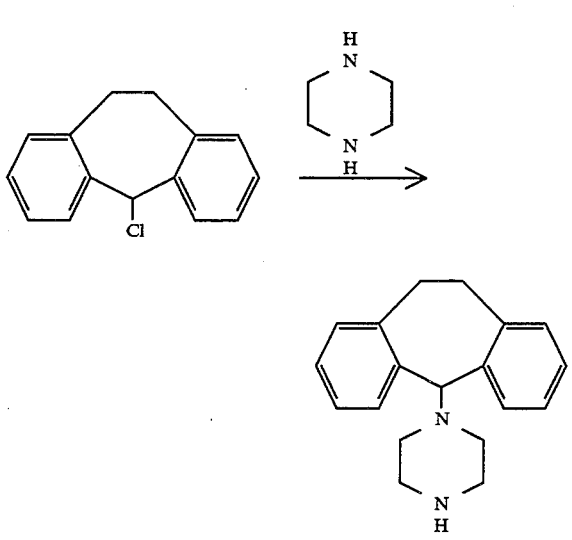

To a mixture of 15.26 g (0.177 mol) of piperizine in 130 mL of dry tetrahydrofuran at room temperature in under an atmosphere of nitrogen was added drop wise 2.34 g (0.0103 mol) of 5-chloro-10,11-dihydro-5H-dibenzo[a,d]cycloheptene in 20 mL of dry tetrahydrofuran. The reaction mixture was then allowed to stir at room temperature overnight. It was then poured into 1.0N aqueous sodium hydroxide and extracted with methylene chloride (3×). The combined organic portions were washed with brine, dried over magnesium sulfate, filtered, and concentrated in vacuo. The resultant product was precipitated from ethyl acetate/methanol/isopropyl ether and the less pure batches were then flash chromatographed. The chromatographed product was then recrystallized from ethyl acetate/methanol/isopropyl ether. A total of 1.537 g of the title compound was obtained as a white solid.

PREPARATIVE EXAMPLE 18

A. 1-METHYL-4-(10H-[1]BENZOTHI-OPYRANO[3,2-b]-10-HYDROXYPRIDINYL)-PIPERIDINE

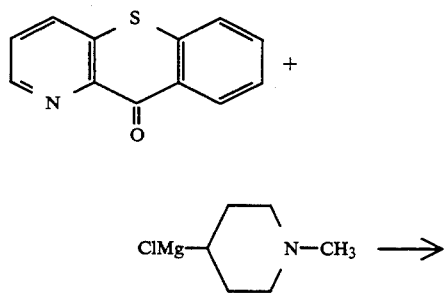

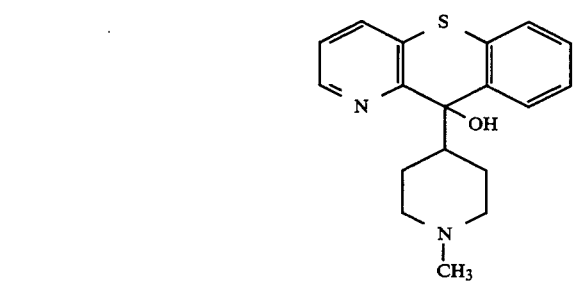

Suspend benzo[b]thiopyrano[2,3-b]-pyridin-10-one (1.3 g; 6.1 mmole) in dry tetrahydrofuran (30 mL) at room temperature and under an argon atmosphere. Add N-methyl-4-piperidinyl magnesium chloride (1.2 eq., 4.8 mL of 1.5M reagent in tetrahydrofuran), forming a dark solution. Stir at room temperature for 1 hour.

Quench the reaction with concentrated NH4Cl and extract with ethyl acetate. Wash the organic portions with brine and dry over Na2SO4. Remove the solvent and chromatograph the resultant liquid (5%→10% CH3OH/NH3 in CH2Cl2) to produce a yellowish solid which may be crystallized from pentane (0.80 g).

B. 1-METHYL-4-(10H-[1]BENZOTHI-OPYRANO[3,2-b]PYRIDIN-10-YLIDENE)PIPERIDINE

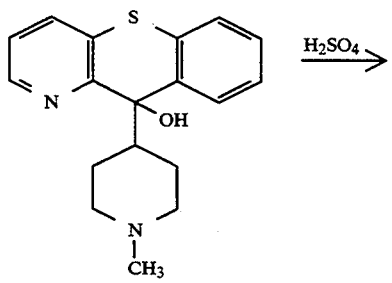

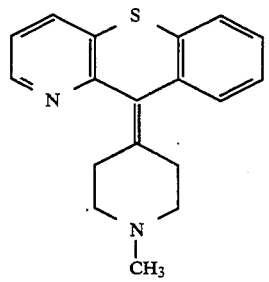

Warm the title compound of part A above (780 mg) in H2SO4 (85%, 20 mL) to 105° C. in an oil bath for 20 minutes. Pour the reaction mixture into ice water and basify with 25% aqueous NaOH. Extract with CH2Cl2 and wash the combined organic portions with brine. Dry over Na2SO4, filter and concentrate in vacuo to produce a yellowish glass (408 mg).

Purify with flash chromatography over (10%→15% CH3OH in CH2Cl2) to produce a yellowish glassy solid (290 mg).

C. 1-CYANO-4-(10H-[1]BENZOTHIOPYRANO[3,2-b]PYRIDIN-10-YLIDENE)PIPERIDINE

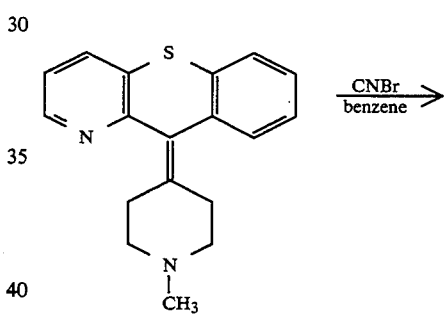

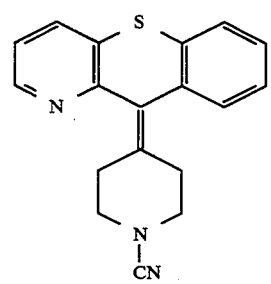

Add the title compound of part B above (291 mg) to a solution of cyanogen bromide (158 mg, 1.5 eq) in dry benzene (8.5 mL) at room temperature, and stir for 3 hours.

Remove the solvent under high vacuum to produce a solid and flash chromatograph (5% CH3OH in CH2Cl2) to produce the title compound as a yellowish solid (220 mg, m.p. 192°–193° C.).

D. 1-AMINOCARBONYL-1-(10H-[1]BENZOTHI-OPYRANO[3,2-b]PYRIDIN-10-YLIDENE)PIPERIDINE AND 4-(10H-[1]BENZOTHIOPYRANO[3,2-b]PYRIDIN-10-YLIDENE)PIPERIDINE

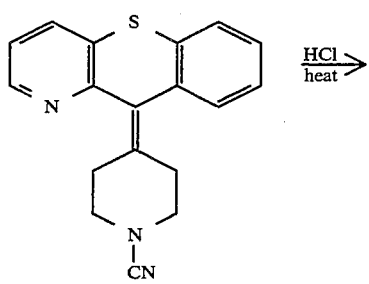

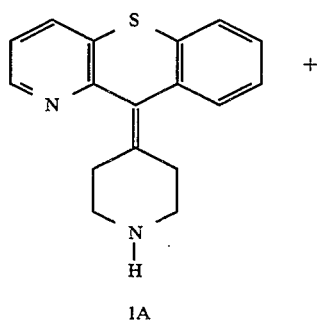

1A

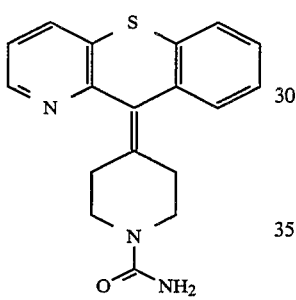

1B

Reflux a mixture of the title compound of part C above (210 mg) and 29% aqueous HCl (20 mL) for 24 hours. Pour the reaction mixture onto ice and basify with 25% aqueous NaOH. Extract the mixture with $CH_2Cl_2$ (2×200 mL) and wash the combined organic portions with brine. Dry over $Na_2SO_4$, filter and remove the solvent to yield a glassy solid.

Chromatography on $SiO_2$ (230–400 mesh), eluting with 10%→15% $CH_3OH$ in $CH_2Cl_2$ to yield the title compounds in two fractions; fraction 1 containing the N-H compound 1A as a yellowish solid (146 mg, m.p. 162°–163° C.), and fraction 2 containing the aminocarbonyl substituted compound 1B as an off-white solid (32 mg, m.p. 185°–187° C.).

PREPARATIVE EXAMPLE 19

A. 1-METHYL-4-(10H-[1]BENZOPYRANO[3,2-b]PYRIDIN-10-YLIDENE)PIPERIDINE

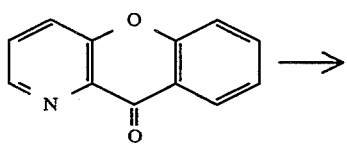

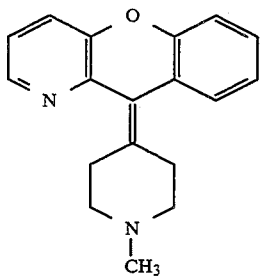

Prepare 1-methyl-4-(10H-[1]benzopyrano[3,2-b]pyridin-10-ylidene)piperidine, as described in U.S. Pat. No. 3,803,153.

B. 1-CYANO-4-(10H-[1]BENZOPYRANO[3,2-b]PYRIDIN-10-YLIDENE)PIPERIDINE

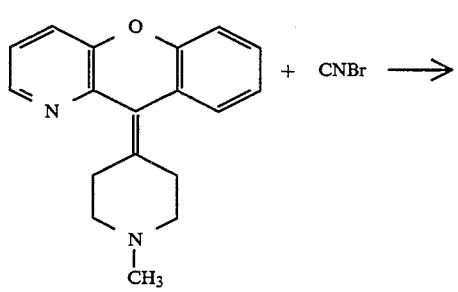

Stir a solution of cyanogen bromide (22.9 g, 0.196 mole) in dry benzene (300 mL) at room temperature, and add a solution of the title compound of part A above (54.5 g, 0.196 mole) in benzene (300 mL).

Filter the resulting solution after 3 hr. and concentrate to dryness to produce an off-white solid (44.0 g, m.p. 172°–175° C.).

Recrystallize the product from acetonitrile to afford the title compound.

C. 4(10H-[1]BENZOPYRANO[3,2-b]PYRIDIN-10-YLIDENE)PIPERIDINE

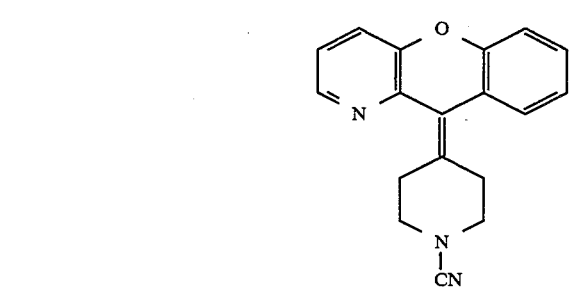

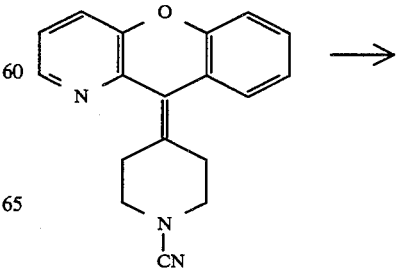

-continued

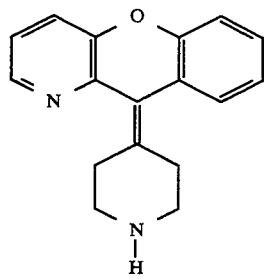

Reflux a mixture of the title compound from part B above (44.0 g, 0.152 mole), glacial acetic acid (1140 mL), conc. HCl (115 mL) and H₂O (760 mL) for 20 hours. Remove excess acetic acid and H₂O under reduced pressure, cool and basify with Na₂CO₃. Extract with chloroform and dry over Na₂SO₄. Filter, concentrate to dryness and chromatograph on silica gel using acetonitrile to produce the title compound (27.0 g, m.p. 158°–160° C.).

PREPARATIVE EXAMPLE 20

A. 3-(3-PHENYLPROPYL)PYRIDINE

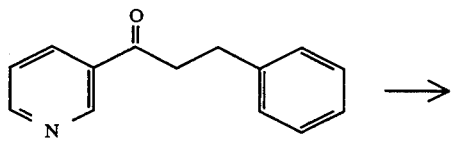

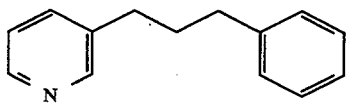

Heat a mixture of 2-phenylethyl 3-pyridinyl ketone (19.5 g, 0.092 mole), NaOH (8.0 g), hydrazine hydrate (8 mL, 85% in H₂O) and diethylene glycol (125 mL) to 240° C. for 4 hours.

Extract with benzene (1×), then diethyl ether (1×). Wash the combined organic extracts with H₂O (3×), remove the solvent and distill to produce the title compound (15.8 g, b.p. 130°–131° C. at 2 mmHg).

B. 3-(3-PHENYLPROPYL)PYRIDINE-N-OXIDE

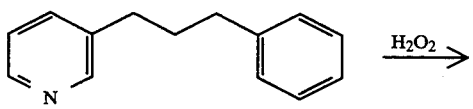

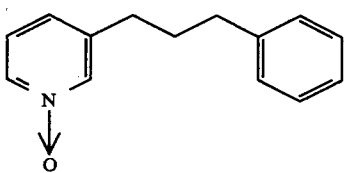

Add cold H₂O₂ (101 mL, 30%) to a cold solution of the title compound from part A above (166 g, 0.84 mole) in acetic acid (252 mL).

Heat to 60° C. for 24 hours and pour into ice water. Basify with NH₄OH, bringing the total volume to 2.0 L. The product separates out as an oil, which solidifies upon cooling. Filter and dissolve the filtrate in CHCl₃.

Remove the solvent and crystallize the product from benzene/hexane to produce the title compound (63.0 g, m.p. 34°–35° C.).

C. 2-CYANO-3-(PHENYL-N-PROPYL)PYRIDINE

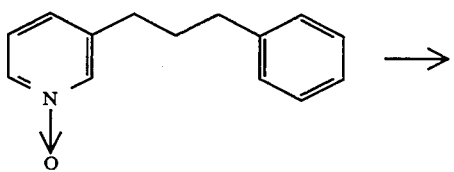

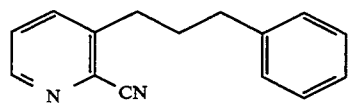

Add dimethyl sulfate (76 g, 0.6 mole) to the title compound from part B (171.5 g) and stir on a steam bath for 3 hours. Add H₂O (200 mL) and cool the solution, then add the solution dropwise to a solution of NaCN (92 g) in H₂O (260 mL) at 0° C. under a N₂ atmosphere. Allow the solution to remain at 0° C. for 4 hours, then stir the mixture for 12 hours at room temperature, while maintaining the reaction under an N₂ atmosphere. Extract the resultant brownish solution with CHCl₃. Concentrate the combined organic portions and purify via distillation. Crystallize the title compound from the appropriate fractions using benzene/pet ether (34.0 g, m.p. 50°–52° C.).

D. 12H-BENZO[B]-5,6,7,12-TETRAHYDROCYCLOOCTA[2,3-B]PYRIDIN-12-ONE

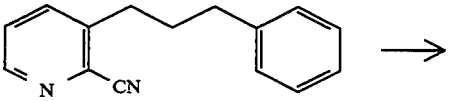

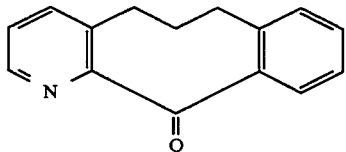

Stir the title compound from part C above (5.0 g) with polyphosphoric acid (250 g) while heating to 240° C., then reduce heat to 220° C. and maintain for 2 hours.

Pour the reaction mixture into ice water and basify with NaOH. Extract with diethyl ether and remove the solvent to form the title compound in crude form (4.0 g, m.p. 141°–145° C.) which may be recrystallized from 2-butanone to produce the title compound as a white solid (m.p. 153°–155° C.).

E. 1-METHYL-4-(5,6,7,12-TETRAHYDROBENZO[6,7]CYCLOOCTA[1,2-B]-12-HYDROXYPRIDINYL)PIPERIDINE

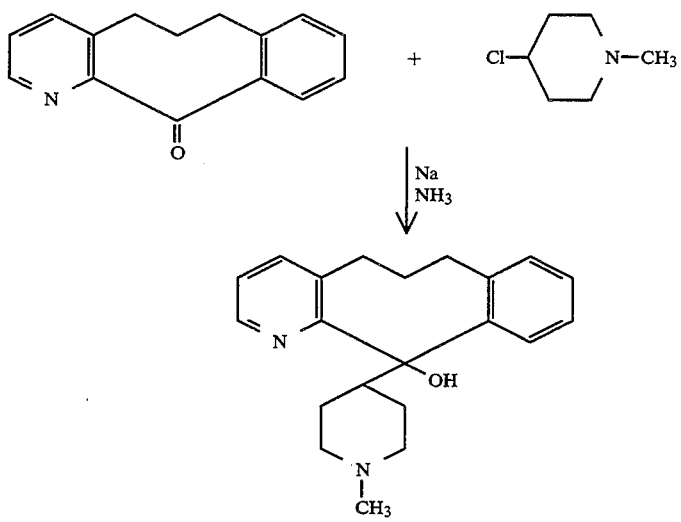

Dissolve sodium (2.7 g, 0.12 mole) in ammonia (200 mL) and stir for 20 minutes. Add the title compound from part D above, (13 g, 0.058 mole) in THF (105 mL) slowly and stir for 5 minutes. Add a solution of 4-chloro-1-methylpiperidine (7.8 g, 0.058 mole) in THF (25 mL) and continue stirring.

Add $NH_4Cl$ (5.0 g) and $NH_3$ (75 mL) and continue stirring for an additional 2 hours.

Concentrate the mixture to dryness, then partition over water and benzene. Extract with additional benzene. Remove the solvent to form a viscous tan residue.

Triturate the tan residue with pet ether and isopropyl ether. Cool the solution and decant off the liquids from the precipitate to obtain the title compound as a white solid (5 g, m.p. 122°–124° C.).

F. 1-METHYL-4-(5,6,7,12-TETRAHYDRO-BENZO[6,7]-CYCLOOCTA[1,2-B]PYRIDIN-12-YLIDENE)PIPERIDINE

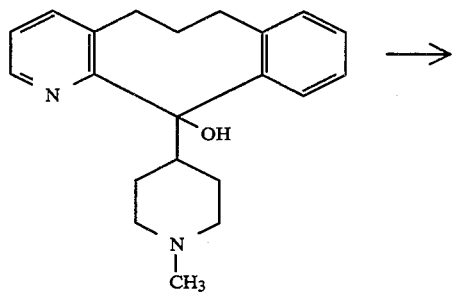

Combine the title compound from part E above (1.413 g) with acetic acid (12 mL), acetyl chloride (7 mL) and acetic anhydride (3.5 mL) and heat to 100° C. under an $N_2$ atmosphere.

After 3 hours concentrate the mixture in vacuo and pour the residue into NaOH (1N). Extract with $CH_2Cl_2$ (3×). Combine the organic portions, dry over $MgSO_4$, filter and rotary evaporate to dryness.

Purify by flash chromatography (5% $CH_3OH/NH_3$ in $CH_2Cl_2$) to produce the title compound which may be crystallized from pentane (1.014 g).

G. 1-(1,1,1-TRICHLOROETHOXYCARBONYL)-4-(5,6,7,12-TETRAHYDROBENZO[6,7]CYCLOOCTA[1,2-b]PYRIDIN-12-YLIDENE)PIPERIDINE

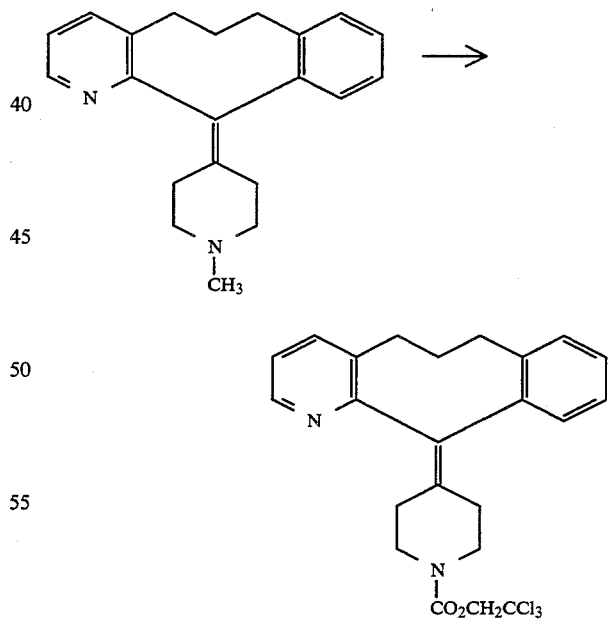

Combine the title compound from part F above (1.008 g, 3.31 mmol) with triethylamine (0.70 mL) and dry toluene (30 mL) at 90° C. under an argon atmosphere. Add dropwise 2,2,2-trichloroethylcarbonyl chloride (1.80 mL) over 20 minutes. Maintain the temperature at 90° C. for 1.67 hours, then cool to room temperature and pour into aqueous NaOH (1N). Extract the reaction mixture with $CH_2Cl_2$ (3×), combine the organic portions and dry over MgSO₄. Filter and rotary evaporate to dryness. Purify by flash chromatography (2% CH₃OH in CH₂Cl₂) and combine appropriate fractions to obtain the title compound.

H. 4-(5,6,7,12-TETRAHYDROBENZOCYCLOOCTA[1,2-b]PYRIDIN-12-YLIDENE)-PIPERIDINE

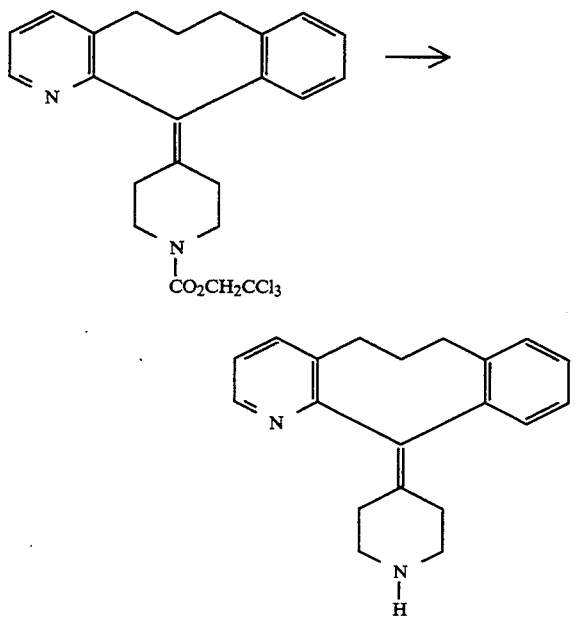

Combine the title compound from part G above and glacial acetic acid (20 mL) under an N₂ atmosphere at 90°–90° C. with zinc dust (2.12 g). After 3 hours, cool the reaction to room temperature, filter and rotary evaporate to dryness. Basify the residue with NaOH (1N) and extract with CH₂Cl₂ (4×). Combine the organic portions, dry over MgSO₄, filter and rotary evaporate to dryness. Purify by flash chromatography (5%→7% CH₃OH/NH₃ in CH₂Cl₂) and collect the appropriate fractions to yield the title compound as a glass (603 mg).

PREPARATIVE EXAMPLE 21

A. 2-CYANO-3-(BROMOMETHYL)PYRIDINE

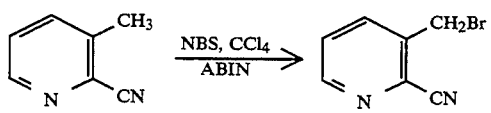

Combine 2-cyano-3-methylpyridine (11.8 g), N-bromosuccinimide (NBS) (26.8 g, 1.5 eq.) and aza(bis-)isobutyronitrile (ABIN) (180 mg) in dry CCl₄ (300 mL). Reflux the mixture overnight.

Pour the mixture into water, basify with NaOH and extract with CH₂Cl₂. Wash the organic portion with water, dry (Na₂SO₄), filter and concentrate to obtain a liquid. Chromatograph the product, eluting with 30% diethyl ether in hexanes. Combine the appropriate fractions to obtain the mono bromo compound (5.01 g) as a yellowish solid: m.p. 41.5°–42.5° C.

B. 2-CYANO-3-(3-CHLOROPHENOXYMETHYL)-PYRIDINE

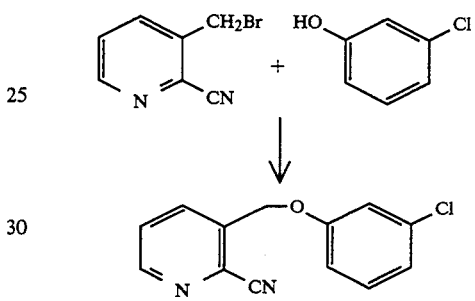

Stir a solution of the title compound of part A above (0.71 g, 3.6 mmol), NaI (54 mg, 0.1 eq) and Cs₂CO₃ (1.17 g, 1.0 eq) in dry acetone (17 mL, dried over MgSO₄) at room temperature for 5 minutes, then add 3-chlorophenol (463 mg) via a syringe.

Reflux over an oil bath for 4.5 hours.

Filter and wash the filtrate with dry acetone. Concentrate the filtrate, suspend in diethyl ether, and refilter to obtain a brown solid which is the title compound in crude form. Triturate with pentane, and resuspend in diisopropyl ether (40 mL) with charcoal, and heat on a steam bath.

Filter and evaporate the solvent to obtain the title compound, which crystallizes to form a white solid (640 mg): m.p. 70°–72° C.

C. 8-CHLORO-5,11-DIHYDRO[1]BENZOXEPINO[4,3-B]PYRIDIN-11-ONE

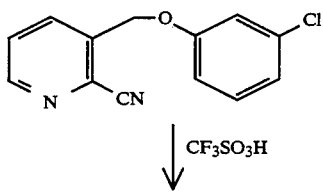

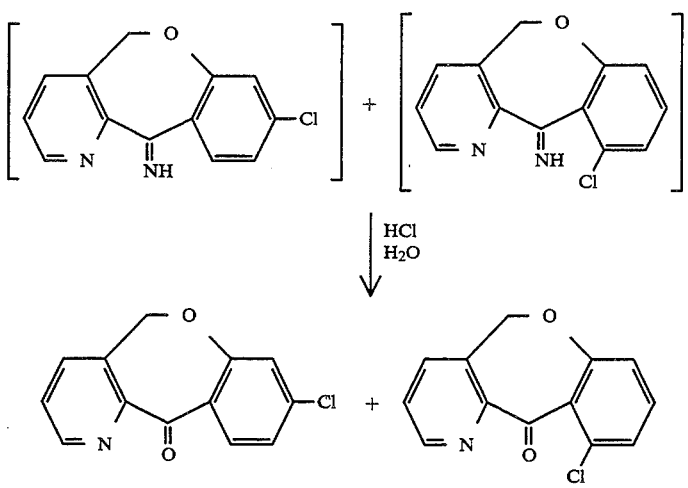

Stir the title compound from part B above (6.1 g) in CF$_3$SO$_3$H (60 mL) at room temperature for 3 hours. Upon completion, quench with H$_2$O and conc. HCl (30%) and continue stirring for 0.5 hours.

Warm to 35° C. for 0.5 hours. Basify with NaOH (25%) and extract with CH$_2$Cl$_2$ (2×). Wash with brine (2×), filter and dry over Na$_2$SO$_4$, and concentrate in vacuo to afford a semi-solid.

Triturate the resulting semisolid (6.35 g) with diisopropyl ether and separate the isomers via flash chromatography (30% ethyl acetate in hexanes). Combine the appropriate fractions to obtain the title compound as a solid (4.902 g): m.p. 139.5°–140.5° C., and the 10-chloro compound as a solid (498 mg): m.p. 100°–102° C.

D. 1-METHYL-4-(8-CHLORO-11-HYDROXY5,11-DIHYDRO[1]-BENZOXEPINO[4,3-b]PYRIDINYL)PIPERIDINE

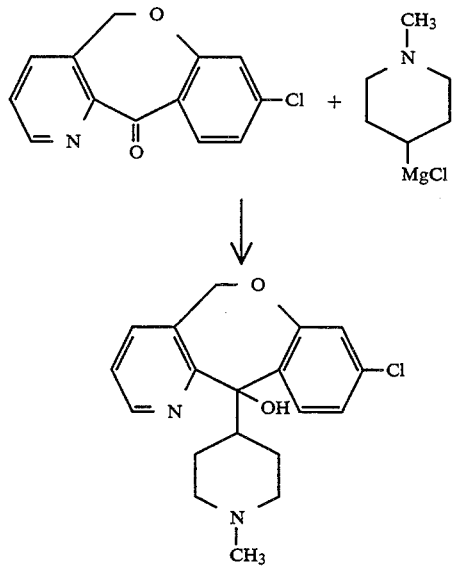

Slowly add the Grignard reagent (11.9 mL, 1.2M) derived from N-methyl-4-chloropiperidine to a stirred solution of the title compound from part C above (3.47 g) in dry tetrahydrofuran (37 mL). Stir the solution for 30 minutes after the addition.

Quench the reaction with ice and NH$_4$Cl. Extract the solution with CH$_2$Cl$_2$ (2×), dry, filter and concentrate to obtain the title compound. Chromatograph the product on silica gel eluting with 5→7.5% CH$_3$OH/NH$_3$ in CH$_2$Cl$_2$ to obtain the title compound as a glass (2.56 g): MS (EI) m/e 344 (M+).

E. 1-METHYL-4-(8-CHLORO-5,11-DIHYDRO[1-]BENZOXEPIN[4,3-b]PYRIDIN-11-YLIDENE)-PIPERIDINE

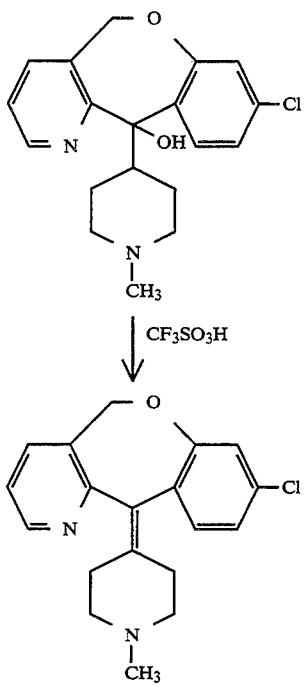

Stir the title compound from part D above (934 mg) in CF$_3$SO$_3$H (20 mL) at room temperature for 15 minutes. Raise temperature to 45° C. on an oil bath and maintain for 1.25 hours. Cool to room temperature and pour the mixture into ice water. Basify with dilute NaOH, and extract with CH$_2$Cl$_2$ (2×). Wash with brine (1×) and dry over Na$_2$SO$_4$ to obtain the title compound as a brown glass.

Purify by combining with charcoal in ethyl acetate, then filter and remove solvent to obtain a yellowish brown solid.

Recrystallize from ethyl acetate and diisopropyl ether to obtain the title compound as an off-white solid (540 mg): m.p. 168°–170° C.

F. 1-ETHOXYCARBONYL-4-(8-CHLORO-5,11-DIHYDRO[1]-BENZOXEPINO[4,3-b]PYRIDIN-11-YLIDENE)PIPERIDINE

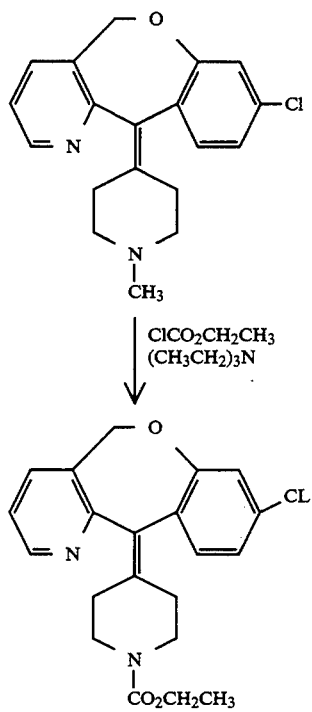

Dissolve the title compound from part E above (474 mg, 1.45 mmol) in toluene (10 mL) and add triethylamine (0.656 mL). Warm and maintain the reaction at 80°–85° C. and slowly add ethyl chloroformate (1.242 mL). Maintain the reaction at 80°–85° C. while stirring for 3 hours.

Quench the reaction with H₂O and extract with ethyl acetate (2×100 mL). Wash with brine, separate and dry over Na₂SO₄. Remove the solvent and purify via flash chromatograph, eluting with 40→60% ethyl acetate in hexanes to yield the title compound as an off-white solid, which may be purified by trituration with pentane and diisopropyl ether to render a powder (428 mg): m.p. 118°–120° C.

G. 4-(8-CHLORO-5,11-DIHYDRO[1]BENZOXEPINO[4,3-b]PYRIDIN-11-YLIDENE)PIPERIDINE

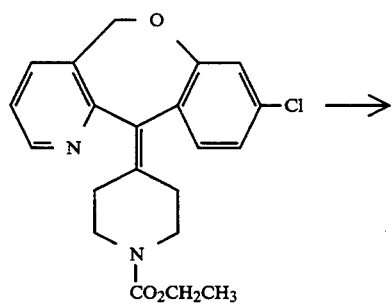

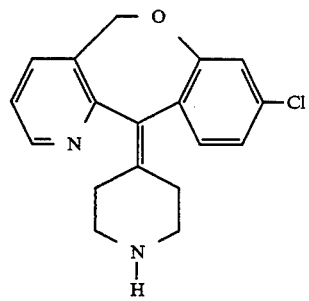

Dissolve the title compound from part F above (333.8 mg) in ethanol (5 mL) and add 14% aqueous KOH. Reflux under an argon atmosphere for 19 hours.

Quench the reaction with H₂O and extract with CH₂Cl₂ (3×100 mL). Wash with brine (1×100 mL), dry over Na₂SO₄ and filter. Remove the solvent to yield a glassy off-white solid.

Recrystallize with ethyl acetate/diisopropyl ether to yield the title compound as a white powder (161.5 mg): m.p. 166°–176° C. (dec).

PREPARATIVE EXAMPLE 22

A. 2-CYANO-3-(3-CHLOROPHENYLTHIOMETHYL)PYRIDINE

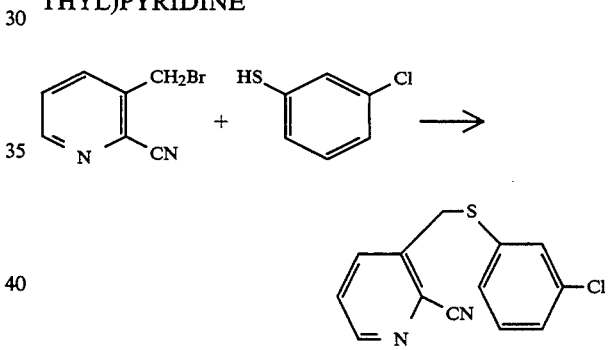

To a stirred, cloudy solution of sodium methoxide (14.7 g, 0.27 mol) in methanol (450 mL), contained in a water bath, add a solution of 3-chlorothiophenol (39.5 g, 0.27 mol) in methanol (95 mL). To the resultant solution add a solution of the title compound of Part A above (48.9 g, 0.25 mol) in methanol (195 mL), and stir the reaction mixture at room temperature for 1 h.

Concentrate the reaction mixture under reduced pressure, add 500 mL of ether to the residue, stir, and filter to remove sodium bromide. Evaporate ether under reduced pressure to obtain the title compound as an amber oil, which may be used without further purification.

B. 8-CHLORO-5,11-DIHYDRO[1]BENZOTHIEPINO[4,3-b]PYRIDIN-11-ONE

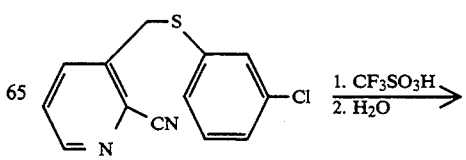

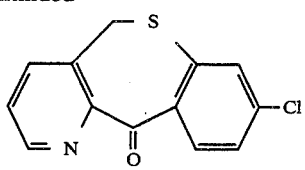

Stir a solution of the title compound from Part A above (49.7 g, 0.19 mol) in trifluoromethanesulfonic acid (500 mL) for 3.5 h at 95° C. Allow the reaction mixture to cool below 60° C. and pour onto crushed ice (1500 mL). Stir the mixture for 0.5 h and add sufficient aqueous sodium hydroxide (220 mL of 50% solution) to raise the pH to 9.

Extract the aqueous solution with ethyl acetate (1×), saturate with sodium chloride, and extract again (2×) with ethyl acetate. Wash the combined organic extracts with brine (3×), filter, and dry over anhydrous MgSO$_4$.

Filter and remove the solvent under reduced pressure. Chromatograph the residual material on silica gel, eluting with ethyl acetate-hexanes (3:2), to obtain the title ketone as a tan solid, m.p. 186°–187° C.

C. 1-METHYL-4-(8-CHLORO-11-HYDROXY-5,11-DIHYDRO[1]BENZOTHIEPINO[4,3-b]PYRIDINYL)PIPERIDINE

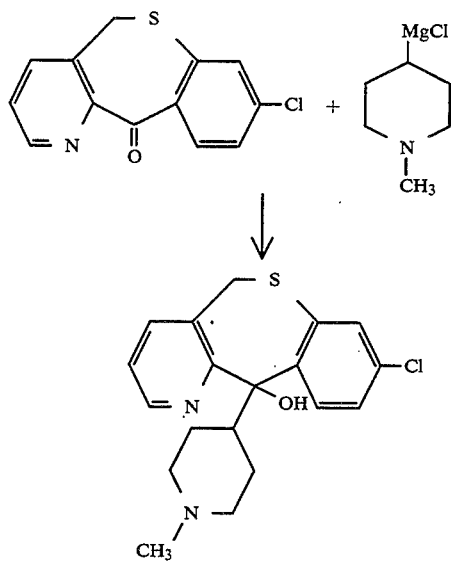

With cooling in an ice-water bath, add a suspension of the title ketone from Part B above (13.4 g, 51.2 mmol) in dry tetrahydrofuran (52 mL) to a stirred solution (55 mL of approximately 1M) in THF of the Grignard reagent derived from 1-methyl-4-chloropiperidine. Stir the resultant mixture for 1 h at room temperature.

Quench the reaction by cooling the mixture to 10° C. in an ice-water bath and adding saturated aqueous ammonium chloride solution (50 mL). Add methylene chloride (100 mL), and stir the mixture for a few minutes. Filter the mixture through Celite, and wash the filter cake with methylene chloride. Combine the original filtrate and washes, separate the methylene chloride phase, and extract the aqueous phase (2×) with additional methylene chloride. Combine the organic extracts, wash with brine (2×75 mL), and dry over anhydrous sodium sulfate. Filter, strip the filtrate under reduced pressure, and chromatograph the residue on silica gel, eluting with methylene chloride-methanol-ammonium hydroxide (90:9:0.5), to obtain the title compound as an off-white to pale pink solid with m.p. 158.5°–159.5° C.

D. 1-METHYL-4-(8-CHLORO-5,11-DIHYDRO[1]BENZOTHIEPINO[4,3-b]PYRIDIN-11-YLIDENE)PIPERIDINE

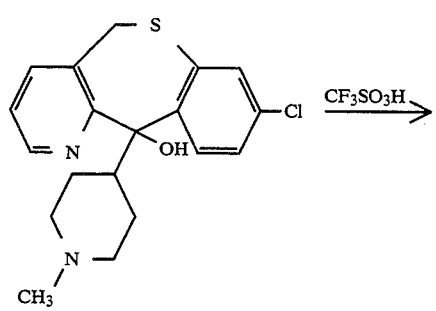

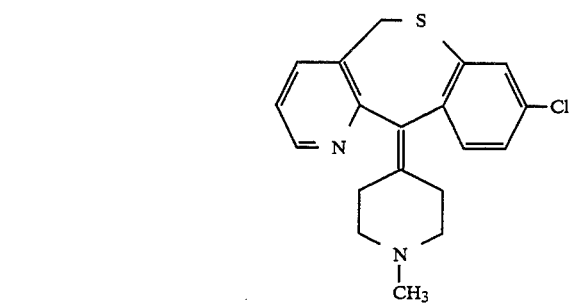

Heat a solution of the title compound from Part C, above (5.04 g, 13.9 mmol) in trifluoromethanesulfonic acid at 45° C. for 10.5 h. Cool the reaction solution to room temperature, and pour it into a stirred ice-water mixture. Maintain cooling in an ice-water bath, and add with stirring aqueous sodium hydroxide (130 mL of a 50% solution). Extract the solution with methylene chloride (3×), wash the combined extracts successively with water (2×) and brine (1×), dry over anhydrous sodium sulfate, and evaporate solvent under reduced pressure. Purify the residual glass by chromatographing on silica gel, eluting with methyene chloride-methanol-ammonium hydroxide (90:9:0.25), and triturating the solid in acetonitrile. Filter to obtain the title compound as a light tan solid, containing 0.08 mole methylene chloride, m.p. 175°–177° C.

E. 1-ETHOXYCARBONYL-4-(8-CHLORO-5,11-DIHYDRO[1]BENZOTHIEPINO[4,3-b]PYRIDIN-11-YLIDENE)PIPERIDINE

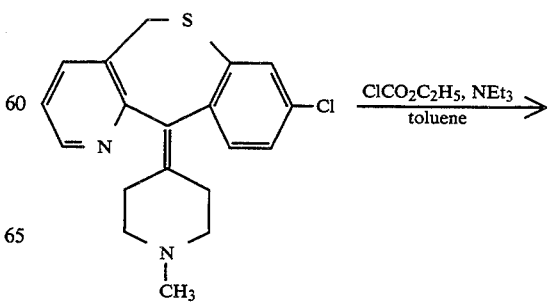

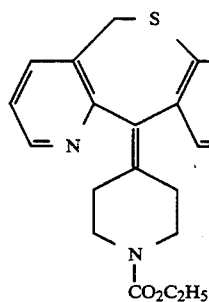

To a stirred solution of the title compound from Part D above (1.44 g, 4.2 mmol) and triethylamine (966 mg, 9.5 mmol) in dry toluene (27 mL), maintained at 80° C., add dropwise ethyl chloroformate (2.78 g, 25.6 mmol). After one hour, add more triethylamine (480 mg, 4.7 mmol), and continue heating at 80° C. for an additional hour.

Cool the reaction mixture to 50° C., add ethyl acetate (15 mL), wash successively with water (2×) and brine (1×), and dry over anhydrous magnesium sulfate. Filter, evaporate the filtrate under reduced pressure, and purify by chromatographing the residual solid on silica gel. Elute first with ethyl acetate-hexanes (9:1); then rechromatograph the partially purified material with ethyl acetate-hexanes (1:1) to obtain the title compound as an off-white solid with m.p. 154°–157° C.

F. 4-(8-CHLORO-5,11-DIHYDRO[1]BENZO-THIEPINO[4,3-b]PYRIDIN-11-YLIDENE)PIPERIDINE

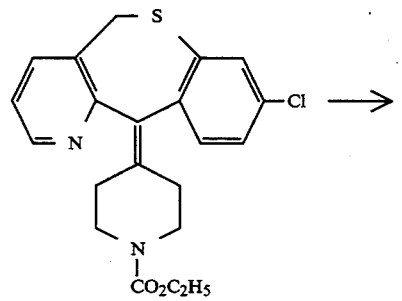

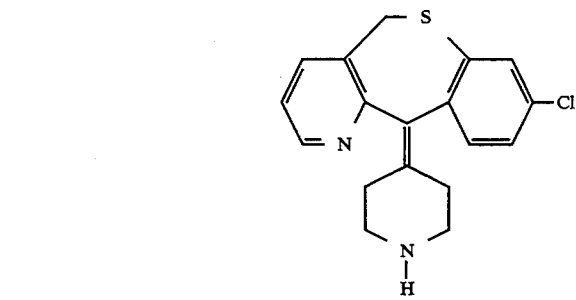

Reflux for 21.5 h in an inert gas atmosphere a solution of the title compound from Part E above (720 mg, 1.87 mmol) and potassium hydroxide (2.0 g, 35.6 mmol) in ethanol (20 mL) and water (2 mL).

Cool to room temperature, dilute with methylene chloride (20 mL), and wash successively with water (4×) and brine (1×). Dry the solution over anhydrous sodium sulfate, filter, and evaporate the filtrate under reduced pressure to obtain the title compound as an off-white solid, m.p. 206.5°–215° C.

PREPARATIVE EXAMPLE 23

A. 8-CHLORO-5,11-DIHYDRO[1]BENZOXEPINO[4,3-b]PYRIDIN-11-OL

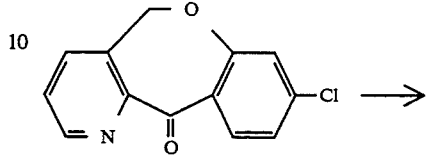

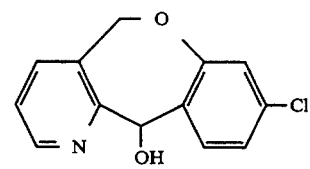

Add sodium borohydride (0.96 g, 25.4 mmole) to 8-chloro-[1]-benzoxepino[4,3-b]pyridin-11-one (10.00 g, 40.7 mmole) in ethanol (100 mL). Stir for 18 hours at room temperature. Add water (100 mL), and concentrate in vacuo. Add additional water (100 mL), and extract with dichloromethane. Wash the organic solution with saturated NaCl, dry with MgSO₄, filter, and concentrate in vacuo. Dissolve the oil in dichloromethane, and chromatograph on silica gel, eluting with 50% ethyl acetate-hexane. Combine the appropriate fractions, and concentrate under reduced pressure to give a white solid (8.50 g, 84% yield): mp 105°–108° C.; MS (EI) m/e 249 (M+).

B. 8,11-DICHLORO-5,11-DIHYDRO[1]BENZOXEPINO[4,3-b]PYRIDINE

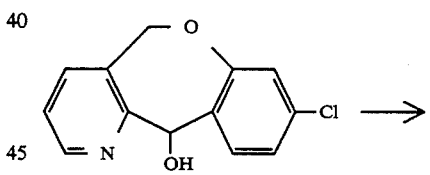

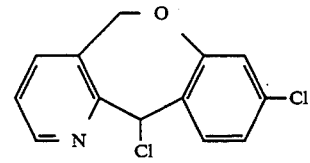

Add thionyl chloride (2.74 mL, 4.48 g, 37.6 mmole) to 8-chloro-5,11-dihydro[1]benzoxepino[4,3-b]pyridin-11-ol (8.48 g, 34.2 mmole) in dichloromethane (100 mL) at 0° C. under a nitrogen atmosphere. Stir for 30 minutes at 0° C., and then stir for 60 minutes at room temperature. Add iced 1.5N NaOH (100 mL), and separate layers. Extract aqueous solution with dichloromethane (2×100 mL). Wash the combined organic solution with water and saturated NaCl, dry with MgSO₄, filter, and concentrate in vacuo to give a reddish-black oil (8.82 g, 97% yield).

C. 8-CHLORO-5,11-DIHYDRO-11-(1-PIPERAZINYL)[1]BENZOXEPINO[4,3-b]PYRIDINE

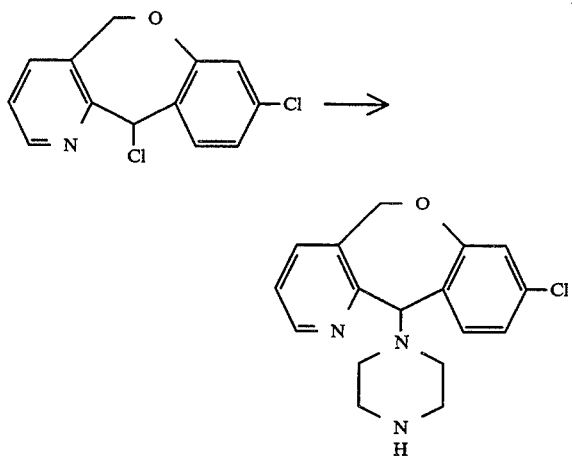

Add 8,11-dichloro-5,11-dihydro[1]benzoxepino[4,3-b]pyridine (8.81 g, 0.033 mole) in dry tetrahydrofuran (150 mL) dropwise via addition funnel to piperazine (33.37 g, 0.387 mole) in dry tetrahydrofuran (300 mL) under a nitrogen atmosphere. Stir for 4 hours at room temperature, and concentrate in vacuo. Add iced 1.5N NaOH (200 mL), and extract with ethyl acetate (3×125 mL). Wash the organic solution with water and saturated NaCl, dry with MgSO4, filter, and concentrate in vacuo. Dissolve the oil in dichloromethane, and chromatograph on silica gel, eluting with 90:9:1 dichloromethane:methanol:NH4OH. Combine the appropriate fractions, and concentrate under reduced pressure to give a tan solid (6.41 g, 61% yield): mp 162°-164° C.; MS (Cl) m/z 316 (M+).

PREPARATIVE EXAMPLE 24

A. 8-CHLORO-5,11-DIHYDRO[1]BENZOTHIEPINO[4,3-b]PYRIDIN-11-OL

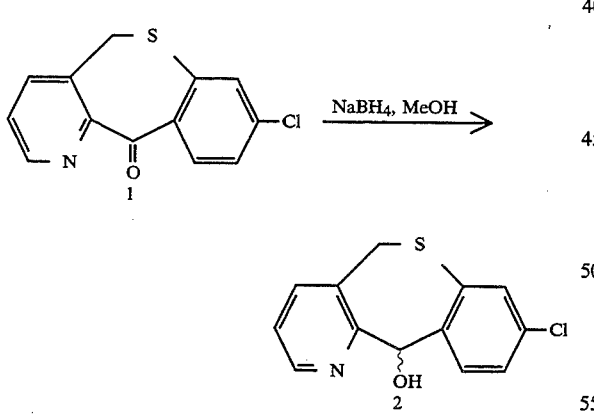

Sodium borohydride (2.60 g, 0.0688 mol) was added portion wise over 15 minutes to a stirred suspension of 8-chloro-5,11-dihydro[1]benzothiepino[4,3-b]pyridin-11-one (15.0 g, 0.0573 mol) in methanol (150 mL) at 25°-35° C. and under an atmosphere of nitrogen. The mixture was then stirred for 40 minutes at 25°-30° C. It was concentrated in vacuo to provide a suspension, after which it was poured into water (150 mL), and extracted with CH2Cl2 (3×100 mL). The combined extracts were washed with water (3×75 mL), dried over Na2SO4, filtered, and concentrated in vacuo. The crude product (18.4 g) was flash chromatographed and eluted with EtOAc:hexanes (1:1) to give the title compound (9.70 g, 64% yield).

B. 8,11-DICHLORO-5,11-DIHYDRO[1]BENZOTHIEPINO[4,3-b]PYRIDINE

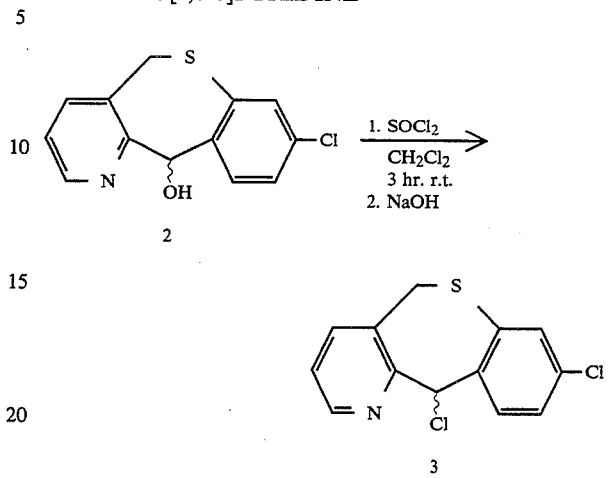

Thionyl chloride (3.1 mL, 0.0425 mol) was added dropwise to a stirred suspension of 8-chloro-5,11-dihydro[1]benzothiepino[4,3-b]pyridin-11-ol (8.8 g, 0.0334 mol) in CH2Cl2 (75 mL) at 3°-8° C. After the mixture was stirred at room temperature for 3 hours, it was poured into 150 mL of 2.5M NaOH containing ice. It was then filtered, separated and the aqueous layer extracted with CH2Cl2 (2×50 mL). The combined organic extracts were washed with water (3×50 mL) and brine (1×75 mL). It was dried over MgSO4, filtered, and concentrated in vacuo to give the title compound (8.0 g, 80%).

C. 8-CHLORO-5,11-DIHYDRO-11-(1-PIPERAZINYL)-[1]BENZOTHIEPINO[4,3-b]PYRIDINE

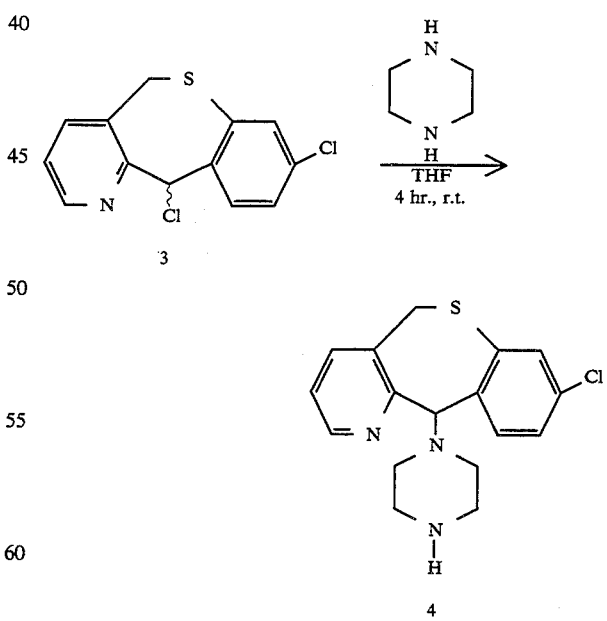

A solution of 8,11-dichloro-5,11-dihydro[1]benzothiepino-4,3-b]pyridine (8.15 g, 0.029 mol) in tetrahydrofuran (100 mL) was added at 18°-19° C. to a stirred suspension of piperazine (28.9 g, 0.34 mol) in tetrahydrofuran (290 mL) over 20 minutes. The mixture was stirred for 4 hours at room temperature and then poured into 2.5M aqueous NaOH (250 mL) containing ice. After separation of the layers, the aqueous portion was extracted with EtOAc (3×100 mL). The combined organic portions were washed with H₂O (3×75 mL) and brine (150 mL). After drying over MgSO₄, the filtered organic layer was concentrated in vacuo to give the crude product (8.9 g). Purification of the crude product via flash chromatography (9:1:0.125 CH₂Cl₂:MeOH:NH₄OH) gave the title compound (7.6 g, 78% yield).

PREPARATIVE EXAMPLE 25

A. 9-CHLOROFLUORENE

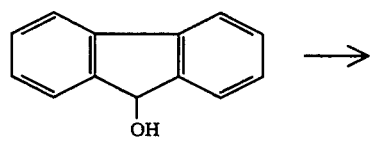

To a cold (0° C.) suspension of 9-hydroxyfluorene (49 g) in benzene (650 mL) was added thionylchloride (70 mL). This solution was allowed to stir while warming up to room temperature overnight. The benzene was distilled off and the product was recrystallized from isopropylether to give 41 g of the title compound as a while solid: m.p. 87°–89° C.

B. 1-(9H-FLUOREN-9-YL)-PIPERAZINE

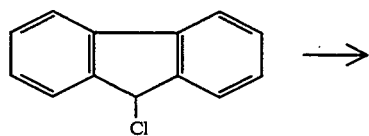

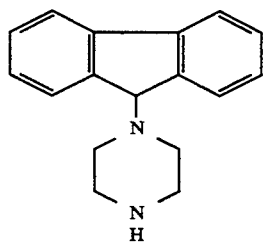

A solution of 9-chlorofluorene (8.4 g), triethylamine (0.85 mL) and piperazine (27 g) in THF (200 mL) was refluxed under argon for 6 hours. It was then filtered and the solvent was removed under vacuum. The crued product was washed with water, chromatographed on silica gel and eluted with 5% MeOH saturated with NH₃ in CH₂Cl₂ to afford the title compound (8.5 g).

EXAMPLE 1

8-CHLORO-6,11-DIHYDRO-11-[1-(4-PYRIDINYL-METHYL)-4-PIPERIDINYLIDENE]-5H-BEN-ZO[5,6]CYCLOHEPTA[1,2-b]PYRIDINE

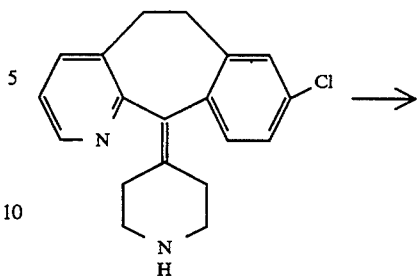

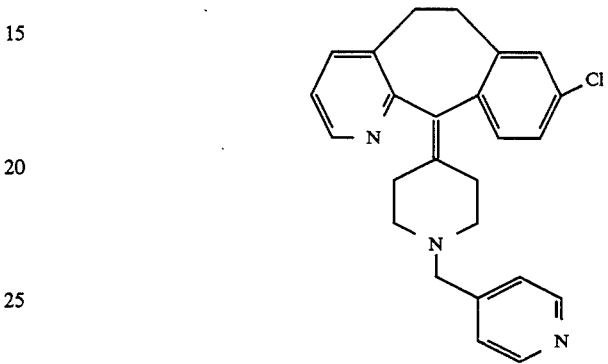

To a mixture of 527 mg (3.22 mmol) of 4-picolyl chloride hydrochloride in 20 mL of dry tetrahydrofuran at room temperature and under a nitrogen atmosphere was added 0.90 mL (6.43 mmol) of triethylamine. The mixture was cooled to 0° C. and 1.00 g (3.22 mmol) of 4-(8-chloro-5,6-dihydro-11H-benzo[5,6]cyclohepta[1,2-b]pyridin-11-ylidene)piperidine was added. The mixture was warmed to room temperature and allowed to stir overnight. Another 528 mg (3.22 mmol) of 4-picolyl chloride hydrochloride was then added followed by 450 μL (3.22 mmol) of triethylamine. After 4.5 hours the reaction mixture was then poured into 1.0N aqueous sodium hydroxide and extracted with ethyl acetate (3×). The combined organic portions were washed with brine, dried over magnesium sulfate, filtered and concentrated in vacuo. The residue was flashed chromatographed (4% methanol saturated with ammonia in methylene chloride) to provide 322 mg of the title compound as a glass: MS (FAB) m/z 402 (M⁺+1).

EXAMPLE 2

8-CHLORO-6,11-DIHYDRO-11-[1-(4-PYRIDINYL-METHYL)-4-PIPERIDINYLIDENE]-5H-BEN-ZO[5,6]CYCLOHEPTA[1,2-b]PYRIDINE, N-OXIDE

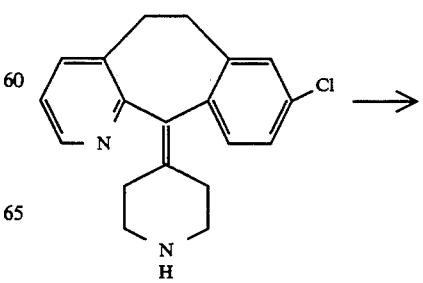

-continued

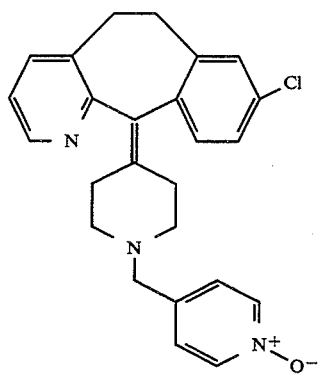

To a mixture of 104 mg (0.835 mmol) of 4-pyridylcarbinol N-oxide and 335 μL (2.40 mmol) of triethylamine in 7 mL of dry methylene chloride at 0° C. and under a nitrogen atmosphere was added 93 μL (1.2 mmol) of methanesulfonyl chloride. After one hour 250 mg (0.808 mmol) of 4-(8-chloro-5,6-dihydro-11H-benzo[5,6]cyclohepta[1,2-b]pyridin-11-ylindene)piperidine was added. The reaction mixture was allowed to stir at room temperature for one hour and then was refluxed overnight. It was then poured into 1.0N aqueous sodium hydroxide and extracted with ethyl acetate (3×). The combined organic portions were washed with brine, dried over magnesium sulfate, filtered and concentrated in vacuo. The residue was flashed chromatographed (5% methanol saturated with ammonia in methylene chloride) to provide 73 mg of the title compound as a glass: MS (FAB) m/z 418(M+ +1).

EXAMPLE 3

A. (±)-8-CHLORO-6,11-DIHYDRO-11-[4-(4-PYRIDINYLMETHYL)-1-PIPERAZINYL]-5H-BENZO[5,6]CYCLOHEPTA[1,2-b]PYRIDINE, N-OXIDE

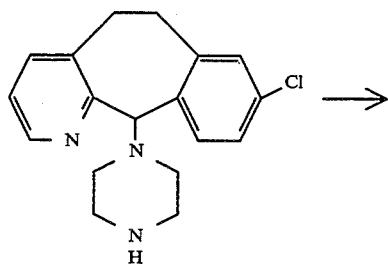

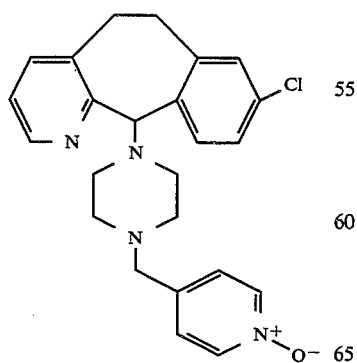

To a mixture of 1.204 g (9.63 mmol) of 4-pyridylcarbinol N-oxide and 2.7 mL (19.4 mmol) of triethylamine in 90 mL of dry methylene chloride at 0° C. and under a nitrogen atmosphere was added over 10 minutes 742 μL (9.59 mmol) of methanesulfonyl chloride. After 20 minutes, 833 mg (9.60 mmol) of lithium bromide followed by 3.01 g (9.60 mmol) of 8-chloro-6,11-dihydro-11-(4-piperazinyl)-5H-benzo[5,6]cyclohepta-[1,2-b]pyridine was added and the reaction mixture was refluxed for 4.75 hours. It was poured into 1.0N aqueous sodium hydroxide and extracted with methylene chloride (3×). The combined organic portions were washed with brine, dried over magnesium sulfate, filtered and concentrated in vacuo. The residue was purified via flash chromatography (10% methanol saturated with ammonia in methylene chloride) to provide 1.97 g of the title compound as a glass: MS (CI) m/e 421 (M+ +1).

B. (+)-8-CHLORO-6,11-DIHYDRO-11-[4-(4-PYRIDINYLMETHYL)-1-PIPERAZINYL]-5H-BENZO[5,6]CYCLOHEPTA-[1,2-b]PYRIDINE, N-OXIDE AND (−)-8-CHLORO-6,11-DIHYDRO-11-[4-(4-PYRIDINYLMETHYL)-1-PIPERAZINYL]-5H-BENZO[5,6]CYCLOHEPTA[1,2-b]PYRIDINE, N-OXIDE,

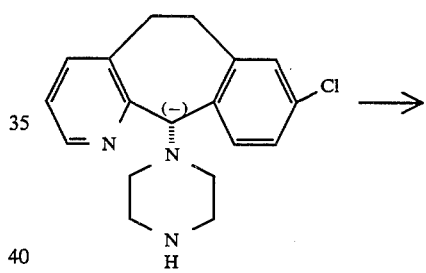

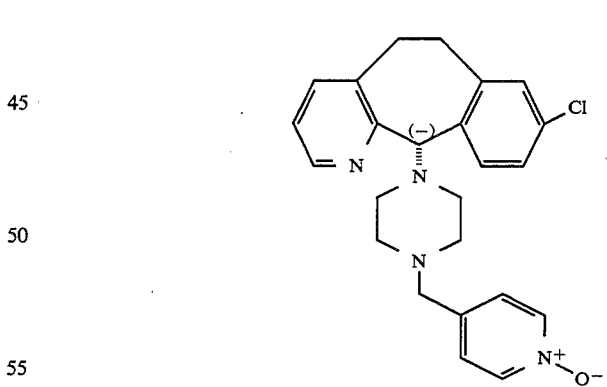

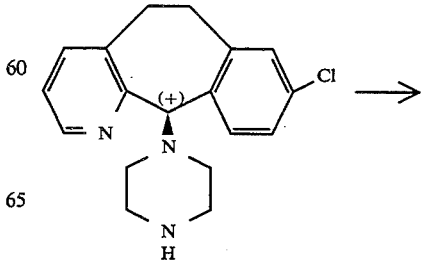

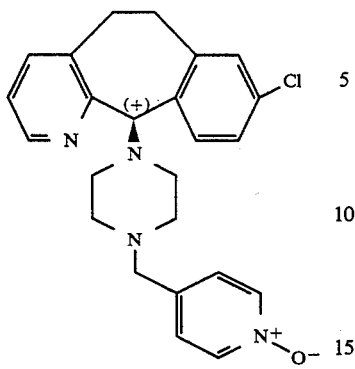

Step B1. To a mixture of 213 mg (1.70 mmol) of 4-pyridylcarbinol N-oxide and 563 mg (1.70 mmol) of carbon tetrabromide in 14 mL of dry methylene chloride at room temperature and under an argon atmosphere was added in one portion 446 mg (1.70 mmol) of triphenylphosphine. After 45 minutes, 313 mg (0.997 mmol) of (+)-8-chloro-6,11-dihydro-11-(4-piperazinyl)-5H-benzo[5,6]cyclohepta-[1,2-b]pyridine was added followed by 237 mL (1.78 mmol) of triethylamine. The reaction mixture was then allowed to stir at room temperature overnight, after which it was taken up in methylene chloride and washed once with 0.5M aqueous sodium bicarbonate and then brine. The organic portion was dried over sodium sulfate, filtered and concentrated in vacuo. The residue was purified via flash chromatography (5% methanol saturated with ammonia in methylene chloride) to provide 305 mg of (+)-8-chloro-6,11-dihydro-11-[4-(4-pyridinylmethyl)-1-piperazinyl]-5h-benzo[5,6]cyclohepta-[1,2-b]pyridine, N-oxide as a glass: MS (CI) m/z 421 (M$^+$+1);

$[\alpha]^{26}_D = +44.5°$.

Step B2. To a mixture of 188 mg (1.50 mmol) of 4-pyridylcarbinol N-oxide and 497 mg (1.50 mmol) of carbon tetrabromide in 12 mL of dry methylene chloride at room temperature and under an argon atmosphere was added in one portion 393 mg (1.50 mmol) of triphenylphosphine. After 40 minutes, 313 mg (0.997 mmol) of (−)-8-chloro-6,11-dihydro-11-(4-piperazinyl)-5H-benzo[5,6]cyclohepta-[1,2-b]pyridine was added followed by 209 mL (1.57 mmol) of triethylamine. The reaction mixture was then allowed to stir at room temperature for 3 hr, after which it was taken up in methylene chloride and washed once with 0.5M aqueous sodium bicarbonate and then brine. The organic portion was dried over sodium sulfate, filtered and concentrated in vacuo. The residue was purified via flash chromatography (4% methanol saturated with ammonia in methylene chloride) to provide 183 mg of (−)-8-chloro-6,11-dihydro-11-[4-(4-pyridinylmethyl)-1-piperazinyl]-5h-benzo[5,6]cyclohepta-[1,2-b]pyridine, N-oxide as a glass: MS (CI) m/z 421 (M$^+$+1);

$[\alpha]^{26}_D = -44.0°$.

EXAMPLE 4

4-[[4-(5H-DIBENZO[a,d](CYCLOHEPTEN-5-YLIDENE)-1-PIPERIDINYL]METHYL]PYRIDINE, 1-OXIDE

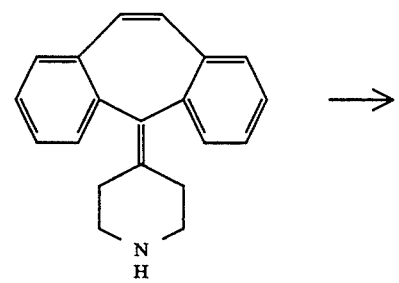

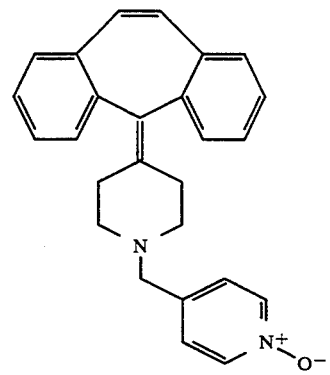

To a mixture of 203 mg (1.6 mmol) of 4-pyridylcarbinol N-oxide and 650 µL (4.66 mmol) of triethylamine in 10 mL of dry methylene chloride at 0° C. and under a nitrogen atmosphere was added 180 µL (1.8 mmol) of methanesulfonyl chloride. After one hour 504 mg (1.8 mmol) of 4-(5H-dibenzo[a,b]cyclohepten-5-ylidene)-1-piperidine was added and the reaction mixture was allowed to stir at room temperature overnight. It was then poured into 1.0N aqueous sodium hydroxide and extracted with ethyl acetate (3×). The combined organic portions were washed with brine, dried over magnesium sulfate, filtered and concentrated in vacuo. The residue was purified via flash chromatography (3% methanol saturated with ammonia in methylene chloride) and crystallized (methylene chloride/isopropyl ether) to provide 103 mg of the title compound as a white solid: MS (FAB) m/z 381 (M$^+$+1).

EXAMPLE 5

4-[[4-(10,11-DIHYDRO-5H-DIBENZO[a,d]CYCLOHEPTEN-5-YLIDENE)-1-PIPERIDINYL]METHYL]PYRIDINE, 1-OXIDE

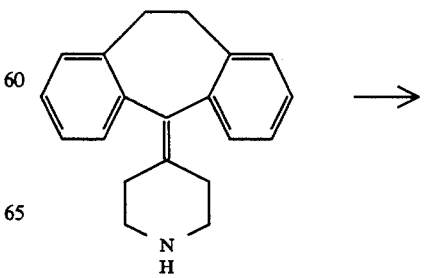

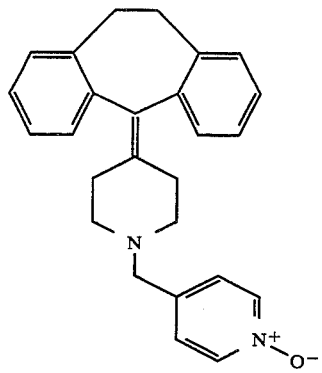

To a mixture of 452 mg (3.61 mmol) of 4-pyridylcarbinol N-oxide, 1.53 mL (11.0 mmol) of triethylamine in 30 mL of dry methylene chloride at 0° C. and under a nitrogen atmosphere was added 835 μL (10.8 mmol) of methanesulfonyl chloride. The mixture was slowly allowed to warm to room temperature. After three hours 1.00 g (3.64 mmol) of 4-(5H-dibenzo[a,b]cyclohepten-5-ylidene)-1-piperidine was added and the reaction mixture was allowed to stir at room temperature overnight. It was then poured into 1.0N aqueous sodium hydroxide and extracted with methylene chloride (3×). The combined organic portions were washed with brine, dried over magnesium sulfate, filtered and concentrated in vacuo. The residue was purified via flash chromatography (4% methanol saturated with ammonia in methylene chloride) to provide 208 mg of the title compound as a glass: MS (CI) m/e 383 (M+ +1).

EXAMPLE 6
1-(10,11-DIHYDRO-5H-DIBENZO[a,d]CYCLOHEPTEN-5-YL)-4-(4-PYRIDINYLMETHYL)-PIPERAZINE, N-OXIDE

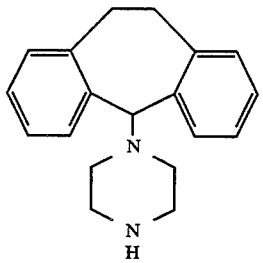 

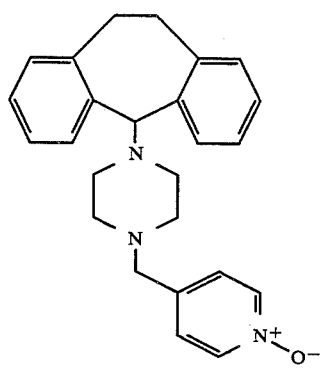

To a mixture of 190 mg (1.52 mmol) of 4-pyridylcarbinol N-oxide and 600 μL (4.31 mmol) of triethylamine in 15 mL of dry methylene chloride at −15° C. and under a nitrogen atmosphere was added 335 μL (4.33 mmol) of methanesulfonyl chloride. The reaction mixture was slowly allowed to warm to room temperature. After 3 hours 410 mg (1.47 mmol) of 1-(10,11-dihydro-5H-dibenzo[a,d]cyclohepten-5-yl)piperazine was added and the reaction mixture was allowed to stir at room temperature overnight. After another 18.3 hours the reaction mixture was poured into 1.0N aqueous sodium hydroxide and extracted with methylene chloride (3×). The combined organic portions were washed with brine, dried over magnesium sulfate, filtered and concentrated in vacuo. The residue was purified via flash chromatography (4% methanol in methylene chloride) and the purified product was then triturated with pentane to provide 49 mg of the title compound as a white solid: MS (FAB) m/z 386 (M+ +1).

EXAMPLE 7
8-CHLORO-6,11-DIHYDRO-3-METHYL-11-[1-(4-PYRIDINYLMETHYL)-4-PIPERIDINYLIDENE]-5H-BENZO[5,6]-CYCLOHEPTA[1,2-b]PYRIDINE, N-OXIDE

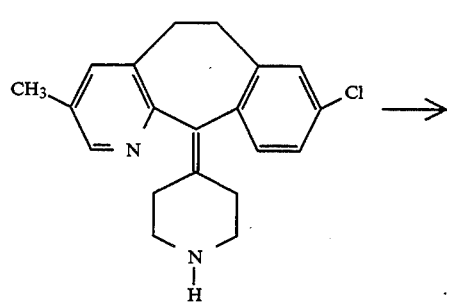

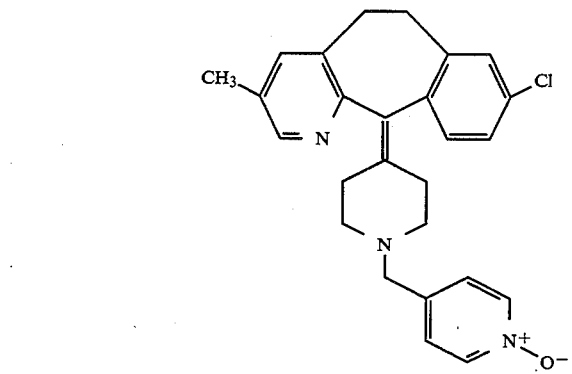

To a mixture of 4-pyridylcarbinol N-oxide (125 mg, 1.0 mmol) and CBr4 (331 mg 1.0 mmol) in CH2Cl2 (8 mL) under argon was added triphenylphosphine (262 mg. 1.0 mmol). This was allowed to stir for 30 minutes. Triethylamine (0.139 mL, 1.0 mmol) was added, followed by the addition of 3-methyl-8-chloro-6,11-dihydro-11-(4-piperdylidene)-5H-benzo[5,6]cyclohepta[1,2-b]pyridine (324 mg, 1.0 mmol). After stirring overnight, the reaction was diluted with 0.5N NaOH and then extracted with CH2Cl2 (2×). The organic portion was then washed with brine and then dried (Na2SO4). It was then filtered and solvent removed to give a solid which was chromoatographed with silica gel and eluted with 10% methanol in CH2Cl2 to give 195 mg of the title compound in 45% yield as a brownish solid. MS (FAB) m/z 432 (M+ +1).

EXAMPLE 8

8-CHLORO-5,11-DIHYDRO-11-[1-(4-PYRIDINYL-METHYL)-4-PIPERIDINYLIDENE][1]BENZOX-EPINO[4,3-b]PYRIDINE N'-OXIDE

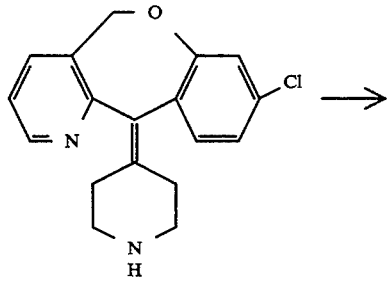

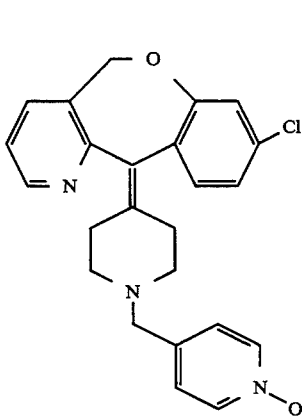

Add triphenylphosphine (2.00 g, 7.61 mmole) to 4-pyridylcarbinol N-oxide (0.95 g, 7.61 mmole) and carbon tetrabromide (2.52 g, 7.61 mmole) in dichloromethane (65 mL) under a nitrogen atmosphere. Stir for 45 minutes at room temperature. Add 8-chloro-5,11-dihydro-11-(4-piperidinylidene)[1]benzoxepino[4,3-b]pyridine (1.40 g, 4.48 mmole) and triethylamine (1.06 mL, 0.770 g, 7.61 mmole). Stir for 16 hours at room temperature. Add additional dichloromethane, wash with saturated NaHCO3 and saturated NaCl, dry with MgSO4, filter, and concentrate in vacuo. Dissolve the oil in dichloromethane, and chromatograph on silica gel, eluting with 10% methanoldichloromethane. Combine the appropriate fractions, and concentrate under reduced pressure to give the title compound as a foamy solid (0.28 g, 15% yield): m.p. 102°-105°; MS (EI) m/e 404 (M+ −16).

EXAMPLE 9

8-CHLORO-5,11-DIHYDRO-11[4-(4-PYRIDINYL-METHYL)-1-PIPERAZINYL][1]BENZOX-EPINO[4,3-b]PYRIDINE N'-OXIDE

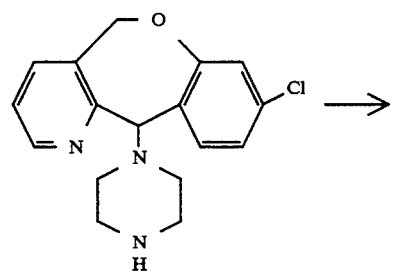

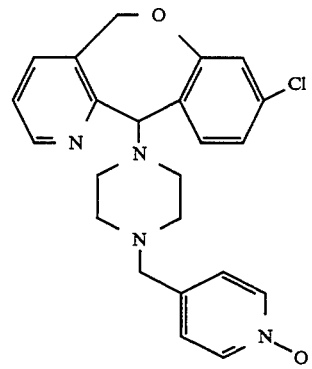

Add triphenylphosphine (2.82 g, 10.77 mmole) to 4-pyridylcarbinol N-oxide (1.35 g, 10.77 mmole) and carbon tetrabromide (3.57 g, 10.77 mmole) in dichloromethane (50 mL) under a nitrogen atmosphere. Stir for 45 minutes at room temperature. Add 8-chloro-5,11-dihydro-11-(1-piperazinyl)[1]benzoxepino[4,3-b]pyridine (2.00 g, 6.33 mmole) and triethylamine (1.50 mL, 1.09 g, 10.77 mmole). Stir for 17 hours at room temperature. Add saturated NaHCO3 (50 mL), and separate layers. Extract the aqueous solution with dichloromethane (2×50 mL). Wash the combined organic portions with saturated NaCl, dry with MgSO4, filter, and concentrate in vacuo. Dissolve the oil in dichloromethane, and chromatograph on silica gel, eluting with 7% methanol-dichloromethane. Combine appropriate fractions, and concentrate under reduced pressure to give a yellow solid. Dissolve the solid in ethanol, and add 1.1 equivalents of maleic acid. Add ether to precipitate the maleate salt, filter, wash with ether, and dry under high vacuum to give the title compound as a white solid (1.02 g, 73% yield): m.p. 179°-181° C.; MS (FAB) m/z 423(M+ +1).

EXAMPLE 10

8-CHLORO-5,11-DIHYDRO-11-[1-(4-PYRIDINYL-METHYL)-4-PIPERIDINYLIDENE][1]BENZO-THIEPINO[4,3-b]PYRIDINE N'-OXIDE

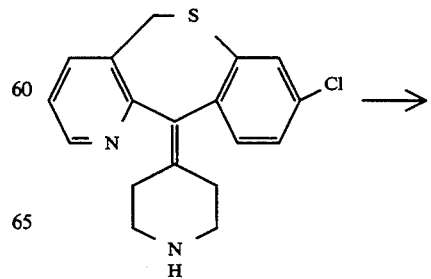

-continued

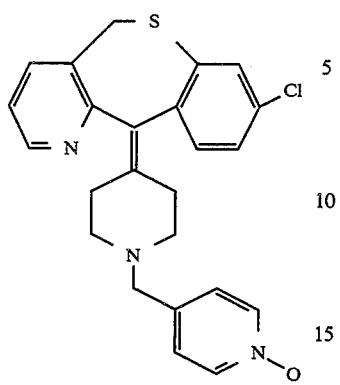

A mixture of 4-pyridinylcarbinol N-oxide (943 mg, 7.53 mmol) and triphenylphosphine (3.95 g, 15.1 mmol) in carbon tetrachloride (25 mL) was refluxed under nitrogen for 3.5 hours. Acetonitrile (5 mL) was added and the mixture was refluxed for 5 min and then allowed to stand overnight. The mixture was filtered through celite and the filtrate concentrated in vacuo. The residue was flash chromatographed, eluting with 10% methanol in methylene chloride to give 4-chloromethylpyridine N-oxide (432 mg) as a black gum.

A suspension of 8-chloro-5,11-dihydro-11-(4-piperidinylidene)[1]benzothiepino[4,3-b]pyridine N-oxide (246 mg, 0.748 mmol), triethylamine (0.11 mL, 0.79 mmol) and 4-chloromethyl-pyridine N-oxide (226 mg, 1.57 mmole) in acetonitrile (10 mL) was stirred at room temperature for 20 hr. followed by 20 hr. at 40° C. The mixture was concentrated in vacuo to provide a residue which was purified by flash chromatography. The product was titurated with ether/hexanes (1:1) to give the title compound (148 mg) as a solid: m.p. 125.5°–131.5° C. (dec); MS (FAB) m/z 436 (M+ +1).

EXAMPLE 11

8-CHLORO-5,11-DIHYDRO-11-[4-(4-PYRIDINYL-METHYL)-1-PIPERAZINYL][1]BENZO-THIEPINO[4,3-b]PYRIDINE N'-OXIDE

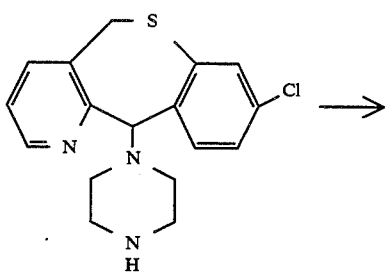

-continued

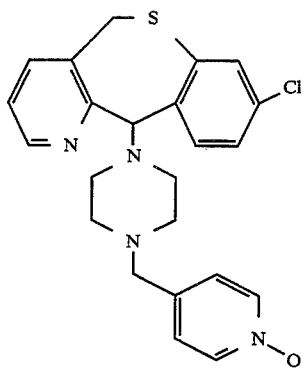

To a solution of 4-pyridinylcarbinol N-oxide (0.96 g, 7.67 mmol) and carbon tetrabromide (2.55 g, 7.69 mmole) in methylene chloride (18 mL) at 15°–25° C. was added triphenylphosphine (2.02 g, 7.7 mmol). After stirring for 30 min. an additional amount of triphenylphosphine (2.02 gm., 7.7 mmol) was added. After stirring for 20 min. at 10°–15° C., a solution of 8-chloro-5,11-dihydro-11-(1-piperazinyl)[1]benzothiepino[4,3-b]pyridine (1.01 g, 3.04 mmol) in methylene chloride (5 mL) was added followed by a solution of triethylamine (1.07 mL, 7.1 mmol) in methylene chloride (1 mL) at 7°–9.5° C. The reaction mixture was warmed to room temperature and stirred for 24 hours. It was poured onto ice, stirred with methylene chloride, filtered through celite and separated. The aqueous layer was extracted with methylene chloride (3×) and the organic portions combined. After washing with water (3×) and brine (1×) and drying over Na2SO4, the solution was concentrated in vacuo to give a crude product (3.8 g). It was flash chromatographed (90:9:0.125 CH2Cl2:MeOH:HOAc) to give the title compound (135.8 mg) of high purity by tlc. This material was combined with other material obtained from additional experiments run similarly and flash chromatographed three times (95:5:0.125 and then 90:10:0.125 CH2Cl2:MeOH:NH4OH) to give the title compound as a solid: m.p. 122°–126.5° C. (dec); MS (FAB) m/z 439 (M+ +1).

EXAMPLE 12

10[1-(4-PYRIDINYLMETHYL)-4-PIPERIDINYLIDENE]-10H -[1]BEN-ZOPYRANO[3,2b]PYRIDINE N'-OXIDE

125
-continued

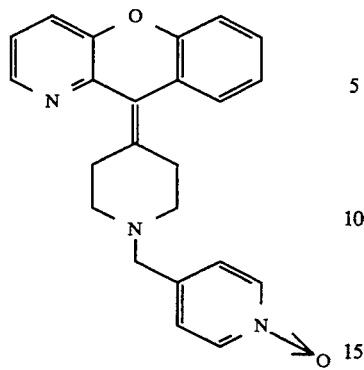

To a solution of 4-pyridylcarbinol N-oxide (381 mg) and carbon tetrabromide (1.02 g) in 25 mL CH$_2$Cl$_2$ was added triphenylphosphine (811 mg). The solution was allowed to stir for 1 hour. To this was added 10-[4-piperidinylidene]-10H-[1]benzopyrano-[3,2-b]pyridine (480 mg) followed by triethylamine (431 μL). This was stirred for 1.5 hours. The mixture was diluted with 150 mL CH$_2$Cl$_2$, washed 1× with 0.5M aqueous K$_2$CO$_3$ solution, washed 1× with brine and then dried (Na$_2$SO$_4$). It was then filtered and the solvent removed. The crude product was chromatographed on silica gel, eluted with 3% MeOH saturated with NH$_3$ in CH$_2$Cl$_2$ to afford the title compound (465 mg): MS (EI) m/e 371 (M+).

EXAMPLE 13
1-(9H-FLUOREN-9-YL)-4-(4-PYRIDINYLMETHYL)PIPERAZINE N$^4$-OXIDE

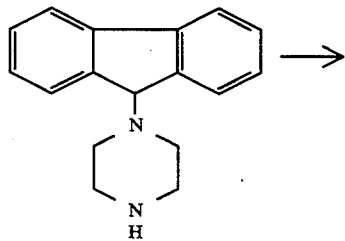 →

126
-continued

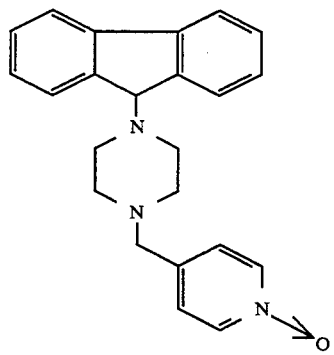

To a solution of 4-pyridylcarbinol N-oxide (423 mg) and carbon tetrabromide (1.1 g) in 28 mL CH$_2$Cl$_2$ was added triphenylphosphine (888 mg) at room temperature. After 1 hour 1-(9H-flouren-9-yl)-piperazine (500 mg) was added followed by triethylamine (471 mg). After stirring for 3.5 hours, the reaction was washed 1× with 0.5M aqueous NaHCO$_3$, washed once with brine and then dried (Na$_2$SO$_4$). It was then filtered and the solvent removed to give a crude product which was chromatographed on silica gel, eluted with 5% MeOH saturated with NH$_3$ in CH$_2$Cl$_2$ to afford the title compound (378 mg) as a white solid: mp 192°–194° C.; MS (FAB) m/z 378 (M+ +1).

EXAMPLE 14

If one were to employ essentially the same procedure set forth in Example 7 above but using the amines set forth in column 1 below in place of 3-methyl-8-chloro-6,11-dihydro-11-(4-piperdylidene)-5H-benzo[5,6]cyclohepta[1,2-b]pyridine, then one could obtain the compounds listed in column 2 of TABLE 6 below:

TABLE 6

| Column 1 | Column 2 |
|---|---|
| ![structure with OH and Cl, NH piperidine] | ![structure with OH and Cl, N-CH2-pyridine N-oxide] |

TABLE 6-continued
| Column 1 | Column 2 |
|---|---|
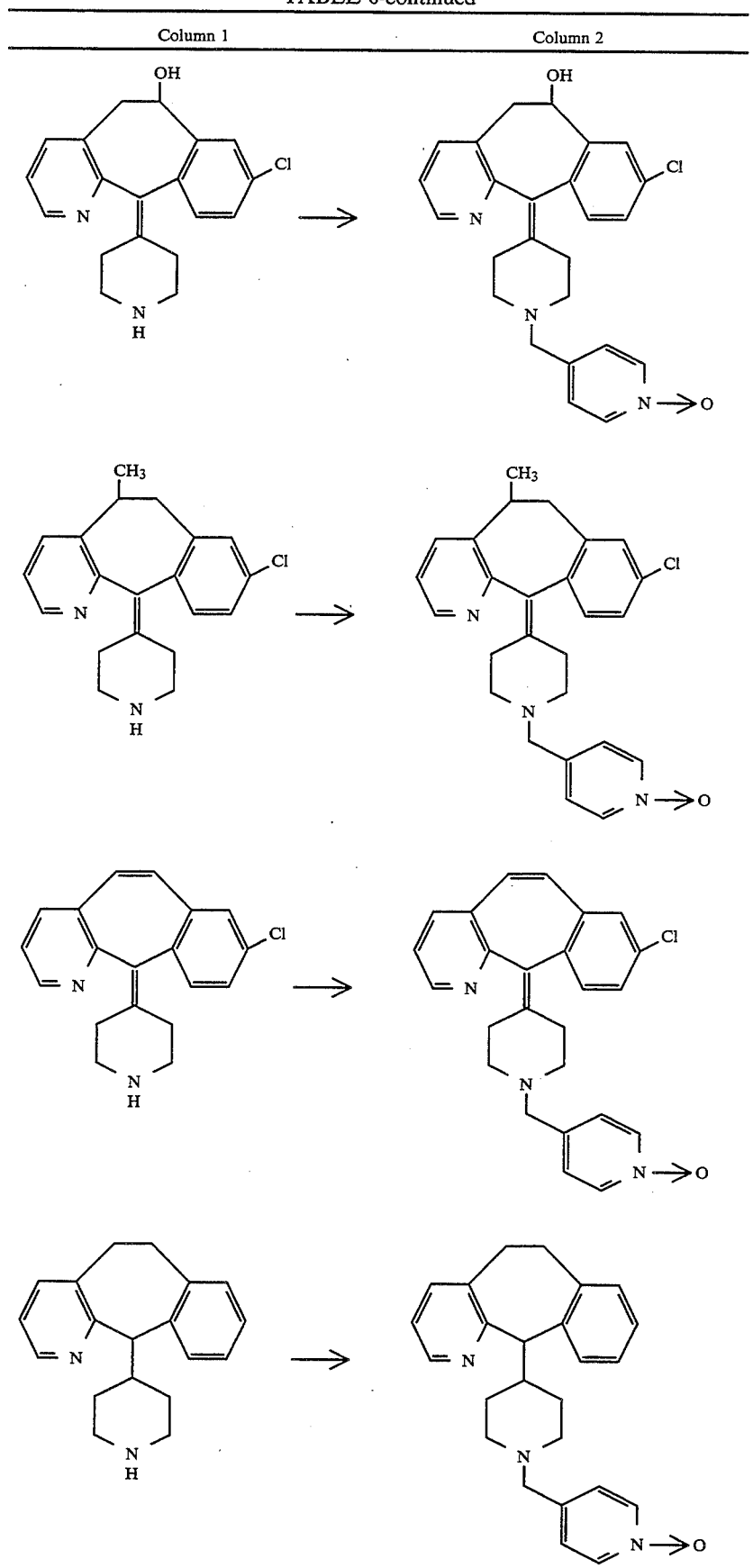

TABLE 6-continued
| Column 1 | Column 2 |
|---|---|
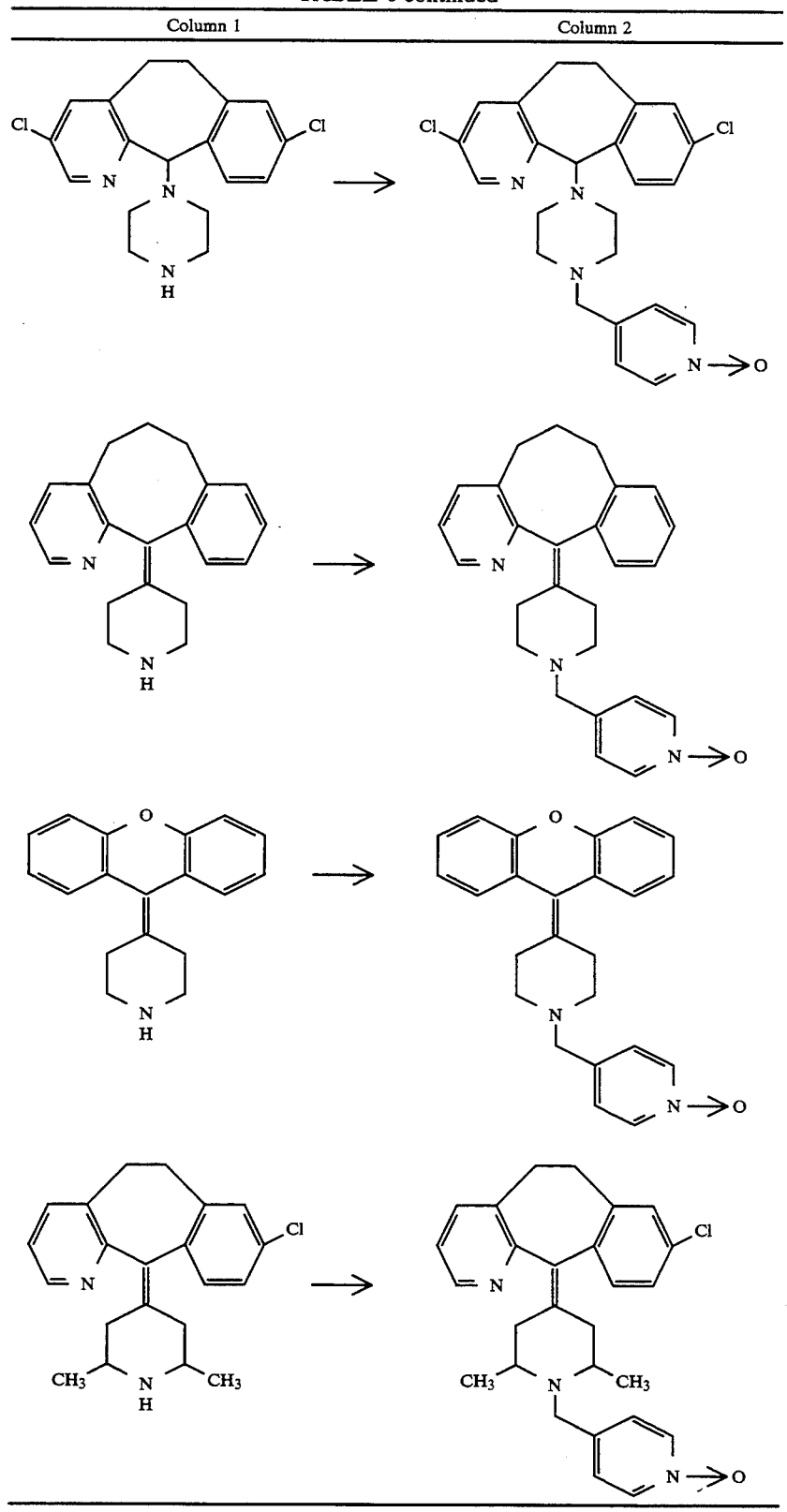
EXAMPLE 15
By employing essentially the same procedure set forth in Example 7 above, but using the carbinols set forth in column 1 below in place of 4-pyridylcarbinol N-oxide, one can obtain the compounds listed in column 2 of TABLE 7 below:

TABLE 7

| Column 1 | Column 2 |
|---|---|

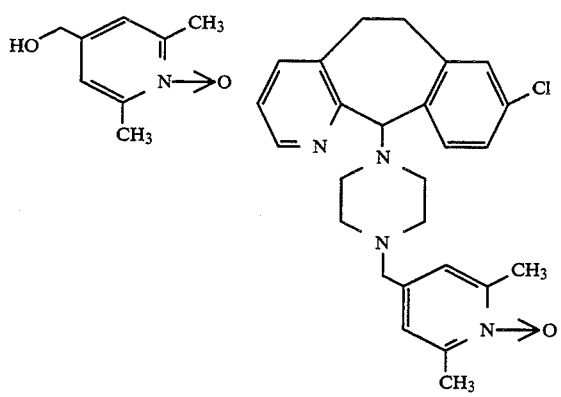

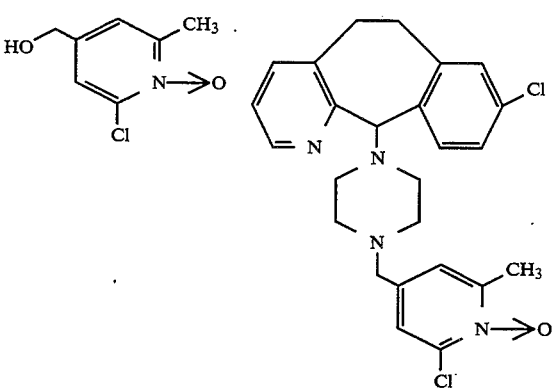

The following are examples of pharmaceutical dosage forms which contain a compound of the invention. As used therein, the term "active compound" is used to designate the compound

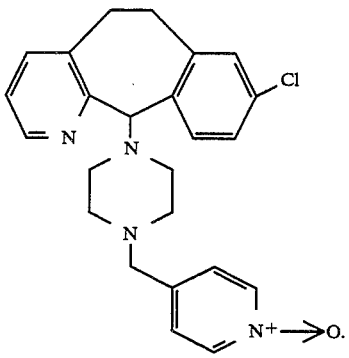

The scope of the invention in its pharmaceutical composition aspect is not to be limited by the examples provided, since any other compound of structural formula I can be substituted into the pharmaceutical composition examples.

Pharmaceutical Dosage Form Examples

EXAMPLE A

Tablets

| No. | Ingredients | mg/tablet | mg/tablet |
|---|---|---|---|
| 1. | Active compound | 100 | 500 |
| 2. | Lactose USP | 122 | 113 |
| 3. | Corn Starch, Food Grade, as a 10% paste in | 30 | 40 |
| 4. | Purified Water | | |
| 4. | Corn Starch, Food Grade | 45 | 40 |
| 5. | Magnesium Stearate | 3 | 7 |
| | Total | 300 | 700 |

Method of Manufacture

Mix Item Nos. 1 and 2 in a suitable mixer for 10–15 minutes. Granulate the mixture with Item No. 3. Mill the damp granules through a coarse screen (e.g., ¼", 0.63 cm) if necessary. Dry the damp granules. Screen the dried granules if necessary and mix with Item No. 4 and mix for 10–15 minutes. Add Item No. 5 and mix for 1–3 minutes. Compress the mixture to appropriate size and weigh on a suitable tablet machine.

EXAMPLE B

Capsules

| No. | Ingredient | mg/capsule | mg/capsule |
|---|---|---|---|
| 1. | Active compound | 100 | 500 |
| 2. | Lactose USP | 106 | 123 |
| 3. | Corn Starch, Food Grade | 40 | 70 |
| 4. | Magnesium Stearate NF | 7 | 7 |
| | Total | 250 | 700 |

Method of Manufacture

Mix Item Nos. 1, 2 and 3 in a suitable blender for 10–15 minutes. Add Item No. 4 and mix for 1–3 minutes. Fill the mixture into suitable two-piece hard gelatin capsules on a suitable encapsulating machine.

While the present invention has been described in conjunction with the specific embodiments set forth above, many alternatives, modifications and variations thereof will be apparent to those of ordinary skill in the art. All such alternatives, modifications and variations

We claim:
1. A compound of the formula:

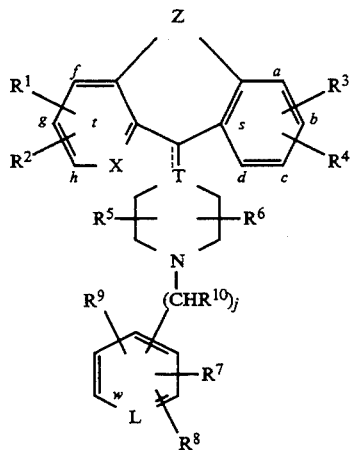

or a pharmaceutically acceptable salt or solvate thereof, wherein:

Z represents —(C(R$^a$)$_2$)$_m$—Y—(C(R$^a$)$_2$)$_n$— or

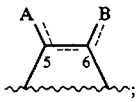

L represents N or N$^+$O$^-$;

X represents CH, N or NR$^{12}$, wherein R$^{12}$ is —O$^-$ or —CH$_3$;

R$^1$, R$^2$, R$^3$, and R$^4$ may be the same or different and each independently represents H, halo, —CF$_3$, —OR$^{11}$, —C(=O)R$^{11}$, —SR$^{11}$, —S(O)$_e$R$^{13}$ wherein e is 1 or 2, —N(R$^{11}$)$_2$, —NO$_2$, —OC(=O)R$^{11}$, —CO$_2$R$^{11}$, CN, —OCO$_2$R$^{13}$, —NR$^{11}$C(=O)R$^{11}$, alkyl, aryl, alkenyl or alkynyl, which alkyl group may be substituted with —OR$^{11}$, —SR$^{11}$, —N(R$^{11}$)$_2$ or —CO$_2$R$^{11}$ and which alkenyl group may be substituted with halo, —OR$^{13}$ or —CO$_2$R$^{11}$;

R$^5$ and R$^6$ each independently represents H or alkyl which alkyl may be substituted with —OR$^{11}$, —SR$^{11}$ or —N(R$^{11}$)$_2$;

in addition, R$^5$ may be combined with R$^6$ to represent =O or =S;

R$^7$, R$^8$ and R$^9$ each independently represents H, halo, —CF$_3$, —OR$^{11}$, —C(O)R$^{11}$, —SR$^{11}$, —S(O)$_e$R$^{13}$ wherein e is 1 or 2, —N(R$^{11}$)$_2$, —NO$_2$, —CO$_2$R$^{11}$, CN, —OCO$_2$R$^{13}$, —OCOR$^{11}$, alkyl, aryl, alkenyl or alkynyl, which alkyl group may be substituted with —OR$^{11}$, —SR$^{11}$, —N(R$^{11}$)$_2$, or —CO$_2$R$^{11}$ and which alkenyl group may be substituted with halo, —OR$^{13}$ or —CO$_2$R$^{11}$;

m and n are integers 0, 1 or 3, such that the sum of m plus n equals 0, 1 or 3;

when m plus n equals 0, Y represents —O—, —S(O)$_e$— (wherein e is 0, 1 or 2), —NR$^{11}$— or a direct bond;

when m plus n equals 1, Y represents —O—, —S(O)$_e$— (wherein e is 0, 1 or 2), or —NR$^{11}$—;

when m plus n equals 3, Y represents a direct bond;

R$^{10}$ represents H or alkyl;

each R$^{11}$ independently represents H, alkyl or aryl;

each R$^{13}$ independently represents alkyl or aryl;

each R$^{14}$ independently represents H or alkyl;

each R$^a$ independently represents H or lower alkyl;

j represents 1, 2 or 3;

T represents CH, C or N, with the dotted line attached to T representing a double bond when T is C and being absent when T is CH or N;

when Z represents

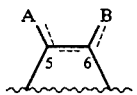

the dotted line between carbon atoms 5 and 6 represents an optional double bond, such that when a double bond is present, A and B each independently represent —R$^{11}$, —OR$^{13}$, halo or —OC(O)R$^{11}$, and when no double bond is present between carbon atoms 5 and 6, A and B each independently represent H$_2$, —(OR$^{13}$)$_2$, (alkyl and H), (alkyl)$_2$, (—H and —OC(O)R$^{11}$), (H and —OR$^{11}$), =O or =NOR$^{14}$; and with the proviso that when Z represents

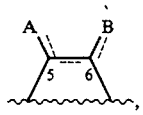

and X represents CH, and T represents C such that the dotted line attached to T represents a double bond, then L represents N$^+$O$^-$; and wherein in the above said alkyl contains from one to twenty carbon atoms, said alkenyl contains from 2 to 12 carbon atoms, said alkynyl contains from 2 to 12 carbon atoms, and said aryl represents a carbocyclic group containing from 6 to 14 carbon atoms and having at least one phenyl or fused phenylene ring.

2. The compound of claim 1 further characterized by R$^1$, R$^2$, R$^3$, and R$^4$ each independently representing H, alkyl, halo, —N(R$^{11}$)$_2$ or —OR$^{11}$.

3. The compound of claim 1 further characterized by R$^5$ and R$^6$ each independently representing H or lower alkyl.

4. The compound of claim 1 further characterized by R$^7$ and R$^8$ each representing H.

5. The compound of claim 1 further characterized by R$^9$ representing H, halo, —CF$_3$, —OR$^{11}$, —SR$^{11}$, —N(R$^{11}$)$_2$, or lower alkyl.

6. The compound of claim 1 further characterized by R$^9$ representing H.

7. The compound of claim 1 further characterized by T representing N or C.

8. The compound of claim 1 further characterized by L being in the para position relative to the bond connecting ring w to the rest of the compound.

9. The compound of claim 1 further characterized by j representing 1.

10. The compound of claim 1 further characterized by R$^{10}$ representing H.

11. The compound of claim 1 further characterized by R$^{11}$ representing H or lower alkyl.

12. The compound of claim 1 further characterized by Z representing

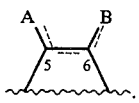

13. The compound of claim 12 further characterized by the double bond being absent between carbon atoms 5 and 6, and by both A and B being represented by H₂, or by one of A or B being (H and OH) or =O and the other being H₂.

14. The compound of claim 12 further characterized by R⁷ and R⁸ each independently representing H, halo, CF₃, OR¹¹, SR¹¹, N(R¹¹)₂ or lower alkyl.

15. The compound of claim 12 further characterized by L representing N⁺O⁻.

16. The compound of claim 12 further characterized by L representing N.

17. The compound of claim 15 or 16 further characterized by X being represented by N or N⁺O⁻.

18. The compound of claim 15 or 16 further characterized by X being represented by CH.

19. The compound of claim 15 or 16 further characterized by T being represented by N or CH and by the optional double bond to T being absent.

20. The compound of claim 15 further characterized by T representing C, by the optional double bond to T being present, and by L representing N⁺O⁻.

21. The compound of any of claim 15 or 16 further characterized by R¹ and R² each independently representing H, alkyl or halo.

22. The compound of claim 15 or 16 further characterized by R³ and R⁴ each independently representing H or halo.

23. The compound of claim 15 or 16 further characterized by R³ representing H, Cl, Br or F at C-8 of the fused ring portion of the compound, and R⁴ representing H at the C-9 position of the fused ring portion of the compound.

24. The compound of any of claim 15 or 16 further characterized by R⁷, R⁸, and R⁹ representing H.

25. The compound of claim 12 further characterized by having the formula:

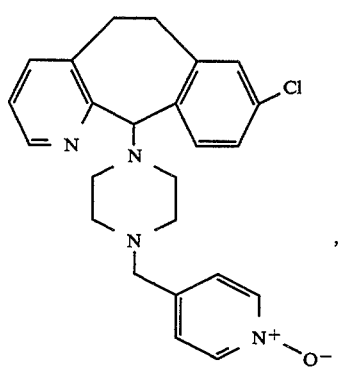

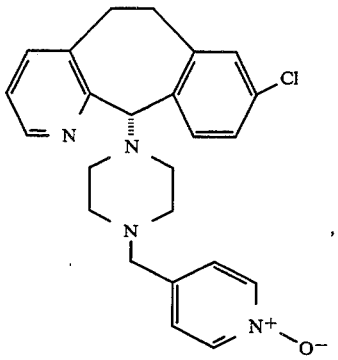

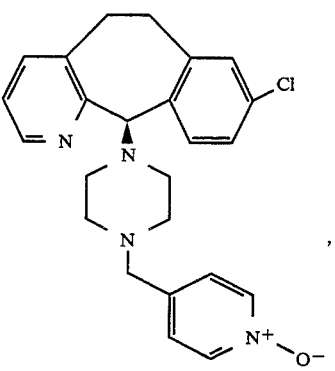

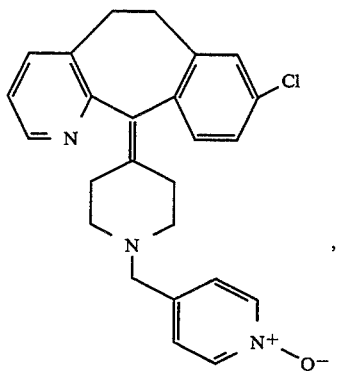

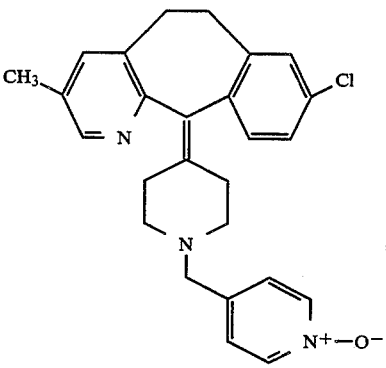

-continued

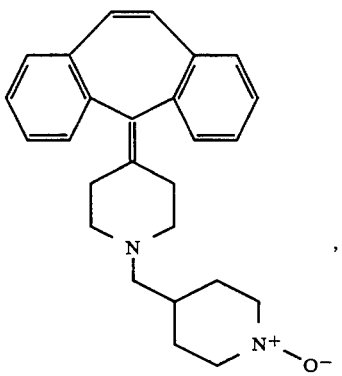,

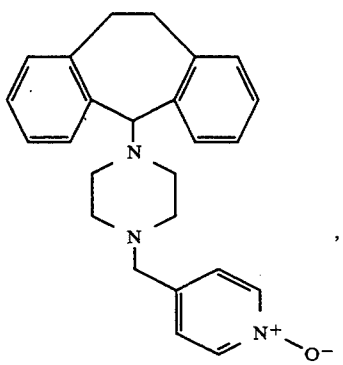,

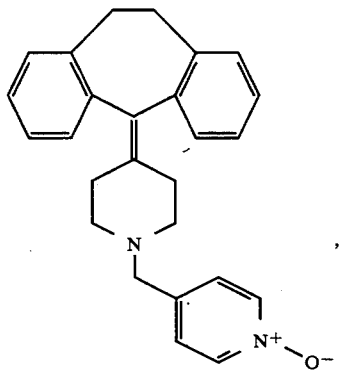, or

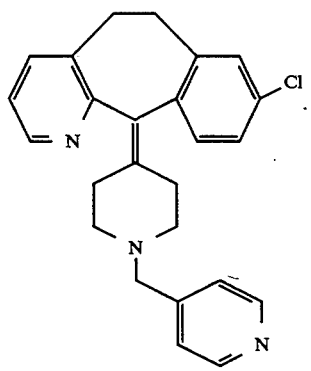

26. The compound of claim 1 further characterized by Z representing —(C(R$^a$)$_2$)$_m$—Y—(C(R$^a$)$_2$)$_n$—.

27. The compound of claim 26 further characterized by R$^7$ and R$^8$ each independently representing H, halo, —CF$_3$, —OR$^{11}$, —SR$^{11}$, —N(R$^{11}$)$_2$, or alkyl.

28. The compound of claim 26 further characterized by Z representing —C(R$^a$)$_2$—Y—, —Y—C(R$^a$)$_2$—, —Y—, —CH$_2$CH$_2$CH$_2$— or a direct bond where Y represents —O—, —S—, or —NR$^{10}$.

29. The compound of any of claim 26 further characterized by L representing N$^+$O$^-$.

30. The compound of any of claim 26 further characterized by L representing N.

31. The compound of claim 29 or 30 further characterized by Z representing —CH$_2$—Y—, —Y—CH$_2$—, —Y—, —CH$_2$CH$_2$CH$_2$— or a direct bond, wherein Y represents —O— or —S—.

32. The compound of claim 29 or 30 further characterized by R$^1$ and R$^2$ each independently representing H, alkyl or halo.

33. The compound of claim 29 or 30 further characterized by R$^3$ and R$^4$ each independently representing H or halo.

34. The compound of any of claim 29 or 30 further characterized by T representing N or CH and the optional double bond to T is absent.

35. The compound of claim 29 or 30 further characterized by T representing C and the optional double bond to T being present.

36. The compound of claim 29 or 30 further characterized by R$^7$, R$^8$ and R$^9$ representing H.

37. The compound of claim 26 further characterized by having the formula:

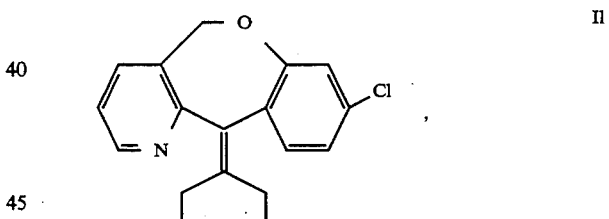 II

,

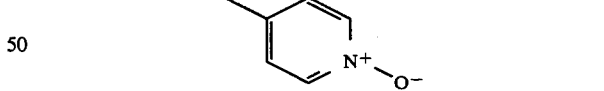

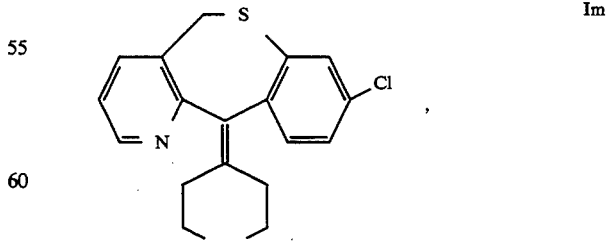 Im

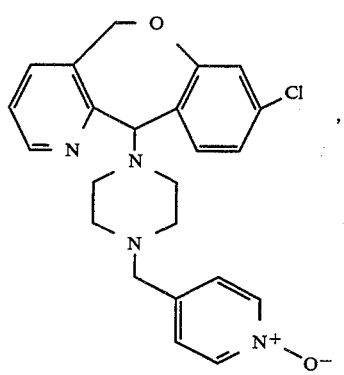

In

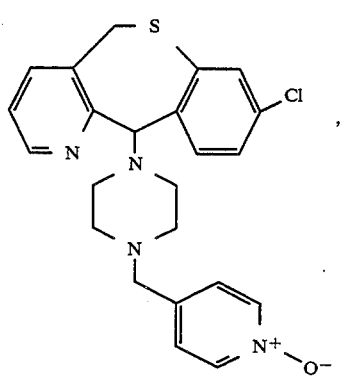

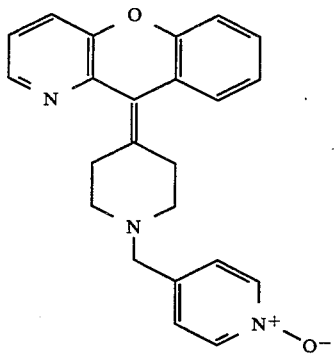

Ip

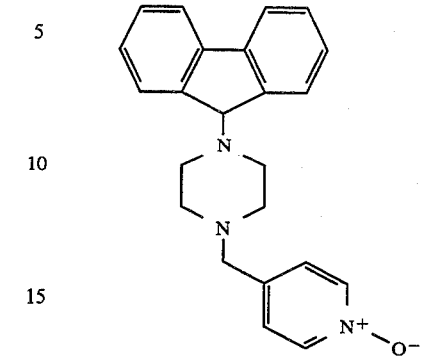

Io

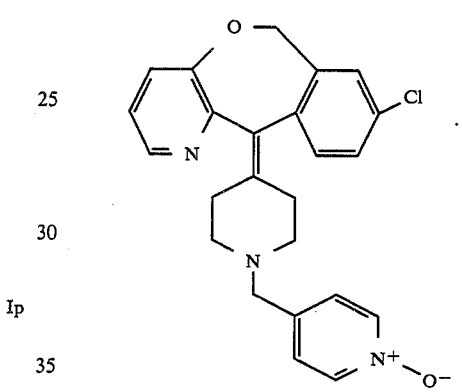

Iq and

38. The compound of claim 26 further characterized by having the formula:

39. A pharmaceutical composition, for use in treating allergic reaction or inflammation in a mammal, comprising an effective amount of a compound of claim 1 in combination with a pharmaceutically acceptable carrier.

40. A method for treating allergic reaction or inflammation in a mammal comprising administering to the mammal an antiallergic or antiinflammatory effective amount of a compound of claim 1.

* * * * *